(12) United States Patent
Brown et al.

(10) Patent No.: US 8,790,902 B2
(45) Date of Patent: Jul. 29, 2014

(54) MICROORGANISMS HAVING ENHANCED TOLERANCE TO INHIBITORS AND STRESS

(75) Inventors: Steven D. Brown, Knoxville, TN (US); Shihui Yang, Knoxville, TN (US)

(73) Assignee: UT-Batelle, LLC, Oak Ridge, TN (US)

( * ) Notice: Subject to any disclaimer, the term of this patent is extended or adjusted under 35 U.S.C. 154(b) by 0 days.

(21) Appl. No.: 13/589,709

(22) Filed: Aug. 20, 2012

(65) Prior Publication Data
US 2012/0329112 A1 Dec. 27, 2012

Related U.S. Application Data

(62) Division of application No. 12/795,882, filed on Jun. 8, 2010, now abandoned.

(60) Provisional application No. 61/184,961, filed on Jun. 8, 2009.

(51) Int. Cl.
| | | |
|---|---|---|
| C12P 7/04 | (2006.01) | |
| C12P 7/06 | (2006.01) | |
| C12N 1/00 | (2006.01) | |
| C12N 15/00 | (2006.01) | |
| C12N 15/74 | (2006.01) | |
| C07K 1/00 | (2006.01) | |

(52) U.S. Cl.
USPC . 435/157; 435/161; 435/254.11; 435/254.21; 435/254.22; 435/254.23; 435/320.1; 435/471; 530/350

(58) Field of Classification Search
USPC .......... 435/157, 161, 254.11, 254.21, 254.22, 435/254.23, 320.1, 471; 530/350
See application file for complete search history.

(56) References Cited

U.S. PATENT DOCUMENTS

| | | |
|---|---|---|
| 5,514,583 A | 5/1996 | Picataggio et al. |
| 5,712,133 A | 1/1998 | Picataggio et al. |
| 5,726,053 A | 3/1998 | Picataggio et al. |
| 5,843,760 A | 12/1998 | Xhang et al. |
| 7,285,403 B2 | 10/2007 | Jeffries et al. |
| 2006/0234364 A1 | 10/2006 | Rajgarhia et al. |
| 2008/0254524 A1 | 10/2008 | Abbas et al. |

OTHER PUBLICATIONS

Muren et al., Identification of yeast deletion strains that are hypersensitive to brefeldin A or monensin, two drugs that affect intracellular transport. Yeast, 2001, vol. 18: 163-172.*
Tanaka et al., Functional genomic analysis of commercial baker's yeast during initial stages of model dough-fermentation. Food Micrbiol., 2006, vol. 23: 717-728.*
Broun et al., Catalytic plasticity of fatty acid modification enzymes underlying chemical diversity of plant lipids, Science, 1998, vol. 282: 1315-1317.
Chica et al., Semi-rational approaches to engineering enzyme activity: combining the benefits of directed evolution and rational design. Curr. Opi. Biotechnol., 2005, vol. 16: 378-384.
Devos et al., Practical limits of function prediction. Proteins: Structure, Function, and Genetics, 2000, vol. 41: 98-107.
Kimchi-Sarfaty et al., A "Silent" polymorphism in the MDR1 gene changes substrate specificty. Science, 2007, vol. 315: 525-528.
Kisselev L., Polypeptide release factors in prokaryotes and eukaryotes: same function, different structure. Structure, 2002, vol. 10: 8-9.
Nackley et al., Human Caechol-O-Methytransferase haplotypes modulate protein expression by altering mRNA secondary structure, Science, 2006, vol. 314: 1930-1933.
Reijns et al., Analysis of Lsm 1p and Lsm 8p domains in the cellular localization of Lsm complexes in budding yeast. FEBS Journal., 2009, vol. 276: 3602-3617.
Sauna et al., Silent polymorhisms speak: How they affect pharmacogenomics and the treatment of cancer. Cancer Res., 2007, vol. 67(20): 9609-9612.
Seffernick et al., Melamine deaminase and Atrazine chlorohydrolase: 98 percent identical but functionally different. J. Bacteriol., 2001, vol. 183 (8): 2405-2410.
Spiller et al., Requirements for nuclear localization of the Lsm2-8p complex and competition between nuclear and cytoplasmic complexes. J. Cell Sci., 2007, vol. 120: 4310-4320.
Whisstock et al., Prediction of protein function form protein sequence, Q. Rev. Biophysics., 2003, vol. 36 (3): 307-340.
Wishart et al., A single mutation converts a novel phosphotyrosine binding domain into a dual-specificity phosphatase. J. Biol. Chem., 1995, vol. 270(45): 26782-26785.
Witkowski et al., Conversion of b-ketoacyl synthase to a Malonyl Decarboxylase by replacement of the active cysteine with glutamine. Biochemistry, 1999, vol. 38: 11643-11650.
Alexeyev, M.F., "The pKNOCK Series of Broad-host-range Mobilizable Suicide Vectors for Gene Knockout and Targeted DNA Insertion into the Chromosome of Gram-negative Bacteria" Biotechniques (1999) pp. 824-826, vol. 26.
Almeida, J.R.M. et al., "Increased Tolerance and Conversion of Inhibitors in Lignocellulosic Hydrolysates by *Saccharomyces cerevisiae*" Journal of Chemical Technology and Biotechnology (2007) pp. 340-349, vol. 82(4).
Amberg, D.C. et al., "Methods in Yeast Genetics: A cold Spring Harbor Laboratory Course Manual" New York: Cold Spring Harbor Press (2005).
Baumler, D.J. et al., "Enhancement of Acid Tolerance in *Zymomonas mobilis* by a Proton-buffering Peptide" Appl Biochem Biotechnol (2006) pp. 15-26, vol. 134(1).

(Continued)

*Primary Examiner* — Ganapathirama Raghu
(74) *Attorney, Agent, or Firm* — Scully, Scott, Murphy & Presser, P.C.

(57) ABSTRACT

The present invention provides genetically modified strains of microorganisms that display enhanced tolerance to stress and/or inhibitors such as sodium acetate and vanillin. The enhanced tolerance can be achieved by increasing the expression of a protein of the Sm-like superfamily such as a bacterial Hfq protein and a fungal Sm or Lsm protein. Further, the present invention provides methods of producing alcohol from biomass materials by using the genetically modified microorganisms of the present invention.

9 Claims, 20 Drawing Sheets

(56) References Cited

OTHER PUBLICATIONS

Brown, S.D., "Analysis of a 16 kb Region of the *Mesorhizobium loti* R7A Symbiosis Island Encoding bio and nad loci and a Novel Member of the IacI Family Dunedin" University of Otago (2002).

Brown, S.D. et al., "Cellular Response of *Shewanella oneidensis* to strontium Stress" Applied and environmental microbiology (2006) pp. 890-900, vol. 72(1).

Chinnawirotpisan, P. et al., "Quinoprotein Alcohol Dehydrogenase is Involved in Catabolic Acetate Production, While NAD-dependent Alcohol Dehydrogenase in Ethanol Assimilation in *Acetobacter pasteurianus* SKU1108" Journal of Bioscience Bioeng (2003) pp. 564-571, vol. 96(6).

Fukaya, M. et al., "Cloning of Genes Responsible for Acetic Acid Resistance in *Acetobacter aceti*" Journal of Bacteriology (1990) pp. 2096-2104, vol. 172(4).

Fukaya, M. et al., "The aarC Gene Responsible for Acetic Acid Assimilation Confers Acetic Acid Resistance on *Acetobacter aceti*" Journal of Fermentation and Bioengineering (1993) pp. 270-275, vol. 76(4).

Guisbert, E. et al., "Hfq the •E-MediatedEnvelope Stress Response and the •32-MediatedCytoplasmic Stress Response in *Escherichia coli•*",Journal of Bacteriology 2007 189(5): 1963-1973.

Herman et al., EMBO Journal (1995) pp. 2976-2088, vol. 14.

Jeon, Y.J. et al., "Kinetic Analysis of Ethanol Production by an Acetate-Resistant Strain of Recombinant *Zymomonas mobilis*" Biotechnology Letters (2002) pp. 819-824, vol. 24(10).

Joachimstahl, E. et al., "A Mutant of *Zymomonas mobilis* ZM4 Capable of Ethanol Production from Glucose in the Presence of High Acetate Concentrations" Biotechnology Letters (1998) pp. 137-142, vol. 20(2).

Joachimsthal, E. et al., "Characterization of a High-Productivity Recombinant Strain of *Zymomonas mobilis* for Ethanol Production From Glucose/Xylose Mixtures" Applied Biochemistry and Biotechnology (2000) pp. 343-356, vol. 84(6).

Kalogeraki, V.S. et al., "Suicide Plasmids Containing Promoterless Reporter Genes can Simultaneously Disrupt and Create Fusions to Target Genes of Diverse Bacteria" Gene (1997) pp. 69-75, vol. 188(1).

Koch, B. et al., "A Panel of Tn7-based Vectors for Insertion of the gfp Marker Gene or for Delivery of Cloned DNA into Gram-negative Bacteria at a Neutral Chromosomal Site" Journal of Microbiol Meth (2001) pp. 187-195, vol. 45(3).

Lawford, H.G. et al., "Effects of pH and Acetic Acid on Glucose and Xylose Metabolism by a Genetically Engineered Ethanologenic *Escherichia coli*" Applied Biochemistry and Biotechnology (1993) pp. 301-322, vol. 39/40.

Lawford, H.G. et al., "Improving Fermentation Performance of Recombinant *Zymomonas* in Acetic Acid-Containing Media" Applied Biochemistry and Biotechnology (1998) pp. 161-172, vol. 70-72.

Lawford, H.G. et al., "Fermentation Performance Assessment of a Genomically Integrated Xylose-Utilizing Recombinant of *Zymomonas mobilis* 39676" Applied Biochemistry and Biotechnology (2001) pp. 117-131, vol. 91-93.

Mohagheghi, A. et al., "Performance of a Newly Developed Integrant of *Zymomonas mobilis* for Ethanol Production on Corn Stover Hydrolysate" Biotechnology Letters (2004) pp. 321-325, vol. 26(4).

Mullins, E.A. et al., "A Specialized Citric Acid Cycle Requiring Succinyl-Coenzyme A (CoA): Acetate CoA-Transferase (AarC) Confers Acetic Acid Resistance on the Acidophile *Acetobacter aceti*" Journal of Bacteriology (2008) pp. 4933-4940, vol. 190(14).

Okumura, H. et al., "Biochemical Characteristics of Spontaneous Mutants of *Acetobacter aceti* Deficient in Ethanol Oxidation" Agricultural Biological Chemistry (1985) pp. 2485-2487, vol. 49(8).

Pecota, D.C. et al., "Combining the hok/sok, parDE, and pnd Postsegregational Killer loci to Enhance Plasmid Stability" Appl Environ Microbiol (1997) pp. 1917-1924, vol. 63(5).

Pelletier, D.A. et al., "A General System for Studying Protein-Protein Interactions in Gram-Negative Bacteria" Journal of Proteome Research (2008) pp. 3319-3328, vol. 7(8).

Steiner, P. et al., "Overexpression of the ATP-Dependent Helicase RecG Improves Resistance to Weak Organic Acids in *Escherichia coli*" Applied Microbiology and Biotechnology (2003) pp. 293-299, vol. 63(3).

Takemura, H. et al., "Novel Insertion Sequence IS1380 from *Acetobacter pasteurianus* is Involved in Loss of Ethanol Oxidizing Ability" (1991) Journal of Bacteriology (1991) pp. 7070-7076, vol. 173(22).

Tsui, H.C. et al., "Characterization of Broadly Pleiotropic Phenotypes Caused by an hfq Insertion Mutation in *Escherichia coli* K-12" Molecular Microbiology 1994 13(1): 35-49.

Valentin-Hansen, P. et al., "The Bacterial Sm-like Protein Hfq: a Key Player in RNA Transactions" Molecular Microbiology (2004) pp. 1525-1533, vol. 51(6).

Zhang, A. et al., "The Sm-like Hfq Protein Increases OxyS RNA Interaction with Target mRNAs" Molecular Cell (2002) pp. 11-22, vol. 9.

Zhang, A. et al., "Global Analysis of Mall RNA and mRNA Targets of Hfq" Molecular Microbiology (2003) pp. 1111-1124, vol. 50(4).

Yang, S. et al., "Transcriptomic and Metabolomic Profiling of *Zymomonas mobilis* During Aerobic and Anaerobic Fermentations" BMC Genomics (2009) pp. 1-16, vol. 10(34).

May 3, 2009 PowerPoint Presentation on "Do Systems Biology Tools Add Value to Strain Development?" U.S. Department of Energy, 31st Symposium on Biotechnology for Fules and Chemicals.

Poster Presentation dated May 3-6, 2009 on "*Zymomonas mobilis* Systems Biology Studies to Elucidate Process Relevant Inhibitor Stress Responses and Tolerance Mechanisms" ™ 8706, Oak Ridge National Laboratory.

* cited by examiner

```
Anaerocellum_thermophilum         ---MAKGSLNLQDLFLNQLRKEKVNVTIFLLSGFQLKGVIKGFDNFTLIVE  48
Caldicellulosiruptor_saccharol    ---MAKGNLNLQDLFLNQLRKEKVNVTIFLLSGFQLKGVIKGFDNFTLVVE  48
Clostridium_thermocellum          MVS-KNNINLQDVFLNQVRKEHIPVTVYLTNGFQLKGTVKGFDNFTVVLD   49
Thermoanaerobacter_sp._X514       MASSKAAINLQDIFLNQVRKEHVPVTVYLINGFQLKGLVKGFDNFTVVLE   50
Zymomonas_mobilis_ZM4             ---MAEKVNNLQDFFLNTLRKTRTPVTMFLVKGVKLQGVITWFDNFSILLR  48
Escherichia_coli_K12              ---MAKGQS-LQDPFLNALRRERVPSIYLVNGIKLQGQIESFDQFVILLK   47
                                         *:    *:*::* .: *::::  :   : :      :::

Anaerocellum_thermophilum         TDNNKQQLIYKHAISSIMPSKP--------INYMAQA               77
Caldicellulosiruptor_saccharol    TENNKQQLIYKHAISSILPSKP--------INYMAQV               77
Clostridium_thermocellum          SEGRQQ--LIYKHAISTISPMK--------IVSLIF                75
Thermoanaerobacter_sp._X514       SENKQQLLIYKHAISTITPQKP--------VIFSASD               79
Zymomonas_mobilis_ZM4             RDGQSQ-LVYKHAISTIIPAHPIEQLRESRSIMAERKSSLLQDVFLSAIM  97
Escherichia_coli_K12              ---NTVSQMVYKHAISTVVPSRP--------VSHHS                72
                                         ::*******::  *  :

Anaerocellum_thermophilum         QNNQ----QASQQSNNNQG----             92
Caldicellulosiruptor_saccharol    QNSQVQNTASQQSNNNQESK----            99
Clostridium_thermocellum          NDNN----RSE------------             82
Thermoanaerobacter_sp._X514       KDEK----REE------------             86
Zymomonas_mobilis_ZM4             QQQEPVTMFLINGVMLQGEIAAFDLFCVLLTRNDDAQLVYKHAVSTVQPV147
Escherichia_coli_K12              NNAG----GGTSSNYHHGSSAQN-            98
                                  ::

Anaerocellum_thermophilum         -----
Caldicellulosiruptor_saccharol    -----
Clostridium_thermocellum          -----
Thermoanaerobacter_sp._X514       -----
Zymomonas_mobilis_ZM4             KSVDLTMTERRDED  161
Escherichia_coli_K12              EETE           102
```

Fig. 1E

SEQUENCE LISTING

<160> NUMBER OF SEQ ID NOS: 56

<210> SEQ ID NO 1
<211> LENGTH: 486
<212> TYPE: DNA
<213> ORGANISM: Zymomonas mobilis

<400> SEQUENCE: 1

```
atggccgaaa aggtcaacaa tcttcaggat tttttcctta ataccttgcg caagacccgc      60
acaccggtga cgatgttttt ggtaaaaggt gtcaaattac agggcgttat cacctggttt     120
gacaattttt ctattctgct gcggagagat ggtcagtcac agctggtcta taaacacgct     180
atttctacca ttattccggc gcatccgctg gaacagctgc gcgaaagccg cagtttgatg     240
gctgaacgta aatccagttt gcttcaggat gtcttttat cggcgattat gcagcagcaa     300
```

```
gaaccggtga caatgttttt gataaacggg gtcatgttgc aaggtgaaat tgccgccttc    360
gatttattct gcgtcttgtt gacccgtaat gacgacgcgc agctggttta taaacatgcg    420
gtttcaacag tgcagcctgt gaaatctgta gatttgacaa tgacagaaag gcgagacgag    480
gattga                                                               486
```

<210> SEQ ID NO 2
<211> LENGTH: 161
<212> TYPE: PRT
<213> ORGANISM: Zymomonas mobilis

<400> SEQUENCE: 2

```
Met Ala Glu Lys Val Asn Asn Leu Gln Asp Phe Phe Leu Asn Thr Leu
1               5                   10                  15

Arg Lys Thr Arg Thr Pro Val Thr Met Phe Leu Val Lys Gly Val Lys
            20                  25                  30

Leu Gln Gly Val Ile Thr Trp Phe Asp Asn Phe Ser Ile Leu Leu Arg
        35                  40                  45

Arg Asp Gly Gln Ser Gln Leu Val Tyr Lys His Ala Ile Ser Thr Ile
    50                  55                  60

Ile Pro Ala His Pro Leu Glu Gln Leu Arg Glu Ser Arg Ser Leu Met
65                  70                  75                  80

Ala Glu Arg Lys Ser Ser Leu Leu Gln Asp Val Phe Leu Ser Ala Ile
                85                  90                  95

Met Gln Gln Gln Glu Pro Val Thr Met Phe Leu Ile Asn Gly Val Met
            100                 105                 110

Leu Gln Gly Glu Ile Ala Ala Phe Asp Leu Phe Cys Val Leu Leu Thr
        115                 120                 125

Arg Asn Asp Asp Ala Gln Leu Val Tyr Lys His Ala Val Ser Thr Val
    130                 135                 140

Gln Pro Val Lys Ser Val Asp Leu Thr Met Thr Glu Arg Arg Asp Glu
145                 150                 155                 160

Asp
```

<210> SEQ ID NO 3
<211> LENGTH: 309
<212> TYPE: DNA
<213> ORGANISM: Escherichia coli

<400> SEQUENCE: 3

```
atggctaagg gcaatctttt acaagatccg ttcctgaacg cactgcgtcg ggaacgtgtt     60
ccagtttcta tttatttggt gaatggtatt aagctgcaag gcaaatcga gtcttttgat    120 cagttcgtga tcctgttgaa aaacacggtc agccagatgt tttacaagca cgcgatttct    180
actgttgtcc cgtctcgccc ggtttctcat acagtaaca acgccggtgg cggtaccagc    240
agtaactacc atcatggtag cagcgcgcag aatacttccg cgcaacagga cagcgaagaa    300
accgaataa                                                           309
```

<210> SEQ ID NO 4
<211> LENGTH: 102
<212> TYPE: PRT
<213> ORGANISM: Escherichia coli

<400> SEQUENCE: 4

```
Met Ala Lys Gly Gln Ser Leu Gln Asp Pro Phe Leu Asn Ala Leu Arg
1               5                   10                  15
```

Arg Glu Arg Val Pro Val Ser Ile Tyr Leu Val Asn Gly Ile Lys Leu
            20                  25                  30

Gln Gly Gln Ile Glu Ser Phe Asp Gln Phe Val Ile Leu Leu Lys Asn
        35                  40                  45

Thr Val Ser Gln Met Val Tyr Lys His Ala Ile Ser Thr Val Val Pro
    50                  55                  60

Ser Arg Pro Val Ser His His Ser Asn Asn Ala Gly Gly Gly Thr Ser
65                  70                  75                  80

Ser Asn Tyr His His Gly Ser Ser Ala Gln Asn Thr Ser Ala Gln Gln
                85                  90                  95

Asp Ser Glu Glu Thr Glu
            100

<210> SEQ ID NO 5
<211> LENGTH: 249
<212> TYPE: DNA
<213> ORGANISM: Clostridium thermoalcaliphilum

<400> SEQUENCE: 5
gtggtgagca aaataatat taatttacag gacgtttttc taaaccaggt aagaaaagaa    60
catattccgg ttactgttta tcttaccaac ggattccagt taaaggaac ggtaaaggga    120 tttgacaatt ttaccgttgt gcttgacagt gagggaaggc agcagctgat ttataaacat    180
gcaatttcaa caataagccc catgaaaatt gttagcttga ttttcaacga caataacaga    240
tcggaataa                                                           249

<210> SEQ ID NO 6
<211> LENGTH: 82
<212> TYPE: PRT
<213> ORGANISM: Clostridium thermoalcaliphilum

<400> SEQUENCE: 6

Met Val Ser Lys Asn Asn Ile Asn Leu Gln Asp Val Phe Leu Asn Gln
1               5                   10                  15

Val Arg Lys Glu His Ile Pro Val Thr Val Tyr Leu Thr Asn Gly Phe
            20                  25                  30

Gln Leu Lys Gly Thr Val Lys Gly Phe Asp Asn Phe Thr Val Val Leu
        35                  40                  45

Asp Ser Glu Gly Arg Gln Gln Leu Ile Tyr Lys His Ala Ile Ser Thr
    50                  55                  60

Ile Ser Pro Met Lys Ile Val Ser Leu Ile Phe Asn Asp Asn Asn Arg
65                  70                  75                  80

Ser Glu

<210> SEQ ID NO 7
<211> LENGTH: 279
<212> TYPE: DNA
<213> ORGANISM: Anaerocellum thermophilum

<400> SEQUENCE: 7
gtggcgaaag gaagtttaaa cttgcaggac ttatttttaa atcagttaag aaaagaaaaa    60
gtgaatgtta caattttct gctcagcggt tttcagttaa aaggagttat caagggtttt    120
gataacttta cattgattgt agagactgac aataacaagc agcaactaat ttacaagcac    180
gctatatctt caatcatgcc ctcaaagcca ataaactata tggctcaggc acagaataat    240
caacaagctt ctcaacaatc aaataataat caaggttaa                          279

<210> SEQ ID NO 8
<211> LENGTH: 92
<212> TYPE: PRT
<213> ORGANISM: Anaerocellum thermophilum

<400> SEQUENCE: 8

Met Ala Lys Gly Ser Leu Asn Leu Gln Asp Leu Phe Leu Asn Gln Leu
1               5                   10                  15

Arg Lys Glu Lys Val Asn Val Thr Ile Phe Leu Leu Ser Gly Phe Gln
            20                  25                  30

Leu Lys Gly Val Ile Lys Gly Phe Asp Asn Phe Thr Leu Ile Val Glu
        35                  40                  45

Thr Asp Asn Asn Lys Gln Gln Leu Ile Tyr Lys His Ala Ile Ser Ser
    50                  55                  60

Ile Met Pro Ser Lys Pro Ile Asn Tyr Met Ala Gln Ala Gln Asn Asn
65                  70                  75                  80

Gln Gln Ala Ser Gln Gln Ser Asn Asn Asn Gln Gly
                85                  90

<210> SEQ ID NO 9
<211> LENGTH: 300
<212> TYPE: DNA
<213> ORGANISM: Caldicellulosiruptor saccharolyticus

<400> SEQUENCE: 9
gtggcaaaag gaaatttgaa cttgcaggat ttattttaa accagcttcg aaaagaaaaa      60
gtcaacgtta caatctttt actgagcgga ttccaattga aaggagttat caaaggtttt     120
gataacttta cattggtggt agagacagaa aataacaaac agcagctcat ttacaaacat    180
gcaatttctt ctattctacc atcaaagcca ataaactaca tggctcaagt tcaaaactca    240
caagtgcaaa acacagcttc tcagcaaagt aacaataacc aaaatcaaga gtcaaaataa    300

<210> SEQ ID NO 10
<211> LENGTH: 99
<212> TYPE: PRT
<213> ORGANISM: Caldicellulosiruptor saccharolyticus

<400> SEQUENCE: 10

Val Ala Lys Gly Asn Leu Asn Leu Gln Asp Leu Phe Leu Asn Gln Leu
1               5                   10                  15

Arg Lys Glu Lys Val Asn Val Thr Ile Phe Leu Leu Ser Gly Phe Gln
            20                  25                  30

Leu Lys Gly Val Ile Lys Gly Phe Asp Asn Phe Thr Leu Val Val Glu
        35                  40                  45

Thr Glu Asn Asn Lys Gln Gln Leu Ile Tyr Lys His Ala Ile Ser Ser
    50                  55                  60

Ile Leu Pro Ser Lys Pro Ile Asn Tyr Met Ala Gln Val Gln Asn Ser
65                  70                  75                  80

Gln Val Gln Asn Thr Ala Ser Gln Gln Ser Asn Asn Asn Gln Asn Gln
                85                  90                  95

Glu Ser Lys

<210> SEQ ID NO 11
<211> LENGTH: 261
<212> TYPE: DNA
<213> ORGANISM: Thermoanaerobacter sp.

<400> SEQUENCE: 11

```
atggcaagtt caaaagcagc tattaattta caggatatct ttttaaatca agtgaggaaa      60
gagcatgtac cagtaactgt ctacttaatc aacggatttc aattaaaggg tttagtgaaa     120
ggatttgata attttacagt ggtgttggag tcagagaaca acagcaact tcttatctac      180
aaacatgcta tttcgacaat tacacctcaa aagcctgtga tcttctctgc ttctgataaa     240
gatgagaaga gagaagagtg a                                                261
```

<210> SEQ ID NO 12
<211> LENGTH: 86
<212> TYPE: PRT
<213> ORGANISM: Thermoanaerobacter sp.

<400> SEQUENCE: 12

```
Met Ala Ser Ser Lys Ala Ala Ile Asn Leu Gln Asp Ile Phe Leu Asn
1               5                   10                  15
Gln Val Arg Lys Glu His Val Pro Val Thr Val Tyr Leu Ile Asn Gly
            20                  25                  30
Phe Gln Leu Lys Gly Leu Val Lys Gly Phe Asp Asn Phe Thr Val Val
        35                  40                  45
Leu Glu Ser Glu Asn Lys Gln Gln Leu Leu Ile Tyr Lys His Ala Ile
    50                  55                  60
Ser Thr Ile Thr Pro Gln Lys Pro Val Ile Phe Ser Ala Ser Asp Lys
65                  70                  75                  80
Asp Glu Lys Arg Glu Glu
                85
```

<210> SEQ ID NO 13
<211> LENGTH: 591
<212> TYPE: DNA
<213> ORGANISM: Saccharomyces cerevisiae

<400> SEQUENCE: 13

```
atgagcaaaa tacaggtggc acatagcagc cgactagcca accttattga ttataagctg      60
agggttctca ctcaagatgg ccgcgtttac atcgggcaat tgatggcatt tgataaacat     120
atgaattag tgttgaatga gtgtatagaa gagagggtac ccaaaactca actagataaa      180
ttaagaccga gaaagattc aaaagatgga accactttga acatcaaggt agaaaaaaga     240
gtgttgggac tgactatact aagaggagaa cagatcttat ccacagtggt ggaggataag     300
ccgctactat ccaagaagga agactagtg agagataaaa aggaaaagaa acaagcgcaa     360
aagcagacga aactaagaaa agagaaagag aaaaagccgg gaaagatcgc taaacctaac     420
acggccaatg cgaagcatac tagtagcaat tctagggaga ttgcccaacc atcgtcgagc     480
agatacaatg gtggcaacga taatatcggc gcaaataggt cgaggtttaa taatgaagcg     540
ccccctcaaa caaggaagtt tcagccccca ccaggttta aagaaaata a                591
```

<210> SEQ ID NO 14
<211> LENGTH: 196
<212> TYPE: PRT
<213> ORGANISM: Saccharomyces cerevisiae

<400> SEQUENCE: 14

```
Met Ser Lys Ile Gln Val Ala His Ser Ser Arg Leu Ala Asn Leu Ile
1               5                   10                  15
Asp Tyr Lys Leu Arg Val Leu Thr Gln Asp Gly Arg Val Tyr Ile Gly
            20                  25                  30
```

```
Gln Leu Met Ala Phe Asp Lys His Met Asn Leu Val Leu Asn Glu Cys
            35                  40                  45

Ile Glu Glu Arg Val Pro Lys Thr Gln Leu Asp Lys Leu Arg Pro Arg
 50                  55                  60

Lys Asp Ser Lys Asp Gly Thr Thr Leu Asn Ile Lys Val Glu Lys Arg
 65                  70                  75                  80

Val Leu Gly Leu Thr Ile Leu Arg Gly Glu Gln Ile Leu Ser Thr Val
                85                  90                  95

Val Glu Asp Lys Pro Leu Leu Ser Lys Glu Arg Leu Val Arg Asp
                100                 105                 110

Lys Lys Glu Lys Lys Gln Ala Gln Lys Gln Thr Lys Leu Arg Lys Glu
                115                 120                 125

Lys Glu Lys Lys Pro Gly Lys Ile Ala Lys Pro Asn Thr Ala Asn Ala
 130                 135                 140

Lys His Thr Ser Ser Asn Ser Arg Glu Ile Ala Gln Pro Ser Ser Ser
145                 150                 155                 160

Arg Tyr Asn Gly Gly Asn Asp Asn Ile Gly Ala Asn Arg Ser Arg Phe
                165                 170                 175

Asn Asn Glu Ala Pro Pro Gln Thr Arg Lys Phe Gln Pro Pro Pro Gly
                180                 185                 190

Phe Lys Arg Lys
        195

<210> SEQ ID NO 15
<211> LENGTH: 441
<212> TYPE: DNA
<213> ORGANISM: Saccharomyces cerevisiae

<400> SEQUENCE: 15
atgaagttgg ttaactttt aaaaaagctg cgcaatgagc aggttaccat agaactaaaa      60
aacggtacca ccgtttgggg tacactgcag tcggtatcac cacaaatgaa tgctatctta     120
actgacgtga agttgaccct accacaaccc cgactaaata aattgaacag taatggtatt     180
gcgatggcta gtctgtactt gactggagga cagcaaccta ctgcaagtga acacatagca     240
agtttgcaat acataaacat tagaggcaat accataagac agataatctt acctgattcc     300
ttgaacctgg attcactttt ggttgaccaa aagcaactta ttccctaag  aagatcgggt     360 caaattgcaa atgaccccag caaaaagaga aggcgcgatt ttggtgcacc agcgaataaa     420
aggccaagaa gaggtctatg a                                               441

<210> SEQ ID NO 16
<211> LENGTH: 146
<212> TYPE: PRT
<213> ORGANISM: Saccharomyces cerevisiae

<400> SEQUENCE: 16

Met Lys Leu Val Asn Phe Leu Lys Lys Leu Arg Asn Glu Gln Val Thr
  1               5                  10                  15

Ile Glu Leu Lys Asn Gly Thr Thr Val Trp Gly Thr Leu Gln Ser Val
                 20                  25                  30

Ser Pro Gln Met Asn Ala Ile Leu Thr Asp Val Lys Leu Thr Leu Pro
             35                  40                  45

Gln Pro Arg Leu Asn Lys Leu Asn Ser Asn Gly Ile Ala Met Ala Ser
 50                  55                  60

Leu Tyr Leu Thr Gly Gly Gln Gln Pro Thr Ala Ser Asp Asn Ile Ala
```

```
                    65                  70                  75                  80
Ser Leu Gln Tyr Ile Asn Ile Arg Gly Asn Thr Ile Arg Gln Ile Ile
                        85                  90                  95

Leu Pro Asp Ser Leu Asn Leu Asp Ser Leu Val Asp Gln Lys Gln
                100                 105                 110

Leu Asn Ser Leu Arg Arg Ser Gly Gln Ile Ala Asn Asp Pro Ser Lys
            115                 120                 125

Lys Arg Arg Arg Asp Phe Gly Ala Pro Ala Asn Lys Arg Pro Arg Arg
        130                 135                 140

Gly Leu
145

<210> SEQ ID NO 17
<211> LENGTH: 333
<212> TYPE: DNA
<213> ORGANISM: Saccharomyces cerevisiae

<400> SEQUENCE: 17
atgtcttcac aaataattga tcgtccaaaa catgaactct ctagagcaga attagaggaa      60
ctagaagaat tgaattcaa acatggtcca atgtccctga taaatgatgc tatggtgaca     120
agaacacctg tgataatctc attaagaaac aatcataaaa taatagcgag agtgaaagct    180
ttcgacaggc attgtaatat ggttttagaa aatgtgaagg agctttggac agagaagaag    240
ggcaaaaatg taattaatcg ggaaagattc ataagtaaac tattcttaag aggtgattca    300
gttatcgttg tgttaaaaac ccctgttgag taa                                 333

<210> SEQ ID NO 18
<211> LENGTH: 110
<212> TYPE: PRT
<213> ORGANISM: Saccharomyces cerevisiae

<400> SEQUENCE: 18

Met Ser Ser Gln Ile Ile Asp Arg Pro Lys His Glu Leu Ser Arg Ala
1               5                   10                  15

Glu Leu Glu Glu Leu Glu Glu Phe Glu Phe Lys His Gly Pro Met Ser
                20                  25                  30

Leu Ile Asn Asp Ala Met Val Thr Arg Thr Pro Val Ile Ile Ser Leu
            35                  40                  45

Arg Asn Asn His Lys Ile Ile Ala Arg Val Lys Ala Phe Asp Arg His
        50                  55                  60

Cys Asn Met Val Leu Glu Asn Val Lys Glu Leu Trp Thr Glu Lys Lys
65                  70                  75                  80

Gly Lys Asn Val Ile Asn Arg Glu Arg Phe Ile Ser Lys Leu Phe Leu
                85                  90                  95

Arg Gly Asp Ser Val Ile Val Val Leu Lys Thr Pro Val Glu
            100                 105                 110

<210> SEQ ID NO 19
<211> LENGTH: 306
<212> TYPE: DNA
<213> ORGANISM: Saccharomyces cerevisiae

<400> SEQUENCE: 19
atgactatga atggaatacc agtgaaatta ttaaatgagg cacagggaca tatcgtttct      60
ctggagctaa caacgggagc gacttatcgt ggtaaacttg ttgaaagcga agatagcatg    120
aacgtacagc taagagatgt aatagctaca gagccccagg gggctgtaac acacatggat    180
```

```
caaatattcg tacgtgggtc acagatcaaa tttatcgttg ttccagatct cttaaagaat    240
gcaccattat tcaaaaaaaa ctcatcaaga cctatgccac caataagagg acctaagaga    300
aggtga                                                               306
```

<210> SEQ ID NO 20
<211> LENGTH: 101
<212> TYPE: PRT
<213> ORGANISM: Saccharomyces cerevisiae

<400> SEQUENCE: 20

```
Met Thr Met Asn Gly Ile Pro Val Lys Leu Leu Asn Glu Ala Gln Gly
 1               5                  10                  15

His Ile Val Ser Leu Glu Leu Thr Thr Gly Ala Thr Tyr Arg Gly Lys
                20                  25                  30

Leu Val Glu Ser Glu Asp Ser Met Asn Val Gln Leu Arg Asp Val Ile
            35                  40                  45

Ala Thr Glu Pro Gln Gly Ala Val Thr His Met Asp Gln Ile Phe Val
        50                  55                  60

Arg Gly Ser Gln Ile Lys Phe Ile Val Val Pro Asp Leu Leu Lys Asn
    65                  70                  75                  80

Ala Pro Leu Phe Lys Lys Asn Ser Ser Arg Pro Met Pro Pro Ile Arg
                85                  90                  95

Gly Pro Lys Arg Arg
            100
```

<210> SEQ ID NO 21
<211> LENGTH: 285
<212> TYPE: DNA
<213> ORGANISM: Saccharomyces cerevisiae

<400> SEQUENCE: 21

```
atgtcgaaca agttaaaaac caaggccatg gtgccaccaa taaattgcat atttaacttc     60
ttacaacagc aaacaccagt aacgatatgg ttattcgagc aaatcggcat aagaatcaag    120
ggtaaaatag ttggatttga tgagttcatg aatgttgtca tcgatgaagc cgtggaaatt    180
cctgtgaata gtgccgatgg taaagaagat gtggagaagg gcacgccctt ggggaagatc    240
ctgttgaaag gcgataatat cacattgata acatcagcgg actga                   285
```

<210> SEQ ID NO 22
<211> LENGTH: 94
<212> TYPE: PRT
<213> ORGANISM: Saccharomyces cerevisiae

<400> SEQUENCE: 22

```
Met Ser Asn Lys Val Lys Thr Lys Ala Met Val Pro Pro Ile Asn Cys
 1               5                  10                  15

Ile Phe Asn Phe Leu Gln Gln Gln Thr Pro Val Thr Ile Trp Leu Phe
                20                  25                  30

Glu Gln Ile Gly Ile Arg Ile Lys Gly Lys Ile Val Gly Phe Asp Glu
            35                  40                  45

Phe Met Asn Val Val Ile Asp Glu Ala Val Glu Ile Pro Val Asn Ser
        50                  55                  60

Ala Asp Gly Lys Glu Asp Val Glu Lys Gly Thr Pro Leu Gly Lys Ile
    65                  70                  75                  80

Leu Leu Lys Gly Asp Asn Ile Thr Leu Ile Thr Ser Ala Asp
                85                  90
```

<210> SEQ ID NO 23
<211> LENGTH: 261
<212> TYPE: DNA
<213> ORGANISM: Saccharomyces cerevisiae

<400> SEQUENCE: 23

```
atgagcgaga gcagtgatat cagcgcgatg cagccggtga acccgaagcc gttcctcaaa      60
ggcctggtca accatcgtgt aggcgtcaag cttaagttca acagcaccga atatagaggt     120
acgctcgtgt ccacggacaa ctactttaac ctgcagctga acgaagcaga agagtttgtt     180
gcgggtgtct cgcacggcac cctgggcgag atattcatcc gctgcaataa cgtgctgtac     240
atcagggagc tgccgaacta a                                               261
```

<210> SEQ ID NO 24
<211> LENGTH: 86
<212> TYPE: PRT
<213> ORGANISM: Saccharomyces cerevisiae

<400> SEQUENCE: 24

```
Met Ser Glu Ser Ser Asp Ile Ser Ala Met Gln Pro Val Asn Pro Lys
1               5                  10                  15

Pro Phe Leu Lys Gly Leu Val Asn His Arg Val Gly Val Lys Leu Lys
            20                  25                  30

Phe Asn Ser Thr Glu Tyr Arg Gly Thr Leu Val Ser Thr Asp Asn Tyr
        35                  40                  45

Phe Asn Leu Gln Leu Asn Glu Ala Glu Glu Phe Val Ala Gly Val Ser
    50                  55                  60

His Gly Thr Leu Gly Glu Ile Phe Ile Arg Cys Asn Asn Val Leu Tyr
65                  70                  75                  80

Ile Arg Glu Leu Pro Asn
                85
```

<210> SEQ ID NO 25
<211> LENGTH: 234
<212> TYPE: DNA
<213> ORGANISM: Saccharomyces cerevisiae

<400> SEQUENCE: 25

```
atggtttcta cccctgaact gaagaaatat atggacaaga agatattgct gaatataaat      60
ggatctagga aagtggcagg aattttgcga ggctacgata ttttcttaaa cgtcgttctt     120
gatgatgcaa tggagataaa tggtgaagac cctgccaata accaccagct aggcttgcag     180
accgtcatta gggcaactc cataatatcc ctagaggctc tagatgccat ataa            234
```

<210> SEQ ID NO 26
<211> LENGTH: 77
<212> TYPE: PRT
<213> ORGANISM: Saccharomyces cerevisiae

<400> SEQUENCE: 26

```
Met Val Ser Thr Pro Glu Leu Lys Lys Tyr Met Asp Lys Lys Ile Leu
1               5                  10                  15

Leu Asn Ile Asn Gly Ser Arg Lys Val Ala Gly Ile Leu Arg Gly Tyr
            20                  25                  30

Asp Ile Phe Leu Asn Val Val Leu Asp Asp Ala Met Glu Ile Asn Gly
        35                  40                  45

Glu Asp Pro Ala Asn Asn His Gln Leu Gly Leu Gln Thr Val Ile Arg
```

Gly Asn Ser Ile Ile Ser Leu Glu Ala Leu Asp Ala Ile
65                  70                  75

<210> SEQ ID NO 27
<211> LENGTH: 519
<212> TYPE: DNA
<213> ORGANISM: Saccharomyces cerevisiae

<400> SEQUENCE: 27

```
atgtctgcaa atagcaagga cagaaatcag tccaatcagg atgcgaagcg acaacagcag    60
aatttcccaa agaagatttc agaaggtgag gccgatttat atctcgacca gtataacttc   120
actaccaccg ctgctattgt aagctcagta gaccgtaaaa tcttcgttct tttgcgtgat   180
ggaagaatgc tattcggtgt actaagaacc tttgaccaat atgcaaattt gatacttcaa   240
gattgcgtgg agagaatata ttttagcgaa gaaacaaat acgctgaaga agaccgcggc   300
atattcatga ttcgtggtga aaatgttgtc atgttaggcg aagtagacat cgataaagaa   360
gatcaacccc ttgaggccat ggaacgcata ccatttaagg aggcttggct gaccaagcaa   420
aaaaatgatg agaaaaggtt taagaggaa acccacaaag gtaaaaaaat ggcccgccat   480
ggtatcgttt acgatttcca taaatctgac atgtactaa                         519
```

<210> SEQ ID NO 28
<211> LENGTH: 172
<212> TYPE: PRT
<213> ORGANISM: Saccharomyces cerevisiae

<400> SEQUENCE: 28

Met Ser Ala Asn Ser Lys Asp Arg Asn Gln Ser Asn Gln Asp Ala Lys
1               5                   10                  15

Arg Gln Gln Gln Asn Phe Pro Lys Lys Ile Ser Glu Gly Glu Ala Asp
            20                  25                  30

Leu Tyr Leu Asp Gln Tyr Asn Phe Thr Thr Thr Ala Ala Ile Val Ser
        35                  40                  45

Ser Val Asp Arg Lys Ile Phe Val Leu Leu Arg Asp Gly Arg Met Leu
    50                  55                  60

Phe Gly Val Leu Arg Thr Phe Asp Gln Tyr Ala Asn Leu Ile Leu Gln
65                  70                  75                  80

Asp Cys Val Glu Arg Ile Tyr Phe Ser Glu Glu Asn Lys Tyr Ala Glu
                85                  90                  95

Glu Asp Arg Gly Ile Phe Met Ile Arg Gly Glu Asn Val Val Met Leu
            100                 105                 110

Gly Glu Val Asp Ile Asp Lys Glu Asp Gln Pro Leu Glu Ala Met Glu
        115                 120                 125

Arg Ile Pro Phe Lys Glu Ala Trp Leu Thr Lys Gln Lys Asn Asp Glu
    130                 135                 140

Lys Arg Phe Lys Glu Glu Thr His Lys Gly Lys Lys Met Ala Arg His
145                 150                 155                 160

Gly Ile Val Tyr Asp Phe His Lys Ser Asp Met Tyr
                165                 170

<210> SEQ ID NO 29
<211> LENGTH: 288
<212> TYPE: DNA
<213> ORGANISM: Saccharomyces cerevisiae

<400> SEQUENCE: 29

```
atgcttttct tctccttttt caagacttta gttgaccaag aagtggtcgt agagttaaaa    60
aacgacattg aaataaaagg tacactacaa tcagttgacc aattttttgaa tctgaaacta   120 gacaacatat catgcacaga tgaaaaaaaa tatccacact tgggttccgt aaggaatatt   180
tttataagag gttcaacagt caggtacgtt tacttgaata agaacatggt agatacgaat   240
ttgctacaag acgctaccag aagggaggta atgactgaaa gaaaataa                288
```

<210> SEQ ID NO 30
<211> LENGTH: 95
<212> TYPE: PRT
<213> ORGANISM: Saccharomyces cerevisiae

<400> SEQUENCE: 30

Met Leu Phe Phe Ser Phe Phe Lys Thr Leu Val Asp Gln Glu Val Val
1               5                   10                  15

Val Glu Leu Lys Asn Asp Ile Glu Ile Lys Gly Thr Leu Gln Ser Val
                20                  25                  30

Asp Gln Phe Leu Asn Leu Lys Leu Asp Asn Ile Ser Cys Thr Asp Glu
            35                  40                  45

Lys Lys Tyr Pro His Leu Gly Ser Val Arg Asn Ile Phe Ile Arg Gly
        50                  55                  60

Ser Thr Val Arg Tyr Val Tyr Leu Asn Lys Asn Met Val Asp Thr Asn
65                  70                  75                  80

Leu Leu Gln Asp Ala Thr Arg Arg Glu Val Met Thr Glu Arg Lys
                85                  90                  95

<210> SEQ ID NO 31
<211> LENGTH: 270
<212> TYPE: DNA
<213> ORGANISM: Saccharomyces cerevisiae

<400> SEQUENCE: 31

```
atggagacac ctttggattt attgaaactc aatctcgatg agagggtgta catcaagctg    60
cgcggggcca ggacgctggt gggcacactg caagcgttcg actcacactg caacatcgtg   120
ctgagtgatg cagtagagac catataccaa ttaaacaacg aggagttgag tgagtccgaa   180
agacgatgtg aaatggtgtt catcagagga gacacagtga ctctaatcag cacgccctct   240
gaagatgacg atggcgcagt ggagatataa                                    270
```

<210> SEQ ID NO 32
<211> LENGTH: 89
<212> TYPE: PRT
<213> ORGANISM: Saccharomyces cerevisiae

<400> SEQUENCE: 32

Met Glu Thr Pro Leu Asp Leu Leu Lys Leu Asn Leu Asp Glu Arg Val
1               5                   10                  15

Tyr Ile Lys Leu Arg Gly Ala Arg Thr Leu Val Gly Thr Leu Gln Ala
                20                  25                  30

Phe Asp Ser His Cys Asn Ile Val Leu Ser Asp Ala Val Glu Thr Ile
            35                  40                  45

Tyr Gln Leu Asn Asn Glu Glu Leu Ser Glu Ser Glu Arg Arg Cys Glu
        50                  55                  60

Met Val Phe Ile Arg Gly Asp Thr Val Thr Leu Ile Ser Thr Pro Ser
65                  70                  75                  80

Glu Asp Asp Asp Gly Ala Val Glu Ile
                85

```
<210> SEQ ID NO 33
<211> LENGTH: 564
<212> TYPE: DNA
<213> ORGANISM: Saccharomyces cerevisiae

<400> SEQUENCE: 33
atgctacctt tatatctttt aacaaatgcg aagggacaac aaatgcaaat agaattgaaa      60
aacggtgaaa ttatacaagg gatattgacc aacgtagata actggatgaa ccttactta     120 tctaatgtaa ccgaatatag tgaagaaagc gcaattaatt cagaagacaa tgctgagagc    180
agtaaagccg taaaattgaa cgaaatttat attagaggga cttttatcaa gtttatcaaa    240
ttgcaagata atataattga caaggtcaag cagcaaatta actccaacaa taactctaat    300
agtaacggcc ctgggcataa aagatactac aacaataggg attcaaacaa caatagaggt    360
aactacaaca gaagaaataa taataacggc aacagcaacc gccgtccata ctctcaaaac    420
cgtcaataca acaacagcaa cagcagtaac attaacaaca gtatcaacag tatcaatagc    480
aacaaccaaa atatgaacaa tggtttaggt gggtccgtcc aacatcattt taacagctct    540
tctccacaaa aggtcgaatt ttaa                                            564

<210> SEQ ID NO 34
<211> LENGTH: 187
<212> TYPE: PRT
<213> ORGANISM: Saccharomyces cerevisiae

<400> SEQUENCE: 34

Met Leu Pro Leu Tyr Leu Leu Thr Asn Ala Lys Gly Gln Gln Met Gln
1               5                   10                  15

Ile Glu Leu Lys Asn Gly Glu Ile Ile Gln Gly Ile Leu Thr Asn Val
            20                  25                  30

Asp Asn Trp Met Asn Leu Thr Leu Ser Asn Val Thr Glu Tyr Ser Glu
        35                  40                  45

Glu Ser Ala Ile Asn Ser Glu Asp Asn Ala Glu Ser Ser Lys Ala Val
    50                  55                  60

Lys Leu Asn Glu Ile Tyr Ile Arg Gly Thr Phe Ile Lys Phe Ile Lys
65                  70                  75                  80

Leu Gln Asp Asn Ile Ile Asp Lys Val Lys Gln Gln Ile Asn Ser Asn
                85                  90                  95

Asn Asn Ser Asn Ser Asn Gly Pro Gly His Lys Arg Tyr Tyr Asn Asn
            100                 105                 110

Arg Asp Ser Asn Asn Asn Arg Gly Asn Tyr Asn Arg Arg Asn Asn Asn
        115                 120                 125

Asn Gly Asn Ser Asn Arg Arg Pro Tyr Ser Gln Asn Arg Gln Tyr Asn
    130                 135                 140

Asn Ser Asn Ser Ser Asn Ile Asn Asn Ser Ile Asn Ser Ile Asn Ser
145                 150                 155                 160

Asn Asn Gln Asn Met Asn Asn Gly Leu Gly Gly Ser Val Gln His His
                165                 170                 175

Phe Asn Ser Ser Ser Pro Gln Lys Val Glu Phe
            180                 185

<210> SEQ ID NO 35
<211> LENGTH: 282
<212> TYPE: DNA
<213> ORGANISM: Saccharomyces cerevisiae
```

<400> SEQUENCE: 35

```
atgagtctac cggagatttt gcctttggaa gtcatagata aacaattaa ccagaaagtg       60 ttgattgtgc tgcagtcgaa ccgcgagttc gagggcacgt tagttggttt cgacgacttc      120
gtcaacgtta tactggaaga cgctgtcgag tggcttatcg atcctgagga cgagagcaga      180
aatgagaaag ttatgcagca ccatggcaga atgcttttaa gcggcaacaa tattgccatc      240
cttgtgccag gcggcaaaaa gaccsctacg gaggcgttgt aa                         282
```

<210> SEQ ID NO 36
<211> LENGTH: 93
<212> TYPE: PRT
<213> ORGANISM: Saccharomyces cerevisiae

<400> SEQUENCE: 36

```
Met Ser Leu Pro Glu Ile Leu Pro Leu Glu Val Ile Asp Lys Thr Ile
1               5                   10                  15

Asn Gln Lys Val Leu Ile Val Leu Gln Ser Asn Arg Glu Phe Glu Gly
            20                  25                  30

Thr Leu Val Gly Phe Asp Asp Phe Val Asn Val Ile Leu Glu Asp Ala
        35                  40                  45

Val Glu Trp Leu Ile Asp Pro Glu Asp Glu Ser Arg Asn Glu Lys Val
    50                  55                  60

Met Gln His His Gly Arg Met Leu Leu Ser Gly Asn Asn Ile Ala Ile
65                  70                  75                  80

Leu Val Pro Gly Gly Lys Lys Thr Pro Thr Glu Ala Leu
                85                  90
```

<210> SEQ ID NO 37
<211> LENGTH: 261
<212> TYPE: DNA
<213> ORGANISM: Saccharomyces cerevisiae

<400> SEQUENCE: 37

```
atgtccggaa aagcttctac agagggtagc gttactacgg agtttctctc tgatatcatt       60
ggtaagacag tgaacgtcaa acttgcctcg ggtttactct acagcggaag attggaatcc      120
attgatggtt ttatgaatgt tgcactatcg agtgccactg aacactacga gagtaataac      180
aataagcttc taaataagtt caatagtgat gtcttttga ggggcacgca ggtcatgtat       240
atcagtgaac aaaaaatata g                                                261
```

<210> SEQ ID NO 38
<211> LENGTH: 86
<212> TYPE: PRT
<213> ORGANISM: Saccharomyces cerevisiae

<400> SEQUENCE: 38

```
Met Ser Gly Lys Ala Ser Thr Glu Gly Ser Val Thr Thr Glu Phe Leu
1               5                   10                  15

Ser Asp Ile Ile Gly Lys Thr Val Asn Val Lys Leu Ala Ser Gly Leu
            20                  25                  30

Leu Tyr Ser Gly Arg Leu Glu Ser Ile Asp Gly Phe Met Asn Val Ala
        35                  40                  45

Leu Ser Ser Ala Thr Glu His Tyr Glu Ser Asn Asn Lys Leu Leu
    50                  55                  60

Asn Lys Phe Asn Ser Asp Val Phe Leu Arg Gly Thr Gln Val Met Tyr
65                  70                  75                  80
```

<210> SEQ ID NO 39
<211> LENGTH: 348
<212> TYPE: DNA
<213> ORGANISM: Saccharomyces cerevisiae

<400> SEQUENCE: 39

```
atgcatcagc aacactccaa atcagagaac aaaccacaac agcaaaggaa aaaattcgaa      60
ggccctaaaa gagaagctat tctggattta gcgaagtata agattctaa aattcgcgtc     120
aaattaatgg gtggtaaatt agttataggt gtcctaaaag gctatgatca actgatgaac    180
ttggtacttg atgatacagt agaatatatg tctaatcctg atgatgaaaa caacactgaa    240
ctgatttcta aaaacgcaag aaagctaggt ttgaccgtca taagaggtac tatttttggtc   300
tctttaagtt ccgccgaagg ttctgatgta ctatatatgc aaaaatag                 348
```

<210> SEQ ID NO 40
<211> LENGTH: 115
<212> TYPE: PRT
<213> ORGANISM: Saccharomyces cerevisiae

<400> SEQUENCE: 40

Met His Gln Gln His Ser Lys Ser Glu Asn Lys Pro Gln Gln Arg
1               5                   10                  15

Lys Lys Phe Glu Gly Pro Lys Arg Glu Ala Ile Leu Asp Leu Ala Lys
            20                  25                  30

Tyr Lys Asp Ser Lys Ile Arg Val Lys Leu Met Gly Gly Lys Leu Val
        35                  40                  45

Ile Gly Val Leu Lys Gly Tyr Asp Gln Leu Met Asn Leu Val Leu Asp
    50                  55                  60

Asp Thr Val Glu Tyr Met Ser Asn Pro Asp Asp Glu Asn Asn Thr Glu
65                  70                  75                  80

Leu Ile Ser Lys Asn Ala Arg Lys Leu Gly Leu Thr Val Ile Arg Gly
                85                  90                  95

Thr Ile Leu Val Ser Leu Ser Ser Ala Glu Gly Ser Asp Val Leu Tyr
            100                 105                 110

Met Gln Lys
        115

<210> SEQ ID NO 41
<211> LENGTH: 330
<212> TYPE: DNA
<213> ORGANISM: Saccharomyces cerevisiae

<400> SEQUENCE: 41

```
atgtcagcca ccttgaaaga ctacttaaat aaaagagttg ttataatcaa agttgacggc      60
gaatgcctca tagcaagcct aaacggcttc gacaaaaata ctaatctatt cataaccaat    120
gttttcaacc gcataagcaa ggaattcatc tgcaaggcac agttacttcg aggcagcgag    180
attgctcttg ttggcctcat agatgcagaa aatgatgaca gtctagctcc tatagacgaa    240
aagaaggtcc caatgctaaa ggacaccaag aataaaatcg aaaatgagca tgtaatatgg    300
gaaaaagtgt acgaatcaaa gacaaaataa                                     330
```

<210> SEQ ID NO 42
<211> LENGTH: 109

<212> TYPE: PRT
<213> ORGANISM: Saccharomyces cerevisiae

<400> SEQUENCE: 42

```
Met Ser Ala Thr Leu Lys Asp Tyr Leu Asn Lys Arg Val Val Ile Ile
1               5                   10                  15

Lys Val Asp Gly Glu Cys Leu Ile Ala Ser Leu Asn Gly Phe Asp Lys
                20                  25                  30

Asn Thr Asn Leu Phe Ile Thr Asn Val Phe Asn Arg Ile Ser Lys Glu
            35                  40                  45

Phe Ile Cys Lys Ala Gln Leu Leu Arg Gly Ser Glu Ile Ala Leu Val
        50                  55                  60

Gly Leu Ile Asp Ala Glu Asn Asp Asp Ser Leu Ala Pro Ile Asp Glu
65                  70                  75                  80

Lys Lys Val Pro Met Leu Lys Asp Thr Lys Asn Lys Ile Glu Asn Glu
                85                  90                  95

His Val Ile Trp Glu Lys Val Tyr Glu Ser Lys Thr Lys
            100                 105
```

<210> SEQ ID NO 43
<211> LENGTH: 267
<212> TYPE: DNA
<213> ORGANISM: Saccharomyces cerevisiae

<400> SEQUENCE: 43

```
atggacatct tgaaactgtc agattttatt ggaaatactt taatagtttc ccttacagaa      60
gatcgtattt tagttggaag cttggttgct gtagatgccc aaatgaattt gctattagat     120
catgttgagg aacgtatggg ctccagtagt agaatgatgg gcctagtcag cgtccctagg     180
cgttccgtta agaccataat gattgataag cctgttctgc aggagcttac tgcgaataaa     240
gttgaattga tggctaatat tgtttag                                         267
```

<210> SEQ ID NO 44
<211> LENGTH: 88
<212> TYPE: PRT
<213> ORGANISM: Saccharomyces cerevisiae

<400> SEQUENCE: 44

```
Met Asp Ile Leu Lys Leu Ser Asp Phe Ile Gly Asn Thr Leu Ile Val
1               5                   10                  15

Ser Leu Thr Glu Asp Arg Ile Leu Val Gly Ser Leu Val Ala Val Asp
                20                  25                  30

Ala Gln Met Asn Leu Leu Leu Asp His Val Glu Glu Arg Met Gly Ser
            35                  40                  45

Ser Ser Arg Met Met Gly Leu Val Ser Val Pro Arg Arg Ser Val Lys
        50                  55                  60

Thr Ile Met Ile Asp Lys Pro Val Leu Gln Glu Leu Thr Ala Asn Lys
65                  70                  75                  80

Val Glu Leu Met Ala Asn Ile Val
                85
```

<210> SEQ ID NO 45
<211> LENGTH: 564
<212> TYPE: DNA
<213> ORGANISM: Saccharomyces cerevisiae

<400> SEQUENCE: 45

```
atgagtgtca gccttgagca aacgctcgga ttcagaataa aagttacgaa cgtgttggat      60
```

```
gtagttactg aaggaagatt gtattcgttc aattcatcca acaacactct tactatccaa      120
acaacaaaga agaatcaatc tccacaaaac ttcaaggtga taaaatgtac attcatcaag      180
catttggaag tcattggtga taagccctcg tttaactcat tcaaaaagca acaaatcaaa      240
ccctcatatg tcaacgtgga aagagttgag aagcttttga agaaagtgt aatagcatct       300 aaaaagaaag aactcttaag gggcaagggt gtgagtgcag agggtcagtt cattttcgat      360
caaatcttca agaccatagg agatactaag tgggtggcta agacatcat tattcttgat       420 gacgttaagg tgcaacctcc atacaaggtc gaagatatca aagtgctaca tgagggaagt      480
aaccaatcca ttacattaat tcaaagaata gtggaaagaa gctgggagca gctagaacaa      540
gacgatggta ggaaaggtgg atag                                             564

<210> SEQ ID NO 46
<211> LENGTH: 187
<212> TYPE: PRT
<213> ORGANISM: Saccharomyces cerevisiae

<400> SEQUENCE: 46

Met Ser Val Ser Leu Glu Gln Thr Leu Gly Phe Arg Ile Lys Val Thr
1               5                  10                  15

Asn Val Leu Asp Val Val Thr Glu Gly Arg Leu Tyr Ser Phe Asn Ser
            20                  25                  30

Ser Asn Asn Thr Leu Thr Ile Gln Thr Thr Lys Lys Asn Gln Ser Pro
        35                  40                  45

Gln Asn Phe Lys Val Ile Lys Cys Thr Phe Ile Lys His Leu Glu Val
    50                  55                  60

Ile Gly Asp Lys Pro Ser Phe Asn Ser Phe Lys Lys Gln Gln Ile Lys
65                  70                  75                  80

Pro Ser Tyr Val Asn Val Glu Arg Val Glu Lys Leu Leu Lys Glu Ser
                85                  90                  95

Val Ile Ala Ser Lys Lys Lys Glu Leu Leu Arg Gly Lys Gly Val Ser
            100                 105                 110

Ala Glu Gly Gln Phe Ile Phe Asp Gln Ile Phe Lys Thr Ile Gly Asp
        115                 120                 125

Thr Lys Trp Val Ala Lys Asp Ile Ile Ile Leu Asp Asp Val Lys Val
    130                 135                 140

Gln Pro Pro Tyr Lys Val Glu Asp Ile Lys Val Leu His Glu Gly Ser
145                 150                 155                 160

Asn Gln Ser Ile Thr Leu Ile Gln Arg Ile Val Glu Arg Ser Trp Glu
                165                 170                 175

Gln Leu Glu Gln Asp Asp Gly Arg Lys Gly Gly
            180                 185

<210> SEQ ID NO 47
<211> LENGTH: 1050
<212> TYPE: DNA
<213> ORGANISM: Saccharomyces cerevisiae

<400> SEQUENCE: 47
atgtcgcagt acatcggtaa aactatttct ttaatctctg tgactgacaa cagatatgtg       60
gggctgttag aagatattga ctctgaaaag ggtaccgtga ctttgaaaga agttcgctgt      120
tttggtacag aaggtcgcaa gaactggggt cctgaagaaa tttatccgaa tcctacggta      180
tacaattctg taaagttcaa cggcagtgaa gtcaaggatt taagcatttt agatgctaac      240
```

-continued

```
atcaatgaca tacagccggt tgttcctcaa atgatgccac ccgcttcaca attccctcct    300
caacaagctc aatctccacc ccaggctcaa gctcaagcac acgtgcaaac aaacccccaa    360
gttccaaagc ccgaatccaa tgtgccagca gctgtcgctg gatatggtgt ttacacccca    420
acttcgacag aaaccgctac tgctagtatg aatgataaga gcactcctca agacaccaat    480
gtaaactcgc aaagtaggga agaggtaaaa atggtgaaaa tgagccaaaa atatcaaaga    540
aacaagaata gatcaagtaa tcgccctcct caatccaacc gcaatttcaa agtcgatatt    600
ccgaatgaag attttgactt tcaatcaaat aatgcaaaat tcacgaaagg tgattccact    660
gatgtggaaa agaaaaaaga attagaatca gctgttcaca agcaggatga atctgatgag    720
cagttttata ataaaaaatc gtctttttc gacaccatct ccacttctac tgaaactaat    780
accaatatga gatggcaaga agaaaaaatg ttgaacgttg acacctttgg acaagcttct    840
gccagaccaa gatttcactc tagaggcctc ggtcgtgggc gtggaaatta taggggaaac    900
agaggaaaca gaggaagagg cggccaacgt ggaaactacc aaaacagaaa taactaccaa    960
aatgatagtg gcgcctatca gaaccaaaac gactcgtaca gcagaccagc caaccagttt   1020
tcgcaaccct cttccaacgt tgaattttaa                                    1050
```

<210> SEQ ID NO 48
<211> LENGTH: 349
<212> TYPE: PRT
<213> ORGANISM: Saccharomyces cerevisiae

<400> SEQUENCE: 48

Met Ser Gln Tyr Ile Gly Lys Thr Ile Ser Leu Ile Ser Val Thr Asp
1               5                   10                  15

Asn Arg Tyr Val Gly Leu Leu Glu Asp Ile Asp Ser Glu Lys Gly Thr
            20                  25                  30

Val Thr Leu Lys Glu Val Arg Cys Phe Gly Thr Glu Gly Arg Lys Asn
        35                  40                  45

Trp Gly Pro Glu Glu Ile Tyr Pro Asn Pro Thr Val Tyr Asn Ser Val
    50                  55                  60

Lys Phe Asn Gly Ser Glu Val Lys Asp Leu Ser Ile Leu Asp Ala Asn
65                  70                  75                  80

Ile Asn Asp Ile Gln Pro Val Val Pro Gln Met Met Pro Pro Ala Ser
                85                  90                  95

Gln Phe Pro Pro Gln Gln Ala Gln Ser Pro Pro Gln Ala Gln Ala Gln
            100                 105                 110

Ala His Val Gln Thr Asn Pro Gln Val Pro Lys Pro Glu Ser Asn Val
        115                 120                 125

Pro Ala Ala Val Ala Gly Tyr Gly Val Tyr Thr Pro Thr Ser Thr Glu
    130                 135                 140

Thr Ala Thr Ala Ser Met Asn Asp Lys Ser Thr Pro Gln Asp Thr Asn
145                 150                 155                 160

Val Asn Ser Gln Ser Arg Glu Arg Gly Lys Asn Gly Glu Asn Glu Pro
                165                 170                 175

Lys Tyr Gln Arg Asn Lys Asn Arg Ser Ser Asn Arg Pro Pro Gln Ser
            180                 185                 190

Asn Arg Asn Phe Lys Val Asp Ile Pro Asn Glu Asp Phe Asp Phe Gln
        195                 200                 205

Ser Asn Asn Ala Lys Phe Thr Lys Gly Asp Ser Thr Asp Val Glu Lys
    210                 215                 220

Glu Lys Glu Leu Glu Ser Ala Val His Lys Gln Asp Glu Ser Asp Glu

```
                225                 230                 235                 240
Gln Phe Tyr Asn Lys Lys Ser Ser Phe Phe Asp Thr Ile Ser Thr Ser
                    245                 250                 255
Thr Glu Thr Asn Thr Asn Met Arg Trp Gln Glu Lys Met Leu Asn
                260                 265                 270
Val Asp Thr Phe Gly Gln Ala Ser Ala Arg Pro Arg Phe His Ser Arg
                275                 280                 285
Gly Leu Gly Arg Gly Arg Gly Asn Tyr Arg Gly Asn Arg Gly Asn Arg
            290                 295                 300
Gly Arg Gly Gly Gln Arg Gly Asn Tyr Gln Asn Arg Asn Asn Tyr Gln
305                 310                 315                 320
Asn Asp Ser Gly Ala Tyr Gln Asn Gln Asn Asp Ser Tyr Ser Arg Pro
                325                 330                 335
Ala Asn Gln Phe Ser Gln Pro Pro Ser Asn Val Glu Phe
                340                 345

<210> SEQ ID NO 49
<211> LENGTH: 1656
<212> TYPE: DNA
<213> ORGANISM: Saccharomyces cerevisiae

<400> SEQUENCE: 49
atgtcacaat tgttggtttt cggagtacaa gtggagctaa agatgggaa gctcattcag      60
gggaaaattg ccaaagcaac ctcaaaagga ttgactttaa atgacgttca attcggcgat     120
ggtggtaaat ctcaagcttt caaagtgagg gcgtcaaggc taaggacttt aaaggttcta     180
actgttgcct ctcaatccgg gaaaaggaag cagcaaagac aacagcagca acaaaacgat     240
tataatcaaa atcgcggtga acatattgat tggcaagatg atgatgttag taagataaaa     300
caacaggaag atttcgattt ccaaagaaat ttgggcatgt ttaacaaaaa agacgtcttc     360
gcacaattaa gcaaaatgac gatatatta ccggagaata gattacaggg acataacaga     420
aagcaaaccc aattgcagca aataattat caaaatgatg aattggttat tccagatgca     480
aagaaagatt catggaacaa gatttcttca agaaatgagc aaagcacaca ccaatctcag     540
ccgcaacaag atgctcaaga tgatctggtt ttggaagatg atgaacatga atacgatgtc     600
gatgatatcg atgatcccaa ataacctacca ataactcagt ctttgaatat tacacattta     660
attcactctg caactaactc tccatccata aatgataaaa cgaaaggtac agttataaat     720
gataaggatc aggtactagc taaattaggc cagatgatca tcagccagtc aagatccaac     780
tcaacatcct tgccagctgc aaataaacaa acaaccatca gatcaaagaa cactaagcag     840
aacattccta tggctacacc agtacaacta ctagaaatgg agagcatcac gtccgaattt     900
ttcagtatta actcggcagg gctactagaa aattttgctg taaacgcatc gttcttctta     960
aagcagaaac taggtggccg tgcacgtttta cgtttacaaa attctaatcc ggaacctta    1020
gtagtaatac tagcctcaga ttccaacaga tctggtgcga agctctggc gttgggtaga    1080
catcttttgcc aaacggggca tatccgtgtc ataacattat ttacatgttc tcaaaatgaa    1140
ctacaggatt ccatggtcaa aaagcaaaca gatatttaca agaagtgtgg cggaaaaatt    1200
gttaatagtg tatcgtcgct ggaatctgct atggaaacat aaatagccc tgtagaaata    1260
gtcatcgatg ccatgcaggg atatgactgt acattgagcg atctggcggg gacgtcggaa    1320
gttattgaaa gcagaattaa aagcatgata tcatggtgta acaaacagcg aggatctact    1380
aaagtgtggt ctttggatat tccaaatggg tttgatgcgg gatccggcat gccagatatt    1440
```

```
ttcttttcag acaggattga agcaacagga attatttgtt ctggctggcc tttgattgcc      1500
atcaacaact taattgcaaa tttgccaagt ctagaagatg ctgttttgat tgatataggt      1560
ataccacagg gcgcctattc acagagaact tctttgcgta agttccaaaa ctgtgatctt      1620
ttcgtcactg acgggtccct gctattagat ttgtaa                                1656
```

```
<210> SEQ ID NO 50
<211> LENGTH: 551
<212> TYPE: PRT
<213> ORGANISM: Saccharomyces cerevisiae

<400> SEQUENCE: 50
```

| Met | Ser | Gln | Phe | Val | Gly | Phe | Gly | Val | Gln | Val | Glu | Leu | Lys | Asp | Gly |
|-----|-----|-----|-----|-----|-----|-----|-----|-----|-----|-----|-----|-----|-----|-----|-----|
| 1 | | | | 5 | | | | | 10 | | | | | 15 | |

| Lys | Leu | Ile | Gln | Gly | Lys | Ile | Ala | Lys | Ala | Thr | Ser | Lys | Gly | Leu | Thr |
| | | | 20 | | | | | 25 | | | | | 30 | | |

| Leu | Asn | Asp | Val | Gln | Phe | Gly | Asp | Gly | Gly | Lys | Ser | Gln | Ala | Phe | Lys |
| | | 35 | | | | | 40 | | | | | 45 | | | |

| Val | Arg | Ala | Ser | Arg | Leu | Lys | Asp | Leu | Lys | Val | Leu | Thr | Val | Ala | Ser |
| 50 | | | | | 55 | | | | | 60 | | | | | |

| Gln | Ser | Gly | Lys | Arg | Lys | Gln | Gln | Arg | Gln | Gln | Gln | Gln | Gln | Asn | Asp |
| 65 | | | | | 70 | | | | | 75 | | | | | 80 |

| Tyr | Asn | Gln | Asn | Arg | Gly | Glu | His | Ile | Asp | Trp | Gln | Asp | Asp | Asp | Val |
| | | | | 85 | | | | | 90 | | | | | 95 | |

| Ser | Lys | Ile | Lys | Gln | Gln | Glu | Asp | Phe | Asp | Phe | Gln | Arg | Asn | Leu | Gly |
| | | | 100 | | | | | 105 | | | | | 110 | | |

| Met | Phe | Asn | Lys | Lys | Asp | Val | Phe | Ala | Gln | Leu | Lys | Gln | Asn | Asp | Asp |
| | | 115 | | | | | 120 | | | | | 125 | | | |

| Ile | Leu | Pro | Glu | Asn | Arg | Leu | Gln | Gly | His | Asn | Arg | Lys | Gln | Thr | Gln |
| 130 | | | | | 135 | | | | | 140 | | | | | |

| Leu | Gln | Gln | Asn | Asn | Tyr | Gln | Asn | Asp | Glu | Leu | Val | Ile | Pro | Asp | Ala |
| 145 | | | | | 150 | | | | | 155 | | | | | 160 |

| Lys | Lys | Asp | Ser | Trp | Asn | Lys | Ile | Ser | Ser | Arg | Asn | Glu | Gln | Ser | Thr |
| | | | | 165 | | | | | 170 | | | | | 175 | |

| His | Gln | Ser | Gln | Pro | Gln | Gln | Asp | Ala | Gln | Asp | Leu | Val | Leu | Glu |
| | | | 180 | | | | | 185 | | | | | 190 | | |

| Asp | Asp | Glu | His | Glu | Tyr | Asp | Val | Asp | Ile | Asp | Asp | Pro | Lys | Tyr |
| | | | 195 | | | | | 200 | | | | | 205 | | |

| Leu | Pro | Ile | Thr | Gln | Ser | Leu | Asn | Ile | Thr | His | Leu | Ile | His | Ser | Ala |
| | 210 | | | | | 215 | | | | | 220 | | | | |

| Thr | Asn | Ser | Pro | Ser | Ile | Asn | Asp | Lys | Thr | Lys | Gly | Thr | Val | Ile | Asn |
| 225 | | | | | 230 | | | | | 235 | | | | | 240 |

| Asp | Lys | Asp | Gln | Val | Leu | Ala | Lys | Leu | Gly | Gln | Met | Ile | Ile | Ser | Gln |
| | | | | 245 | | | | | 250 | | | | | 255 | |

| Ser | Arg | Ser | Asn | Ser | Thr | Ser | Leu | Pro | Ala | Ala | Asn | Lys | Gln | Thr | Thr |
| | | | 260 | | | | | 265 | | | | | 270 | | |

| Ile | Arg | Ser | Lys | Asn | Thr | Lys | Gln | Asn | Ile | Pro | Met | Ala | Thr | Pro | Val |
| | | 275 | | | | | 280 | | | | | 285 | | | |

| Gln | Leu | Leu | Glu | Met | Glu | Ser | Ile | Thr | Ser | Glu | Phe | Phe | Ser | Ile | Asn |
| | 290 | | | | | 295 | | | | | 300 | | | | |

| Ser | Ala | Gly | Leu | Leu | Glu | Asn | Phe | Ala | Val | Asn | Ala | Ser | Phe | Phe | Leu |
| 305 | | | | | 310 | | | | | 315 | | | | | 320 |

| Lys | Gln | Lys | Leu | Gly | Gly | Arg | Ala | Arg | Leu | Arg | Leu | Gln | Asn | Ser | Asn |
| | | | | 325 | | | | | 330 | | | | | 335 | |

Pro Glu Pro Leu Val Val Ile Leu Ala Ser Asp Ser Asn Arg Ser Gly
        340                 345                 350

Ala Lys Ala Leu Ala Leu Gly Arg His Leu Cys Gln Thr Gly His Ile
    355                 360                 365

Arg Val Ile Thr Leu Phe Thr Cys Ser Gln Asn Glu Leu Gln Asp Ser
370                 375                 380

Met Val Lys Lys Gln Thr Asp Ile Tyr Lys Lys Cys Gly Gly Lys Ile
385                 390                 395                 400

Val Asn Ser Val Ser Ser Leu Glu Ser Ala Met Glu Thr Leu Asn Ser
                405                 410                 415

Pro Val Glu Ile Val Ile Asp Ala Met Gln Gly Tyr Asp Cys Thr Leu
            420                 425                 430

Ser Asp Leu Ala Gly Thr Ser Glu Val Ile Glu Ser Arg Ile Lys Ser
        435                 440                 445

Met Ile Ser Trp Cys Asn Lys Gln Arg Gly Ser Thr Lys Val Trp Ser
    450                 455                 460

Leu Asp Ile Pro Asn Gly Phe Asp Ala Gly Ser Gly Met Pro Asp Ile
465                 470                 475                 480

Phe Phe Ser Asp Arg Ile Glu Ala Thr Gly Ile Ile Cys Ser Gly Trp
                485                 490                 495

Pro Leu Ile Ala Ile Asn Asn Leu Ile Ala Asn Leu Pro Ser Leu Glu
            500                 505                 510

Asp Ala Val Leu Ile Asp Ile Gly Ile Pro Gln Gly Ala Tyr Ser Gln
        515                 520                 525

Arg Thr Ser Leu Arg Lys Phe Gln Asn Cys Asp Leu Phe Val Thr Asp
    530                 535                 540

Gly Ser Leu Leu Leu Asp Leu
545                 550

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 51
cggagagatg gtcagtcaca                                              20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 52
ttcttgctgc tgcataatcg                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 53
atggccgaaa aggtcaacaa                                              20

```
<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 54
tcaatcctcg tctcgccttt                                               20

<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 55
caaagcttga gctcgaattc atttttgccg tggtagttgc                         40

<210> SEQ ID NO 56
<211> LENGTH: 38
<212> TYPE: PRT
<213> ORGANISM: Artificial Sequence
<220> FEATURE:
<223> OTHER INFORMATION: Synthetic oligonucleotide primer

<400> SEQUENCE: 56

Cys Ala Gly Gly Thr Ala Cys Cys Thr Cys Thr Ala Gly Ala Ala Thr
1               5                   10                  15

Thr Cys Ala Cys Cys Ala Cys Thr Cys Ala Ala Thr Cys Cys Thr Cys
            20                  25                  30

Gly Thr Cys Thr Cys Gly
        35
```

MICROORGANISMS HAVING ENHANCED TOLERANCE TO INHIBITORS AND STRESS

CROSS REFERENCE TO RELATED APPLICATIONS

This application is a divisional of U.S. patent application Ser. No. 12/795,882, filed on Jun. 8, 2010, now abandoned, which claims the benefit of U.S. Provisional Application No. 61/184,961, filed on Jun. 8, 2009, the contents of each of which in its entirety is incorporated herein by reference.

This invention was made with government support under Contract Number DE-AC05-00OR22725 between the United States Department of Energy and UT-Battelle, LLC. The U.S. Government has certain rights in this invention.

FIELD OF THE INVENTION

This invention generally relates to the field of microorganism and genetic modification thereof. In particular, the invention relates to microorganisms that display enhanced tolerance to stress and inhibitors as a result of increased expression of a protein of the Sm-like superfamily such as bacterial Hfq and yeast Sm or Lsm proteins. Such microorganisms are advantageous for use in fermentation of biomass materials to produce biofuels such as ethanol.

BACKGROUND OF THE INVENTION

Biomass-based bioenergy is crucial to meet the goal of making cellulosic biofuels cost-competitive with gasoline. Lignocellulosic materials represent an abundant feedstock for cellulosic-biofuel production. A core challenge in converting cellulosic material to biofuels such as ethanol and butanol is the recalcitrance of biomass to breakdown. Because of the complex structure of lignocellulosic biomass, pretreatment is necessary to make it accessible for enzymatic attack. Severe biomass pretreatments are required to release the sugars, which along with by-products of fermentation can create inhibitors in the production of ethanol or butanol, for example. During the pretreatment processes, a range of inhibitory chemicals are formed that include sugar degradation products such as furfural and hydroxymethyl furfural (HMF); weak acids such as acetic, formic, and levulinic acids; lignin degradation products such as the substituted phenolics vanillin and lignin monomers. In addition, the metabolic byproducts such as ethanol, lactate, and acetate also impact the fermentation by slowing and potentially stopping the fermentation prematurely. The increased lag phase and slower growth increases the ethanol cost due to both ethanol production rate and total ethanol yield decreases (Takahashi et al. 1999; Kadar et al. 2007).

Efficient conversion of lignocellulosic hydrolysates to biofuel requires high-yield production and resistance to industrially relevant stresses and inhibitors. To overcome the issue of inhibition caused by pretreatment processes, there are two approaches, one is to remove the inhibitor after pretreatment from the biomass physically or chemically, which requires extra equipment and time leading to increased costs. A second approach utilizes inhibitor tolerant microorganisms for efficient fermentation of lignocellulosic material to ethanol and their utility is considered an industrial requirement (Almeida et al. 2007).

*Zymomonas mobilis* are gram-negative facultative anaerobic bacteria with a number of desirable industrial characteristics, such as high-specific productivity and ethanol yield, unique anaerobic use of the Entner-Doudoroff pathway that results in low cell mass formation, high ethanol tolerance (12%), pH 3.5-7.5 range for ethanol production and has been generally regarded as safe (GRAS) status (Swings and De Ley 1977; Rogers et al. 1984; Gunasekaran and Raj 1999; Dien et al. 2003; Panesar et al. 2006; Rogers et al. 2007). One drawback to using wild-type *Z. mobilis* is its narrow substrate utilization range. However, recombinant *Z. mobilis* strains have been developed to ferment pentose sugars such as xylose and arabinose (Zhang et al. 1995; Deanda et al. 1996; Mohagheghi et al. 2002). On the other hand, low tolerance to acetic acid and decreased ethanol tolerance have been reported in recombinant strains (Ranatunga et al. 1997; Lawford and Rousseau 1998; Lawford et al. 2001; Dien et al. 2003).

Acetic acid is an inhibitor produced by the de-acetylation of hemicelluloses during biomass pretreatment. At pH 5.0, 36% of acetic acid is in the uncharged and undissociated form (HAc) and is able to permeate the *Z. mobilis* plasma membrane (Lawford and Rousseau 1993). The inhibition mechanism has been ascribed to the ability of the undissociated (protonated) form to cross the cell membrane leading to uncoupling and anion accumulation causing cytoplasmic acidification. Its importance comes from the significant concentrations of acetate that are produced relative to fermentable sugars (McMillan 1994) and the ratio of acetate to fermentable sugars is particularly high in material from hardwoods (Lawford and Rousseau 1993). Acetate may reach inhibitory levels when pretreated biomass hydrolysates are concentrated to generate high final ethanol concentrations or where process water is recycled. Acetate removal processes have been described but they are energy or chemical-intensive and their impact on processing costs have yet to be determined (McMillan 1994).

An acetate tolerant *Z. mobilis* mutant (AcR) has been generated by a random mutagenesis and selection strategy (Joachimstahl and Rogers 1998). The AcR mutant was capable of efficient ethanol production in the presence of 20 g/L sodium acetate while the parent ZM4 was inhibited significantly above 12 g/L sodium acetate under the same conditions. A number of studies have characterized the performance of recombinant *Z. mobilis* strains able to utilize both C-5 and C-6 sugars, including under acetate stress conditions (Lawford et al. 1999; Joachimsthal and Rogers 2000; Lawford and Rousseau 2001). Acetic acid was shown to be strongly inhibitory to wild-type derived strain ZM4(pZB5) on xylose medium and nuclear magnetic resonance studies indicated intracellular deenergization and acidification appeared to be the major inhibition mechanisms (Kim et al. 2000). A recombinant strain able to utilize both xylose (a C-5 sugar) and glucose (a C-6 sugar) with increased acetate resistance was generated by transforming plasmid pZBS into the AcR background (Jeon et al. 2002). Mohagheghi et al. (2004) reported a recombinant *Zymomonas mobilis* 8b tolerated up to 16 g/L acetic acid and achieved 82%-87% (w/w) ethanol yields from pure glucose/xylose solutions.

Acetic acid bacteria are used for the industrial production of vinegar and are intrinsically resistant to acetic acid. Although the resistance mechanism is not completely understood, progress toward this goal has been made in recent years. Spontaneous acetic acid bacteria mutants for *Acetobacter aceti* (Okumura et al. 1985) and several *Acetobacter pasteurianus* strains (Takemura et al. 1991; Chinnawirotpisan et al. 2003) showed growth defects in the presence of acetic acid, which was associated with loss of alcohol dehydrogenase activity. Fukaya et al (1990) identified the aarA, aarB, and aarC gene cluster as being important for conferring acetic acid resistance using a genetic approach (Fukaya et al.

1990). aarA encodes citrate synthase and aarC encodes a protein that is involved in acetate assimilation (Fukaya et al. 1993), and the three aar genes have been suggested to support increased flux through a complete but unusual citric acid cycle to lower cytoplasmic acetate levels (Mullins et al. 2008). The presence of a proton motive force-dependent efflux system for acetic acid has been demonstrated as being important in *A. aceti* acetic acid resistance, although the genetic determinant(s) remain to be identified (Matsushita et al. 2005). In *E. coli*, over-expression of the ATP-dependent helicase RecG has been reported to improve resistance to weak organic acids including acetate (Steiner and Sauer 2003). Baumler et al. (2006) describe the enhancement of acid tolerance in *Z. mobilis* by the expression of a proton-buffering peptide in acidified TSB (HCl (pH 3.0) or acetic acid (pH 3.5)), glycine-HCl buffer (pH 3.0) and sodium acetate-acetic acid buffer (pH 3.5) (Baumler et al. 2006). Baumler et al. (2006) also note that the presence of the antibiotic also significantly increased acid tolerance by an unknown mechanism.

Aerobic, stationary phase conditions were found to produce a number of inhibitory secondary metabolites from *Z. mobilis* when compared to anaerobic conditions at the same time point. The *Z. mobilis* global regulator gene hfq has been identified as associated with stress responses generated under aerobic stationary phase conditions (Yang et al., 2009). Hfq is a bacterial member of the Sm family of RNA-binding proteins, which acts by base-pairing with target mRNAs and functions as a chaperone for non-coding small RNA (sRNA) in *E. coli* (Valentin-Hansen et al. 2004; Zhang et al. 2002; Zhang et al. 2003). *E. coli* Hfq is involved in regulating various processes and deletion of hfq has pleiotropic phenotypes, including slow growth, osmosensitivity, increased oxidation of carbon sources, and altered patterns of protein synthesis in *E. coli* (Valentin-Hansen et al. 2004; Tsui et al. 1994). *E. coli* Hfq has also been reported to affect genes involved in amino acid biosynthesis, sugar uptake, metabolism and energetics (Guisbert et al. 2007). The expression of thirteen ribosomal genes was down-regulated in hfq mutant background in *E. coli* (Guisbert et al. 2007). Hfq also up-regulated sugar uptake transporters and enzymes involved in glycolysis and fermentation such as pgk and pykA, and adhE (Guisbert et al. 2007). *E. coli* Hfq is also involved in regulation of general stress responses that are mediated by alternative sigma factors such as RpoS, RpoE and RpoH. Cells lacking Hfq induce the RpoE-mediated envelope stress response and rpoH is also induced in cells lacking Hfq (Guisbert et al. 2007), which is consistent with our results that *Z. mobilis* hfq was less abundant in aerobic fermentation condition in ZM4 at 26 h post-inoculation and was rpoH induced (Yang et al. 2009).

SUMMARY OF THE INVENTION

It has been identified in accordance with the present invention that increased expression of a protein of the Sm-like superfamily in a microorganism confers enhanced tolerance to stress and inhibitors such as sodium acetate, ammonium acetate, potassium acetate, vanillin, furfural, hydroxymethylfurfural (HMF) and $H_2O_2$. In accordance with the present invention, microorganisms can be genetically modified to increase the expression of a protein of the Sm-like superfamily to achieve enhanced tolerance to stress and inhibitors. Such genetically modified microorganisms are particularly useful for production of biofuels based on fermentation of biomass materials.

In one aspect, the invention is directed to genetically modified microorganisms that display enhanced tolerance to stress and/or inhibitors as a result of increased expression of a protein of the Sm-like superfamily in the microorganisms.

In one embodiment, the microorganism is a genetically engineered bacterial strain, and the protein being expressed at an elevated level is a bacterial Hfq protein.

Bacteria contemplated by the present invention include both Gram-negative and Gram positive bacteria. Examples of bacteria of particular interest include *Acetobacterium*, *Bacillus*, *Streptococcus*, *Clostridium* (e.g., *C. thermocellum*), *Zymomonas* sp. (e.g., *Z. mobilis*), *Anaerocellum* (e.g., *Anaerocellum thermophilum*), *Caldicellulosiruptor* (e.g., *C. saccharolyticus*), *Thermoanaerobacter* (e.g., *Thermoanaerobacter* sp. X514), *Gluconobacter*, and *E. coli*.

Bacterial strains that display enhanced tolerance to stress and/or inhibitors can be generated, e.g., by introducing to a bacterial strain an expression vector which includes the coding sequence of a bacterial Hfq protein. The expression vector directs the expression of the Hfq protein as a replicative plasmid, or mediates the integration of the coding sequence into the host genome to achieve chromosomal expression. Preferably, the bacterial Hfq protein in the vector is identical with or substantially homologous with an endogenous Hfq protein of the recipient bacterial strain.

In specific embodiments, the expression vector includes the coding sequence of a bacterial Hfq protein having an amino acid sequence selected from the group consisting of SEQ ID NO: 2 (*Z. mobilis* ZM4), SEQ ID NO: 4 (*E. coli*), SEQ ID NO: 6 (*Clostridium thermocellum*), SEQ ID NO: 8 (*Anaerocellum thermophilum*), SEQ ID NO: 10 (*Caldicellulosiruptor saccharolyticus*), SEQ ID NO: 12 (*Thermoanaerobacter* sp. X514), and functional derivatives thereof.

In a further embodiment, the invention is directed to genetically engineered fungal strains that display enhanced tolerance to stress and/or inhibitors. Examples of fungi include *Saccharomyces* sp. (e.g., *S. cerevisiae*), *Kluyveromyces* sp., *Pichia* sp. (e.g., *Pichia pastoris*), *Candida* sp., and *Schizosaccharomycetes* sp.

Such fungal strains can be generated, e.g., by introducing to a fungal strain an expression vector which includes the coding sequence of a fungal protein of the Sm-like superfamily. Similarly, the expression vector can be a replicative vector or integrative vector. Preferably, the fungal protein of the Sm-like superfamily in the expression vector is identical with or substantially homologous with an endogenous Sm-like protein of the fungal strain.

In specific embodiments, the expression vector includes the coding sequence of a fungal protein of the Sm-like superfamily having an amino acid sequence selected from the group consisting of SEQ ID NOS: 14, 16, 18, 20, 22, 24, 26, 28, 30, 32, 34, 36, 38, 40, 42, 44, 46, 48 and 50 (representing 19 *S. cerevisiae* Sm and Lsm proteins) and functional derivatives thereof.

The genetically modified microorganisms that display enhanced tolerance to stress and inhibitors can be additionally modified as appropriate, for example, by transformation with additional recombinant genes or sequences suitable for fermentation and production of ethanol. For example, the bacterial and fungal strains can be additionally modified so as to have the ability to utilize C5 sugars such as xylose and arabinose in addition to C6 sugars.

In a further aspect, the present invent provides a method of producing biofuels from cellulosic biomass based on use of the microbial strains that are able to grow at elevated concentrations of inhibitors and/or under stress conditions.

BRIEF DESCRIPTION OF THE DRAWINGS

FIGS. 1A-1E. Domain and motif sites of Z. mobilis Hfq (A), E. coli Hfq (B), S. cerevisiae Sm B (C), and S. cerevisiae Lsm1 (D) proteins. Bacterial Hfq alignment and Clustal W (E). Sequences in (E), Anaerocellum thermophilum, SEQ ID NO: 8; Caldicellulosiruptor saccharol., SEQ ID NO: 10; Clostridium thermocellum, SEQ ID NO: 6; Thermoanaerobacter sp. X514, SEQ ID NO: 12; Zymomonas mobilis ZM4, SEQ ID NO: 2; Escherichia coli K12, SEQ ID NO: 4. Residues that are identical across the species are indicated by "*", and residues that are not identical but conserved in function across the species are indicated by ":".

DETAILED DESCRIPTION OF THE INVENTION

Figures 1A, 1B, 1C, 1D:

It has been identified in accordance with the present invention that increased expression of a protein of the Sm-like superfamily in a microorganism confers enhanced tolerance to stress and inhibitors. Based on this discovery, the present invention provides strains of microorganisms displaying enhanced tolerance to stress and/or inhibitors, which are particularly advantageous for use in fermentation of biomass materials to produce biofuels.

In one aspect, the invention is directed to genetically modified strains of microorganisms that display enhanced tolerance to stress and/or growth inhibitor as a result of increased expression of a protein of the Sm-like superfamily in the microorganisms.

Sm-like superfamily proteins are a highly conserved family of proteins found in eukaryotes, archaea and bacteria, and are characterized by an Sm-like superfamily domain having two conserved motifs referred to as Sm1 motif and Sm2 motif. The Sm1 and Sm2 motifs were first defined for human Sm snRNP proteins (Hermann et al. 1995), and were subsequently found to be highly conserved in other Sm and Lsm (Sm-like) proteins in eukaryotes including plant, *drosophila*, *C. elegans*, and *S. cerevisiae*. Eukaryotic Sm and Lsm proteins are integral to RNA processing and mRNA degradation complexes. Subsequently, the *E. coli* global response regulator Hfq was reported to be a homolog of the Sm and Lsm proteins (Zhang et al. 2002). The bacterial Hfq proteins contain a first region that shares significant similarity with the Sm1 motif found in eukaryotes, and a second region of particularly high conservation among the bacterial proteins which contains a number of conserved hydrophobic residues that align with hydrophobic residues found in the Sm2 motif of eukaryotic cells (Zhang et al. 2002). Similar to the eukaryotic Sm and Lsm proteins, the *E. coli* Hfq protein also forms a multisubunit ring and is believed to also function to enhance RNA-RNA pairing.

As used herein, the term "Sm-like superfamily" includes both Sm and Lsm proteins of eukaryotes and archaea, and Hfq proteins of bacteria.

A eukaryotic protein is considered to be a protein of the Sm-like superfamily in the context of the present invention if the protein contains an Sm-like superfamily domain characterized by the Sm1 motif and Sm2 motif defined by Hermann et al. (1995). Specifically, the Sm1 motif typically spans 32 amino acids, with positions 13 and 23 being Gly and Asn, respectively, positions 1, 3, 11, 15, 18 and 26 being a hydrophobic residue, and positions 19 and 31 being an acidic amino acid (Asp or Glu). The Sm2 motif typically spans only 14 amino acids, and has the consensus sequence (I or L) (R or K) (G or C) at positions 6-8, with positions 1, 4, 11, 13 and 14 being a hydrophobic residue, and positions 9-10 being a hydrophilic residue. Examples of eukaryotic proteins of the Sm-like superfamily include *S. cerevisiae* Sm B, Sm D1, Sm D2, Sm D3, Sm E, Sm F, Sm G, Lsm1, Lsm2, Lsm3, Lsm4, Lsm5, Lsm6, Lsm7, Lsm8, Lsm9, Lsm 13, and Lsm16 (SEQ ID NOS: 14, 16, 18, 20, 22, 24, 26, 28, 30, 32, 34, 36, 38, 40, 42, 44, 46, 48 and 50, respectively). The locations of Sm1 and Sm2 motifs are illustrated for Sm B and Lsm1 proteins in FIGS. 1C-1D.

In the context of the present invention, a bacterial protein is considered to be an Hfq protein and therefore a protein of the Sm-like superfamily if the bacterial protein contains an Sm-like superfamily domain characterized by a first motif similar to the Sm1 motif of eukaryotic proteins defined above, and a second highly conserved region. Generally, the bacterial Sm1 motif spans 26 amino acids, and like the eukaryotic Sm1 motif, has Gly at position 13, an acidic amino acid at position 19 (typically Asp), a hydrophobic residue at positions 1 (preferably V), 3, 11 (preferably L), 15 and 18 (preferably F). Additionally, the second highly conserved region ("the bacterial Sm2 motif") generally spans 12 amino acids, and has a "KHA" sequence at positions 6-8; and preferably, with Y, I and S at positions 5, 9, and 10, respectively, and with a hydrophobic residue at positions 3-4 and 11. Examples of bacterial Hfq proteins include SEQ ID NO: 2 (*Z. mobilis* ZM4), SEQ ID NO: 4 (*E. coli*), SEQ ID NO: 6 (*Clostridium thermocellum*), SEQ ID NO: 8 (*Anaerocellum thermophilum*), SEQ ID NO: 10 (*Caldicellulosiruptor saccharolyticus*), and SEQ ID NO: 12 (*Thermoanaerobacter* sp. X514). Alignment of these bacterial Hfq proteins is provided in FIG. 1B, and the locations of the Sm-like superfamily domain including the Sm1 and Sm2 motifs of *Z. mobilis* and *E. coli* proteins are illustrated in FIG. 1A. It is clear that these six bacterial Hfq proteins share significant homologies, having conserved V, L, G, L, G, F, D and F at positions 1, 5, 8, 11, 13, 18, 19 and 21 of the Sma1 motif, and Y, K, H, A, I, and S at positions 5-10 of the Sm2 motif.

Functional derivatives and homologs of a given protein of the Sm-like superfamily are also suitable for use in the present invention. As used herein, "functional derivatives" and "homologs" of a protein of the Sm-like superfamily refer to proteins that share at least 45% identity or similarity, or preferably at least 50%, 60%, 75%, or 85% identity or similarity, or more preferably 90%, 95%, 98%, or 99% identity or similarity, with the protein of the Sm-like superfamily. Similarity between two protein sequences can be determined, for example, using the well known Lipman-Pearson Protein Alignment program with the following choice of parameters: Ktuple=2, Gap Penalty=4, and Gap Length Penalty=12. Preferably, the derivatives and homologs share consensus motifs of the Sm-like superfamily, which are believed to be critical to the function of the proteins.

A functional derivative of a given protein includes derives where modifications are made to non-conserved residues, as well as a functional or enzymatically active fragment of the protein. The term "functional fragment" or "enzymatically active fragment" means a polypeptide fragment of a full length protein, which substantially retains the activity of the full-length protein. By "substantially" it is meant at least about 50%, or preferably at least 70%, or even 80% or more of the activity of the full-length protein is retained.

The genetically engineered microbial strains of the present invention display enhanced tolerance to stress and/or one or more inhibitors as a result of increased expression of a protein of the Sm-like superfamily.

The term "stress", as used herein, refers generally to environmental stress, i.e., stress received from the environment, such as high temperatures, low temperatures, low pH, oxidation (i.e., the presence of reactive oxidative species such as $H_2O_2$), osmotic, drought, the presence of inhibitors, or nutrient limit such as starvation, among others. For example, "cold stress" is stress on microorganism due to exposure to environments below the minimum optimal growth temperature of the microorganism. "Drought stress" is stress due to exposure of the microorganism to environments under the minimum optimal growth moisture concentration. "Osmotic stress" is stress on microorganisms due to exposure of the microorganisms to environments over or under the maximum or minimum optimal growth osmotic of the microorganisms.

The term "inhibitors" as used herein refer particularly to inhibitory chemical compounds that are formed during biomass pretreatments, including sugar degradation products such as furfural and hydroxymethyl furfural (HMF), weak acids such as acetic, formic, and levulinic acids, lignin degradation products such as the substituted phenolics vanillin and lignin monomers, reactive oxidative species generating hydrogen peroxide ($H_2O_2$) and vanillin, as well as metabolic byproducts such as ethanol, lactate, and acetate. A particularly desirable trait of microorganisms is an enhanced tolerance to sodium and acetate ions, e.g., in the form of sodium acetate, ammonium acetate, and potassium acetate.

In the present invention, microorganisms with enhanced tolerance to stress and/or one or more inhibitors refer to microorganisms which, as a result of genetic modification to increase the level of proteins of the Sm-like superfamily in the microorganisms, demonstrate improved tolerance as compared to microorganisms without the genetic modification. Improved tolerance can be determined by an improved growth profile (either as a shorter lag phase, a shorter doubling time, or a higher maximum density) under a given stress condition or inhibitor concentration. Alternatively, improved tolerance can be determined by an increase in the concentration of an inhibitory molecule which the microorganisms can tolerate.

For example, microorganisms having an elevated expression of Sm-like superfamily proteins exhibit enhanced tolerance to acetate. "Tolerance to acetate" is meant herein to include resistance to acetate salts including, for example, sodium acetate, ammonium acetate and potassium acetate, and/or to acetic acid. Tolerance of a strain to acetate can be determined by assessing the growth of the strain in media containing various concentrations of acetate (e.g., sodium acetate). The microbial strains containing a desirable genetic modification of the present invention are able to grow in media containing a higher concentration of acetate (e.g., sodium acetate) than the unmodified strains. For example, the concentration of sodium acetate that can be tolerated by a strain can be increased by 15%, 20%, 30%, or 50% or higher, as a result of a genetic modification. As demonstrated herein below, wild type Z. mobilis strain ZM4 is unable to grow in media containing 16 g/L (195 mM) sodium acetate, while ZM4-p42-0347 (expressing additional ZM4 Hfq proteins) is able to grow at this concentration. Alternatively, "enhanced tolerance" can be measured by a shorter lag time (e.g., shortened by 10%, 20%, 30% or 50% or greater), a shorter doubling time (e.g., shortened by 10%, 20%, 30% or 50% or greater) or a higher cell density reached at the end of the exponential growth phase (e.g., 25%, 50%, 75%, 100%, 150%, 200%, 500%, or even 1000% or higher cell density). See FIGS. 3A-3C.

Microorganisms encompassed within the scope of the present invention include both bacteria and fungi.

In accordance with the present invention, bacterial strains having enhanced tolerance to stress and inhibitors as a result of increased expression of Sm-superfamily proteins include both Gram-positive and Gram-negative bacteria. Examples of Gram-positive bacteria include those from the genus of *phylum Firmicutes*, particularly strains of *Acetobacterium, Bacillus, Streptococcus, Clostridium* (e.g., *C. thermocellum*), *Anaerocellum* (e.g., *Anaerocellum thermophilum*), *Caldicellulosiruptor* (e.g., *C. saccharolyticus*), and *Thermoanaerobacter* (e.g., *Thermoanaerobacter* sp. X514). Examples of Gram-negative bacteria of particular interest include those generally considered medically safe, such as *Zymomonas* sp. (e.g., *Z. mobilis*), *E. coli, Gluconobacter* sp. (e.g., *Gluconobacter oxydans*, previously known as *Acetobacter suboxydans*), Cyanobacteria, Green sulfur and Green non-sulfur bacteria.

Fungal strains contemplated by the present invention include filamentous and unicellular fungal species, particularly the species from the class of Ascomycota, for example, *Saccharomyces* sp., *Kluyveromyces* sp., *Pichia* sp., *Candida* sp., and *Schizosaccharomycetes* sp. Preferred fungal strains contemplated by the present invention are *S. cerevisiae, S. pombe*, and *Pichia pastoris*. Where the fungal strains are *S. cerevisiae*, additional genetic modifications are preferred besides the genetic modification that results in an increased expression of a Sm-like superfamily protein. For example, *S. cerevisiae* is also modified such that the strain is able to utilize C5 sugars.

Strains of microorganisms that display enhanced tolerance to stress and/or inhibitors as a result of increased expression of a Sm-like superfamily protein can be made using any of the known genetic engineering techniques. For example, the 5' upstream regulatory region of an endogenous Sm-like superfamily gene can be modified to achieve enhanced expression of the encoded endogenous Sm-like superfamily protein.

In one embodiment, a microbial strain having enhanced tolerance is created by introducing an exogenous expression vector into the strain which contains the coding sequence of a protein of the Sm-like superfamily.

In a preferred embodiment, the protein encoded by the expression vector is identical with an endogenous protein of the Sm-like superfamily or a functional derivative thereof, even though homologs from other related species can also be utilized.

Generally, the nucleotide sequence coding for a protein of the Sm-like superfamily is placed in an operably linkage to a promoter and a 3' termination sequence that are functional in a recipient microbial host. The promoter can be a constitutive promoter or an inducible promoter. The promoter can be the native promoter of the Sm-like superfamily gene being expressed, or a heterologous promoter from a different gene. Promoters suitable for use in expression in a bacterial host include, for example, lac promoter, T7, T3 and SP6 phage RNA polymerase promoters. Specific examples of promoters suitable for use in expression in *Zymomonas* species include *Z. mobilis* pdc promoter and adhB promoter. Specific examples of promoters suitable for use in expression in yeast including *S. cerevisiae* include adh1+(constitutive high expression), fbp1+(carbon source responsive), a tetracycline-repressible system based on the CaMV promoter, and the nmt1+(no message in thiamine) promoter. These and other examples of promoters are well documented in the art.

A variety of vector backbones can be used for purpose of the present invention. Choices of vectors suitable for transformation and expression in bacteria and fungi have been well documented in the art. For example, numerous plasmids have been reported for transformation and expression in *Zymomonas*, including, e.g., pZB serial plasmids developed based on *Zymomonas* cryptic plasmid, as described in U.S. Pat. Nos. 5,712,133, 5,726,053, and 5,843,760, and a cloning-compatible broad-host-range destination vector described by Pelletier et al. (2008), among many others.

In addition to the Sm-like superfamily protein expression unit, the expression vector can include other sequences where appropriate, such as sequences for maintenance and selection of the vector, e.g., a selection marker gene and a replication origin. The selection marker gene can be a gene that confers resistance to antibiotics such as ampicillin resistance (Amp$^r$), tetracycline resistance (Tet$^r$), neomycin resistance, hygromycin resistance, and zeocin resistance (Zeo$^r$) genes, or a gene that provides selection based on media supplement and nutrition.

The vector can be a replicative vector (such as a replicating circular plasmid), or an integrative vector which mediates the introduction of the vector into a recipient cell and subsequent integration of the vector into the host genome for chromosomal expression.

For industrial applications, the inhibitors generated from the biomass pretreatments will select for plasmid maintenance where hfq expression confers an advantage to the strain (i.e., enhanced tolerance to inhibitors) in the absence of additional marker or antibiotic selection. The vectors can also be modified to include the parDE genes to enhance plasmid stability in bacteria in the absence of selection using standard molecular biology approaches, as described in the art (Brown et al., 2002; Pecota et al., 1997). Alternatively and preferably, the desired expression unit (such as an hfq coding sequence operably linked to a promoter) is integrated into the chromosome of the microorganism for expression and enhanced stability. Methods for chromosomal integration in bacteria include modified homologous Campbell-type recombination (Kalogeraki et al. 1997) or transposition (Koch et al. 2001). Methods for chromosomal integration in yeast are well known and are described in Amberg et al. (2005).

An expression vector can be introduced into a microbial host by various approaches known in the art, including transformation (e.g., chemical reagent based transformation), electroporation and conjugation.

The genetic modification to a microbial strain results in an increased expression of a Sm-like superfamily protein. Where the exogenously introduced expression unit codes for a protein identical with an endogenous protein, the level of such protein (expressed from both the native sequence and the exogenous sequence) is increased. Where the exogenously introduced expression unit codes for a protein that is not identical with any endogenous protein but is a functional derivative of or most homologous to an endogenous protein, the collective level of the endogenous protein and the exogenous protein is increased as compared to the unmodified strain. The extent of increase in expression contemplated by the present invention is at least 40%, 50%, 75%, 100% (i.e., twice the level of parental strain), or more preferably at least four or five times, or even more preferably at least ten to fifteen times, the level of parental strain. As a practical matter, the level of expression can be assessed both at the mRNA level and at the protein level.

Pretreatment of biomass by chemical or enzymatic methods yields a mixture of hexose sugars (C6 sugars, primarily glucose and mannose) and pentose sugars (C5 sugars, primarily xylose and arabinose). The fermentation of almost all the available C6 and C5 sugars to ethanol or other liquid biofuel is critical to the overall economics of these processes. Most microorganisms are able to ferment glucose but few have been reported to utilize xylose efficiently and even fewer ferment this pentose to ethanol.

The genetically modified strains of microorganisms of the present invention, which display enhanced tolerance to stress and/or one or more inhibitors as a result of increased expression of a Sm-like superfamily protein, can be additionally modified as appropriate. For example, *Z. mobilis* strains over-expressing *Z. mobilis* Hfq can be additionally modified in order to expand the range of substrates that can be utilized by the strains for efficient ethanol production. For instance, *Z. mobilis* strains over-expressing Hfq can also be introduced with additional genes so that the strains can ferment xylose, arabinose or other pentose sugars as the sole carbon source to produce ethanol. See, e.g., U.S. Pat. No. 5,514,583. Additionally, yeast strains over-expressing a Sm or Lsm protein, particularly *S. cerevisiae* strains, can be additionally modified to have an enhanced ability to ferment xylose, arabinose or other pentose sugars to produce ethanol. For example, yeast cells can be modified to overexpress (via transformation with additional expression unit) xylose reductase, xylulokinase, or xylose isomerase; or modified to have reduced expression of xylitol dehydrogenase, PHO13 or a PHO13 ortholog. See, e.g., U.S. Pat. No. 7,285,403, US 20060234364 A1, and US 20080254524 A1, the teachings of which are incorporated herein by reference.

The isolated or genetically modified microbial strains of the present invention are particularly useful for production of biofuels based on fermentation of biomass materials. Therefore, in a further aspect, the present invent provides a method of producing biofuels from cellulosic biomass based on use of the microbial strains of the present invention that are able to grow at elevated concentrations of acetate.

Biofuels contemplated by the present invention include particular the types of biologically produced fuels, such as bioalcohols, based on the action of microorganisms and enzymes through fermentation of biomass materials. Examples of bioalcohols include ethanol, butanol, and propanol.

In a typical cellulosic biomass to alcohol process, raw cellulosic biomass material is pretreated in order to convert, or partially convert, cellulosic and hemicellulosic components into enzymatically hydrolyzable components (e.g., poly- and oligo-saccharides). The pretreatment process also serves to separate the cellulosic and hemicellulosic components from solid lignin components also present in the raw cellulosic material. The pretreatment process typically involves reacting the raw cellulosic biomass material, often as a finely divided mixture or slurry in water, with an acid, such as sulfuric acid. Other common pretreatment processes include, for example, hot water treatment, wet oxidation, steam explosion, elevated temperature (e.g., boiling), alkali treatment and/or ammonia fiber explosion. The pretreated biomass is then treated by a saccharification step in which poly- and oligo-saccharides are enzymatically hydrolyzed into simple sugars. The free sugars and/or oligosaccharides produced in the saccharification step are then subjected to fermentation conditions for the production of ethanol or butanol, for example. Fermentation can be accomplished by combining one or more fermenting microorganisms with the produced sugars under conditions suitable for fermentation.

One can also add enzyme to the fermentor to aid in the degradation of substrates or to enhance alcohol production. For example, cellulase can be added to degrade cellulose to glucose simultaneously with the fermentation of glucose to ethanol by microorganisms in the same fermentor. Similarly, a hemicellulase can be added to degrade hemicellulose.

Because the pretreatment processes and by-products of fermentation can create a range of inhibitors including acetate, it is especially advantageous to utilize the genetically modified microbial strains described herein which display enhanced resistance to acetate and are able to continue fermentation despite acetate present in the fermentation broth, either in the fermentation substrate carried over from pretreatment of biomass material, or built up as a byproduct of fermentation.

For purpose of fermentation, one strain or a mixture of several strains, some or all of which display enhanced tolerance to stress and/or inhibitors, can be used.

Specific fermentation conditions can be determined by those skilled in the art, and may depend on the particular feedstock or substrates, the microorganisms chosen and the type of biofuel desired. For example, when *Zymomonas mobilis* is employed, the optimum pH conditions range from about 3.5 to about 7.5; substrate concentrations of up to about 25% (based on glucose), and even higher under certain conditions, may be used; and no oxygen is needed at any stage for microorganism survival. Agitation is not necessary but may enhance availability of substrate and diffusion of ethanol.

After fermentation, alcohol is separated from the fermentation broth by any of the many conventional techniques known to separate alcohol from aqueous solutions, including evaporation, distillation, solvent extraction and membrane separation. Particles of substrate or microorganisms may be removed before separation to enhance separation efficiency.

Table 1. List all the sequence identifiers for the nucleotide and protein sequences of the Sm-like superfamily molecules exemplified in the present application.

The present invention is further illustrated and by no means limited by the following examples.

TABLE 1

| SEQ ID NO | Description |
|---|---|
| 1 | *Zymomonas mobilis* hfq nucleotide |
| 2 | *Zymomonas mobilis* Hfq amino acid |
| 3 | *E. coli* hfq nucleotide |
| 4 | *E. coli* Hfq amino acid |
| 5 | *Clostridium thermocellum* hfq nucleotide |
| 6 | *Clostridium thermocellum* Hfq amino acid |
| 7 | *Anaerocellum thermophilum* hfq nucleotide |
| 8 | *Anaerocellum thermophilum* Hfq amino acid |
| 9 | *Caldicellulosiruptor saccharolyticus* hfq nucleotide |
| 10 | *Caldicellulosiruptor saccharolyticus* Hfq amino acid |
| 11 | *Thermoanaerobacter* sp. X514 hfq nucleotide |
| 12 | *Thermoanaerobacter* sp. X514 Hfq amino acid |
| 13 | *S. cerevisiae* SMB1 nucleotide |
| 14 | *S. cerevisiae* Sm B amino acid |
| 15 | *S. cerevisiae* SMD1 nucleotide |
| 16 | *S. cerevisiae* Sm D1 amino acid |
| 17 | *S. cerevisiae* SMD2 nucleotide |
| 18 | *S. cerevisiae* Sm D2 amino acid |
| 19 | *S. cerevisiae* SMD3 nucleotide |
| 20 | *S. cerevisiae* Sm D3 amino acid |
| 21 | *S. cerevisiae* SME1 nucleotide |
| 22 | *S. cerevisiae* Sm E amino acid |
| 23 | *S. cerevisiae* SMX3 nucleotide |
| 24 | *S. cerevisiae* Sm F amino acid |
| 25 | *S. cerevisiae* SMX2 nucleotide |
| 26 | *S. cerevisiae* Sm G amino acid |
| 27 | *S. cerevisiae* LSM1 nucleotide |
| 28 | *S. cerevisiae* Lsm1 amino acid |
| 29 | *S. cerevisiae* LSM2 nucleotide |
| 30 | *S. cerevisiae* Lsm2 amino acid |
| 31 | *S. cerevisiae* LSM3 nucleotide |
| 32 | *S. cerevisiae* Lsm3 amino acid |
| 33 | *S. cerevisiae* LSM4 nucleotide |
| 34 | *S. cerevisiae* Lsm4 amino acid |
| 35 | *S. cerevisiae* LSM5 nucleotide |
| 36 | *S. cerevisiae* Lsm5 amino acid |
| 37 | *S. cerevisiae* LSM6 nucleotide |
| 38 | *S. cerevisiae* Lsm6 amino acid |
| 39 | *S. cerevisiae* LSM7 nucleotide |
| 40 | *S. cerevisiae* Lsm7 amino acid |
| 41 | *S. cerevisiae* LSM8 nucleotide |
| 42 | *S. cerevisiae* Lsm8 amino acid |
| 43 | *S. cerevisiae* LSM9 nucleotide |
| 44 | *S. cerevisiae* Lsm9 amino acid |
| 45 | *S. cerevisiae* LSM12 nucleotide |
| 46 | *S. cerevisiae* Lsm12 amino acid |
| 47 | *S. cerevisiae* LSM13 nucleotide |
| 48 | *S. cerevisiae* Lsm13 amino acid |
| 49 | *S. cerevisiae* LSM16 nucleotide |
| 50 | *S. cerevisiae* Lsm16 amino acid |

Example 1

This example describes the materials and methods used in the experiments described in the subsequent examples.

Strains and Culture Conditions

Bacterial strains and plasmids used in this study are listed in Table 2. *E. coli* strains were cultured using Luria-Bertani (LB) broth or plates. *E. coli* WM3064 was supplemented with 100 μg/mL diaminopimelic acid (DAP). *Z. mobilis* ZM4 was obtained from the American Type Culture Collection (ATCC31821) and the *Z. mobilis* acetate tolerant strain AcR has been described previously (Joachimsthal et al. 2000). ZM4 and AcR were cultured in RM medium at 30° C. *S. cerevisiae* wild-type, deletion mutant and GST-fusion ORF over-expression strains were obtained through Open Biosystems (Huntsville, Ala.). *S. cerevisiae* strains were cultured in rich YPD media. CM media with 2% glucose was used for *S. cerevisiae* wild-type and *S. cerevisiae* deletion mutants, CM media with 2% glucose minus uracil was used for *S. cerevisiae* GST-over expressing strains, 2% galactose was used to induce the GST-fusion strains. Plasmid-containing strains were routinely grown with antibiotics at the following concentrations (μg/mL): kanamycin of 50 for *E. coli* and 200 for ZM4; tetracycline, 10 for *E. coli* and 20 for ZM4; and gentamicin, 10 for *E. coli*. G418 of 200 for *S. cerevisiae* YKO deletion mutants. Growth was monitored turbidometrically by measuring optical density at $600_{nm}$ periodically with the Bioscreen C automated microbiology growth curve analysis system (Growth Curve USA, Piscataway, N.J.).

PCR and DNA Manipulations

Genomic DNA from *Z. mobilis* was isolated using a Wizard Genomic DNA purification kit, following the manufacturer's instructions (Promega, Madison, Wis.). The QIAprep Spin Miniprep and HiSpeed Plasmid Midi kits (Qiagen, Valencia, Calif.) were used for plasmid isolation, respectively. PCR, restriction enzyme digestion, DNA ligation, DNA cloning, and DNA manipulations were done following standard molecular biology approaches (Sambrook 2000).

Figure 2A:
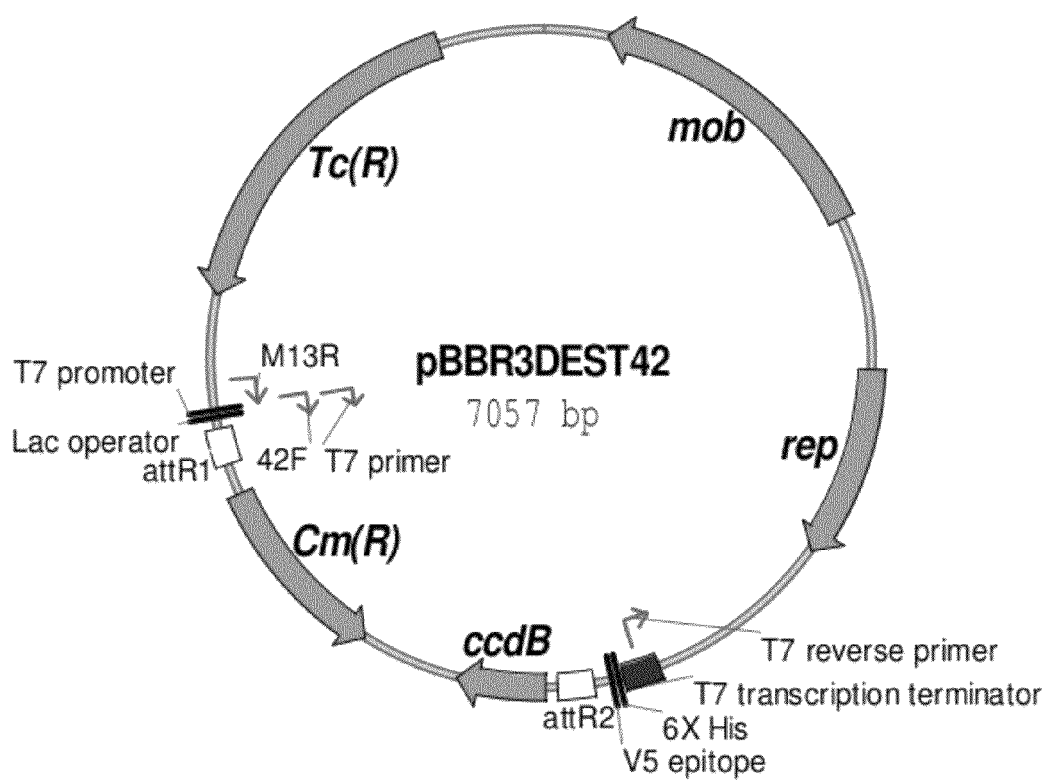
FIG. 2A. Graphic map of the low copy number Gateway® compatible plasmid pBBR3-DEST42. Tc(R): Tetracycline resistance gene tet; Cm: chloramphenicol resistance gene cat. attR1 and attR2 are recombination sites allowing recombinational cloning of the gene of interest from an entry clone; ccdB is ccdB gene allowing negative selection of expression clones.

Construction of the Novel Tetracycline Resistant Gateway Entry Vector and ZMO0347 Over-Expression Plasmid The construction of the broad-host-range, tetracycline resistant Gateway® compatible destination plasmid vector pBBR3DEST42 (FIG. 2A) was carried out essentially as described previously (Pelletier et al. 2008), except that pBBRMCS-3 tetracycline resistance cassette was used in this study instead of pBBRMCS-5 gentamicin resistance cassette used to construct pBBR3DEST42. Briefly, pBBR1MCS3 plasmid DNA was restricted with the KpnI and PvuI enzymes, treated with calf intestine alkaline phosphatase and purified using a Qiagen gel purification kit according to the manufacturer's instructions (Qiagen, Valencia, Calif.). The recombination region on pET-DEST42 vector DNA (Invitrogen, Carlsbad, Calif.) was PCR-amplified using the primers 42F and 42R that include KpnI and PvuI restriction sites as described previously (Pelletier et al. 2008). The gel-purified PCR product was ligated with pBBR1MCS3 KpnI/PvuI fragment with Fast-Link™ DNA Ligation Kit (Epicentre, Madison, Wis.). Ligation products were transformed into *E. coli* DB3.1 chemically competent cells (Invitrogen, Carlsbad, Calif.) and the transformants were selected by plating on LB agar plates containing tetracycline. Individual colonies were grown overnight in LB containing 30 μg/mL chloramphenicol and 10 μg/mL tetracycline, and plasmid DNA was prepared using QIAprep spin miniprep or HiSpeed Plasmid Midi Kit following the manufacturer's protocol (Qiagen, Valencia, Calif.). Plasmid DNA was digested with KpnI and PvuI and digestion products were analyzed on an agarose gel to confirm the presence of products of the expected sizes.

The construction of entry vector and expression clone of target gene hfq (ZMO0347) was carried out as described previously (Pelletier et al. 2008). Briefly, target gene hfq (ZMO0347) was PCR amplified using AcR genomic DNA as template and primer hfq_CF and hfq_CR as primers. PCR products were then cloned into Gateway® entry clone pDONR221 using BP Clonase II enzyme mix following the manufacturer's protocol (Invitrogen, Carlsbad, Calif.), and then transformed into chemically competent DH5a cells (Invitrogen, Carlsbad, Calif.) and plated onto LB with appropriate antibiotic selection. The inserts were confirmed by sequencing using M13 forward and reverse primers (Integrated DNA Technologies, Inc., Coralville, Iowa). The confirmed entry clone vector was then recombined with the destination vector pBBR3DEST42 using LR Clonase II enzyme mix (Invitrogen Carlsbad, Calif.) to create the expression vector as described previously (Pelletier et al. 2008). The resulting expression vector construct was designed as p42-0347. The plasmid construct p42-0347 was confirmed by sequencing using BigDye Terminator v3.1 Cycle Sequencing Kit (Applied Biosystems Inc., Foster City, Calif.).

Mutant Plasmid Construction

Briefly, a 262-bp hfq internal part PCR product was purified and cloned into pKnock-Km suicide vector (Alexeyev 1999) digested with XbaI and HindIII restriction enzymes followed by de-phosphorylation. The plasmid construct named as pKm-0347 was then sequenced to confirm the presence of the target gene fragment, which was then electroporated into *E. coli* WM3064 strain. The transformant *E. coli* WM3064 (pKm-0347) was verified by PCR and sequencing for the presence of correct plasmid construct pKm-0347. *E. coli* WM3064 (pKm-0347) was then conjugated with AcR. The conjugant of potential hfq mutant grown on RM plate with kanamycin concentration of 200 µg/mL and no DAP was selected based on PCR size shift by comparing the PCR size of wild-type AcR and conjugants using primer hfq_OCF and hfq_OCR (Table 2). Wild-type AcR has a 1050-bp PCR product and hfq mutant candidates have a 2.9-kb PCR product. The PCR product was sequenced for mutant confirmation.

Figure 2B:
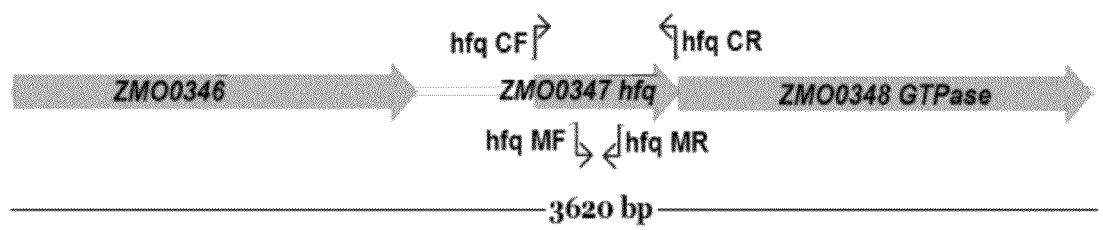
FIG. 2B. The insertion position and complementation region of ZMO0347 as well as the primers and mutation position. ZMO0346, ZMO0347, and ZMO0348 are Z. mobilis ZM4 genes. hfq_MF and hfq_MR are primers used for insertional mutant construction using pKNOCK mutagenesis system. Hfq_CF and Hfq_CR are primers used to clone the hfq gene into pBBR3-DEST42 for complementation, which resulted in a plasmid called as p42-0347. The primer sequences are: hfq_MF: cggagagatggtcagtcaca (SEQ ID NO: 51); hfq_MR: ttcttgctgctgcataatcg (SEQ ID NO: 52); Hfq_CF: atggccgaaaaggtcaacaatc (SEQ ID NO: 53); Hfq_CR: atcctcgtctcgcctttctgtc (SEQ ID NO: 54).

The internal part of the *Z. mobilis* hfq gene (ZMO0347) was amplified by PCR using primers hfq_MF and hfq_MR supplied by MWG-Biotech (Huntsville, Ala.). The hfq gene and the primer positions used for mutant construction and an hfq gene-expressing vector are shown in FIG. 2B. The 262-bp hfq internal part PCR product was then purified and cloned into pCR2.1-TOPO and then transformed into *E. coli* TOPO one competent cell (Invitrogen, Carlsbad, Calif.). Transformants containing the correct construct were confirmed by PCR and sequencing. The plasmid was then extracted using Qiagen Midiprep and digested XbaI and HindIII restriction enzyme, the 262-bp hfq internal part was then purified by Qiagen Gel purification kit. Similarly, pKnock-Km suicide vector was also digested with XbaI and HindIII restriction enzyme followed by de-phosphorylation, and then ligated with 262-bp purified hfq internal part using Fast-Link™ DNA Ligation Kit (Epicentre, Madison, Wis.). The ligation product (pKm-0347) was then transformed into TransforMax EC100D pir-116 Electrocompetent *E. coli* competent cells (Epicentre, Madison, Wis.) by electroporation. Transformants containing plasmid pKm-0347 were selected on LB agar plate with 50 µg/mL kanamycin. The plasmid was then extracted from the transformants, sequenced to confirm the presence of the target gene fragment, and was then electroporated into *E. coli* WM3064 strain. Transformants were verified by PCR and sequencing using BigDye Terminator v3.1 Cycle Sequencing Kit (Applied Biosystems Inc., Foster City, Calif.) for the presence of the correct plasmid construct pKm-0347.

Plasmid Transformation of *Z. mobilis*

*Z. mobilis* wild-type ZM4 and acetate tolerant strain AcR cultures were grown aerobically at 30° C. in RM, and *E. coli* WM3064 containing plasmid pKm-0347 or p42-0347 cultures were grown at 37° C. in LB containing 100 µg/mL DAP and 10 µg/mL tetracycline to exponential phase. *E. coli* WM3064 cells containing plasmid pKm-0347 or p42-0347 were washed with RM for three times by centrifugation at 13,000 rpm for 1 min and resuspended in RM. AcR cells were mixed with *E. coli* WM3064 (pKm-0347) cells in different ratios (1:3, 1:1, and 3:1). Similarly, ZM4 or AcR cells were mixed with *E. coli* WM3064 (p42-0347) cells in different ratios (1:3, 1:1, and 3:1). The mixtures of cells were plated onto RM agar plates with 100 µg/mL DAP and 10 µg/mL tetracycline for plasmid p42-0347 conjugation or 50 µg/mL kanamycin for plasmid pKm-0347 conjugation. The cells were incubated at 30° C. overnight. Conjugants were selected by plating on RM agar plates containing 20 µg/mL tetracycline for p42-0347 plasmid conjugants or 200 µg/mL kanamycin for pKm-0347plasmid conjugants at 30° C. The conjugants were confirmed for the presence of correct plasmid constructs by PCR and sequencing using BigDye Terminator v3.1 Cycle Sequencing Kit (Applied Biosystems Inc., Foster City, Calif.).

TABLE 2

Bacterial strains, plasmids and primers used in this application.

| Strain, plasmid, or primer | Genotype, phenotype, or sequence of primer (5' to 3') | Reference |
|---|---|---|
| *E. coli* | | |
| K-12 | K-12 MG1655 Wild-type strain | Joachimstahl et al. (1998) |
| DH5α | F− Φ80dlacZΔM15 Δ(lacZYA-argF) U169 recA1 endA1 hsdR17($r_k^-$, $m_k^+$) phoA supE44 λ− thi-1 gyrA96 relA1 | Novagen |
| DB3.1 | F− gyrA462 endA1Δ(sr1-recA) mcrB mrr hsdS20($r_B^-$, $m_B^-$) supE44 ara-14 galK2 lacY1 proA2 rpsL20($Sm^R$) xyl-5λ- leu mtl1 | Invitrogen |
| WM3064 | | Denef et al. (2006) |
| BL21(DE3) | F- ompT hsdSB(rB-mB-) gal dcm (DE3) | Invitrogen |
| *Zymomonas mobilis* | | |
| ZM4 | ATCC31821 | |
| AcR | ZM4 acetate tolerant strain generated by random mutagenesis | Joachimstahl et al. (1998) |

TABLE 2-continued

Bacterial strains, plasmids and primers used in this application.

| Strain, plasmid, or primer | Genotype, phenotype, or sequence of primer (5' to 3') | Reference |
|---|---|---|
| ZM4(p42-0347) | ZM4 containing plasmid p42-0347 | This application |
| AcRIM0347 | Insertional mutant of AcR gene ZMO0347 | This application |
| AcRIM0347 (p42-0347) | AcRIM0347 containing plasmid p42-0347 | This application |
| *S. cerevisiae* | | |
| BY4741 | MATa his3Δ1 leu2Δ0 ura3Δ0 met15Δ0-s288c background | Open Biosystems |
| YSC1021-547768 | Yeast: Yeast Knock Out Strain, NHA1 Clone Id: 14095 Accession: YLR138W | Open Biosystems |
| YSC1021-551633 | Yeast: Yeast Knock Out Strain, VNX1 Clone Id: 1123 Accession: YNL321W | Open Biosystems |
| YSC1021-553567 | Yeast: Yeast Knock Out Strain, ARR3 Clone Id: 5616 Accession: YPR201W | Open Biosystems |
| YSC1021-555633 | Yeast: Yeast Knock Out Strain, NHX1 Clone Id: 4290 Accession: YDR456W | Open Biosystems |
| YSC1021-551475 | Yeast: Yeast Knock Out Strain, transporter Clone Id: 610 Accession: YMR034C | Open Biosystems |
| YSC1021-551268 | Yeast: Yeast Knock Out Strain, PSR1 Clone Id: 1498 Accession: YLL010C | Open Biosystems |
| YSC1021-551318 | Yeast: Yeast Knock Out Strain, PSR2 Clone Id: 1574 Accession: YLR019W | Open Biosystems |
| YSC1021-555189 | Yeast: Yeast Knock Out Strain Clone Id: 2341 Accession: YIR005W | Open Biosystems |
| YSC1021-554440 | Yeast: Yeast Knock Out Strain Clone Id: 1301 Accession: YJL124C | Open Biosystems |
| YSC1021-552226 | Yeast: Yeast Knock Out Strain Clone Id: 4214 Accession: YDR378C | Open Biosystems |
| YSC1021-556031 | Yeast: Yeast Knock Out Strain Clone Id: 7383 Accession: YNL147W | Open Biosystems |
| YSC1021-552677 | Yeast: Yeast Knock Out Strain Clone Id: 3501 Accession: YCR020C-A | Open Biosystems |
| YSC1021-552563 | Yeast: Yeast Knock Out Strain Clone Id: 1949 Accession: YHR121W | Open Biosystems |
| YSC1021-552280 | Yeast: Yeast Knock Out Strain Clone Id: 255 Accession: YEL015W | Open Biosystems |
| YSC1021-553518 | Yeast: Yeast Knock Out Strain Clone Id: 5544 Accession: YPR129W | Open Biosystems |

TABLE 2-continued

Bacterial strains, plasmids and primers used in this application.

| Strain, plasmid, or primer | Genotype, phenotype, or sequence of primer (5' to 3') | Reference |
|---|---|---|
| YSC1021-553919 | Yeast: Yeast Knock Out Strain Clone Id: 3618 Accession: YDR259C YAP6 | Open Biosystems |
| YSC4515-98809240 | Yeast GST-Tagged Strain Clone Id: YLR138W Accession: YLR138W | Open Biosystems |
| YSC4515-98810980 | Yeast GST-Tagged Strain Clone Id: YLL010C Accession: YLL010C | Open Biosystems |
| YSC4515-98807049 | Yeast GST-Tagged Strain Clone Id: YJL124C Accession: YJL124C | Open Biosystems |
| YSC4515-98805426 | Yeast GST-Tagged Strain Clone Id: YCR020C-A Accession: YCR020C-A | Open Biosystems |
| YSC4515-98809076 | Yeast GST-Tagged Strain Clone Id: YEL015W Accession: YEL015W | Open Biosystems |
| YSC4515-98808930 | Yeast GST-Tagged Strain Clone Id: YPR129W Accession: YPR129W | Open Biosystems |
| YSC4515-98806813 | Yeast GST-Tagged Strain Clone Id: YHR121W Accession: YHR121W | Open Biosystems |
| YSC4515-98811389 | Yeast GST-Tagged Strain Clone Id: YDR378C Accession: YDR378C | Open Biosystems |
| YSC4515-98805850 | Yeast GST-Tagged Strain Clone Id: YDR259C Accession: YDR259C | Open Biosystems |
| Plasmids | | |
| pKNOCK-Km | Km$^r$, mob, broad host range cloning vector, 1.8 kb | Alexeyev (1999) |
| pET-DEST42 pBBR1MCS-3 | Ap$^r$, Cm$^r$, C-terminal 6xHis and V5 epitope Tc$^r$, mob, broad host range cloning vector | Invitrogen |
| pBBR3DEST42 | Cm$^r$ Tc$^r$, C-terminal 6xHis and V5 epitope | This application |
| pDONR221 | Km$^r$, gateway entry vector Gm$^r$, N-terminal GST | Invitrogen |
| F42-0347 | pBBR3DEST42 containing ZM4 gene ZMO0347 | This application |
| Primers | | |
| hfq_MF | cggagagatggtcagtcaca (SEQ ID NO: 51) | 262-bp |
| hfq_MR | ttcttgctgctgcataatcg (SEQ ID NO: 52) | |
| hfq_CF | atggccgaaaaggtcaacaa (SEQ ID NO: 53) | 483-bp |
| hfq_CR | tcaatcctcgtctcgcctt (SEQ ID NO: 54) | |

TABLE 2-continued

Bacterial strains, plasmids and primers used in this application.

| Strain, plasmid, or primer | Genotype, phenotype, or sequence of primer (5' to 3') | Reference |
|---|---|---|
| hfq_OCF | caaagcttgagctcgaattcatttttgccgtggtagttgc (SEQ ID NO: 55) | 1050-bp |
| hfq_OCR | caggtacctctagaattcaccactcaatcctcgtctcg (SEQ ID NO: 56) | |

Example 2

This example describes the results of the experiments showing that overexpression of the Zymomonas mobilis global regulator gene hfq confers enhanced tolerance to sodium acetate.

Figures 3A, 3B:
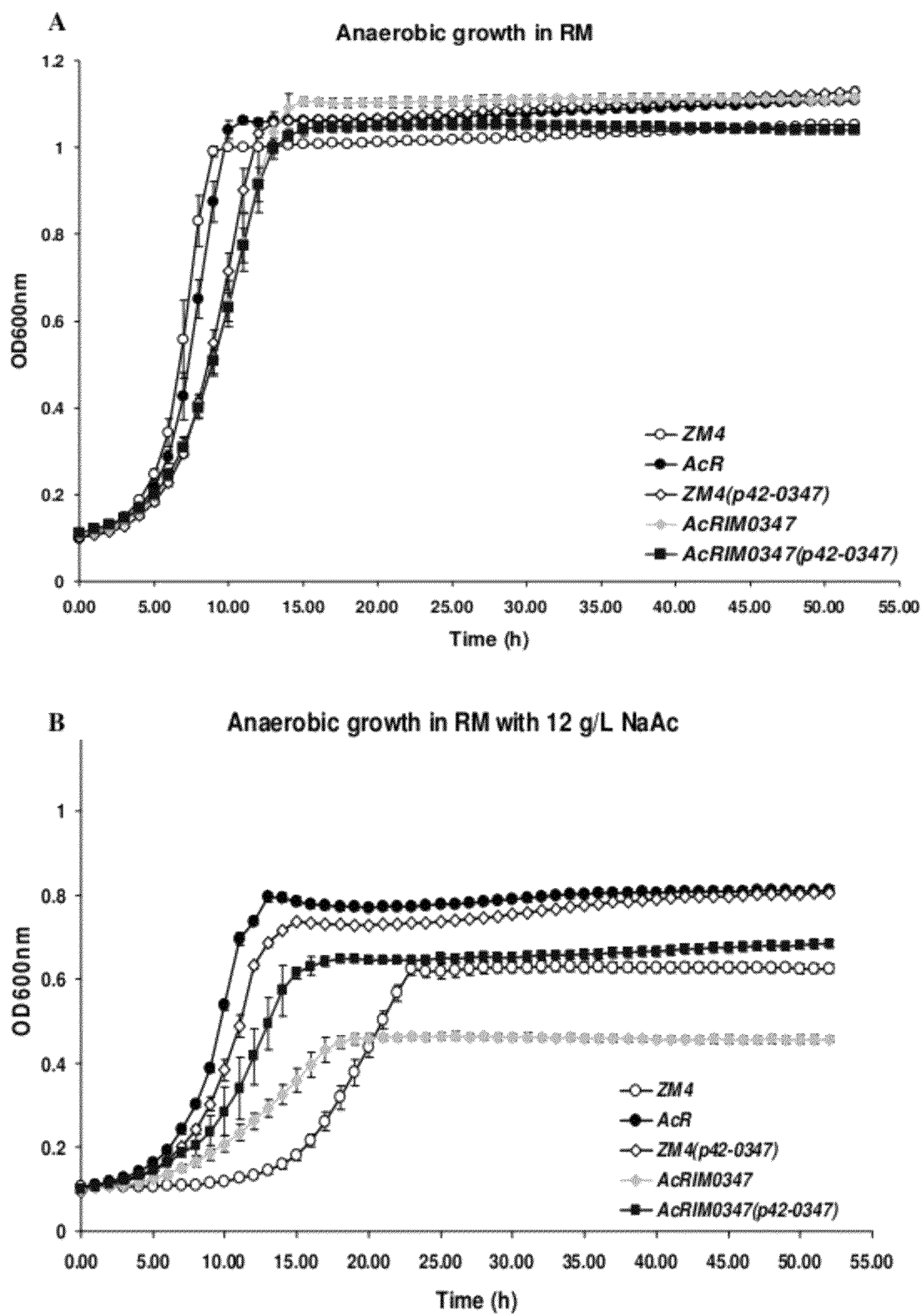
FIGS. 3A-3C. Hfq is responsible for sodium acetate tolerance of Z. mobilis. Z. mobilis strains were grown in RM (pH5.0) overnight, 20-µL culture were then transferred into 250-µL, RM media in the Bioscreen plate. The growth differences of different strains were monitored by Bioscreen (GrowthCurve, MA) under anaerobic conditions in RM (pH5.0) containing 0, 12, and 16 g/L NaAc (A, B, C respectively). Strains included in this study are: ZM4: Zymomonas mobilis ZM4 wild-type; AcR: ZM4 acetate tolerant mutant (Joachimstahl 1998); ZM4 (p42-0347): ZM4 containing a gateway plasmid p42-0347 over-expressing ZM4 gene ZMO0347; AcRIM0347: AcR insertional mutant of ZMO0347; AcRIM0347 (p42-0347): AcRIM0347 containing gateway plasmid p42-0347 over-expressing ZM4 gene ZMO0347. This experiment has been repeated at least three times with similar result. Triplicates were used for each condition.
Figure 3C:
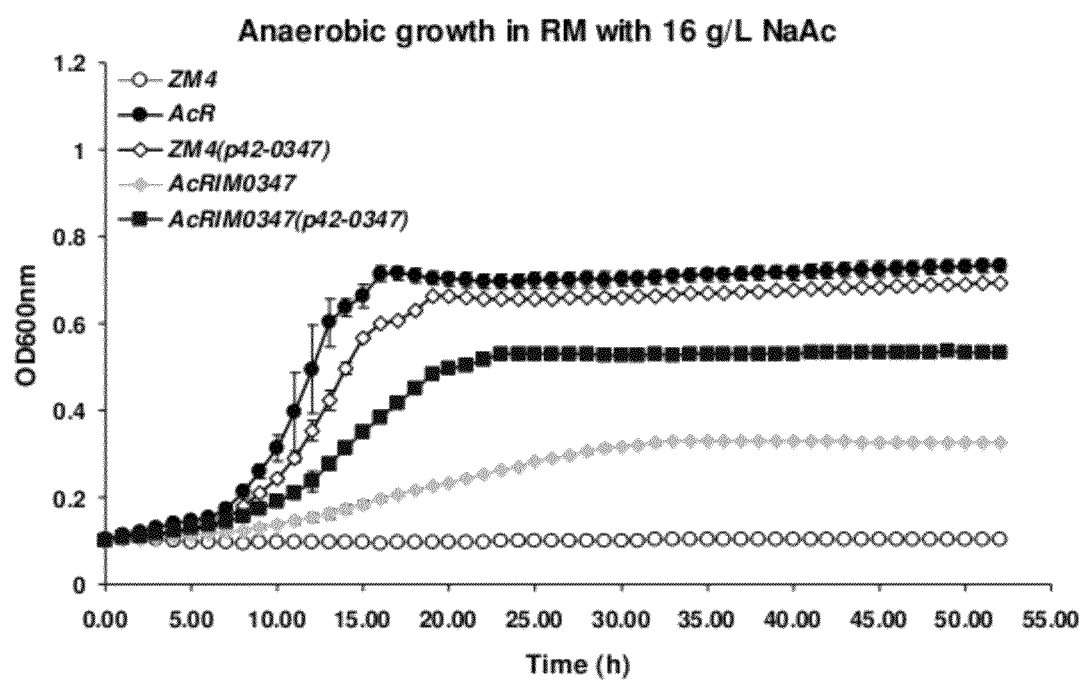

The Z. mobilis hfq gene (SEQ ID NO: 1) was cloned into the vector pBBR3-DEST42 (FIG. 2A) and the resulting plasmid construct p42-0347 was transformed into the wild-type strain ZM4 and acetate mutant AcR through conjugation. In addition, an insertional mutant of Z. mobilis strain AcR hfq gene (ZMO0347) was created using the pKNOCK system (Brown 2006; Alexeyev 1999) and complemented with plasmid p42-0347. The hfq gene and the primer positions used for mutant construction and hfq gene over-expression are shown in FIG. 2B. An insertional mutant of hfq (ZMO0347) was generated in the AcR background and designated as strain "AcRIM0347". The hfq gene was over-expressed via plasmid p42-0347 in both wild-type ZM4 and the acetate mutant AcR backgrounds, their susceptibilities to sodium acetate and other stressors were tested in growth assays along with strains ZM4 and AcR. The AcR acetate tolerant mutant is more tolerant to sodium acetate than its wild-type ZM4 parental strain (Joachimstahl et al. 1998); however, the insertional inactivation of the hfq gene in AcR reduces its sodium acetate tolerance (FIGS. 3A-3C). These strains were tested for their growth responses in four different concentrations of sodium acetate: 0, 12 g/L, 16 g/L (195 mM) and 20 g/L (FIGS. 3A-3C).

The sum of these data show that hfq expression contributed to sodium acetate tolerance. The AcRIM0347 mutant strain grew slightly more slowly in RM medium compared to the parental strain, i.e., in the absence of the sodium acetate stressor (FIG. 3A). Strains ZM4 and AcR with intact hfq genes grew faster than the hfq mutant AcRIM0347 strain in the presence of 12 g/L sodium acetate (FIG. 3B). The AcRIM0347 mutant phenotype was mostly restored by hfq expression and complementation via plasmid p42-0347. Similar, but more dramatic growth phenotypes were observed for sodium acetate of 16 g/L with the wild-type strain unable to grow at this concentration (FIG. 3C).

Example 3

This example describes the experiments performed to compare the negative effects of pretreatment inhibitors on Z. mobilis growth, and to demonstrate that Hfq overexpression confers tolerance to pretreatment inhibitors.

Pretreatment Inhibitors had Negative Effects on Z. mobilis Growth

Figure 4A:
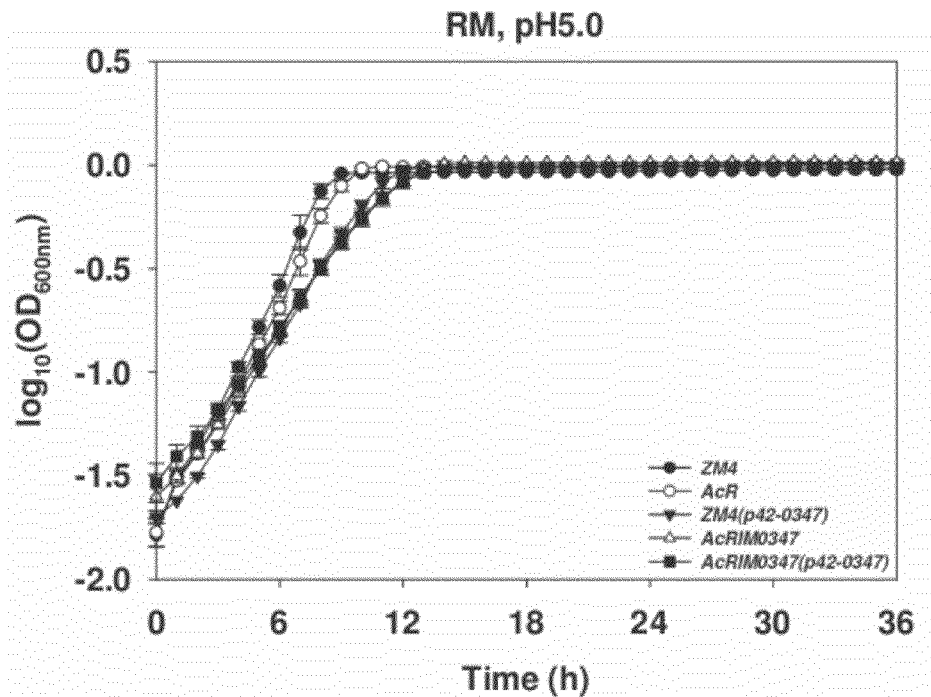
FIGS. 4A-4E. Hfq contributes to Z. mobilis acetate tolerance. Z. mobilis strains were grown in RM (pH5.0) overnight, 5-µL culture were then transferred into 250-µL RM media in the Bioscreen plate. The growth differences of different strains were monitored by Bioscreen (Growth Curves USA, N.J.) under anaerobic conditions; in RM, pH 5.0 (A), RM with 195 mM NaCl, pH 5.0 (B), 195 mM NaAc, pH 5.0 (C), 195 mM NH$_4$OAc, pH 5.0 (D), or 195 mM KAc, pH 5.0 (E). Strains included in this study are: ZM4: Zymomonas mobilis ZM4 wild-type; AcR: ZM4 acetate tolerant mutant; ZM4 (p42-0347): ZM4 containing a gateway plasmid p42-0347 to express ZM4 gene ZMO0347; AcRIM0347: AcR insertional mutant of ZMO0347; AcRIM0347 (p42-0347): AcRIM0347 containing gateway plasmid p42-0347. This experiment has been repeated at least three times with similar result. Duplicate biological replicates were used for each condition.
Figure 4B:
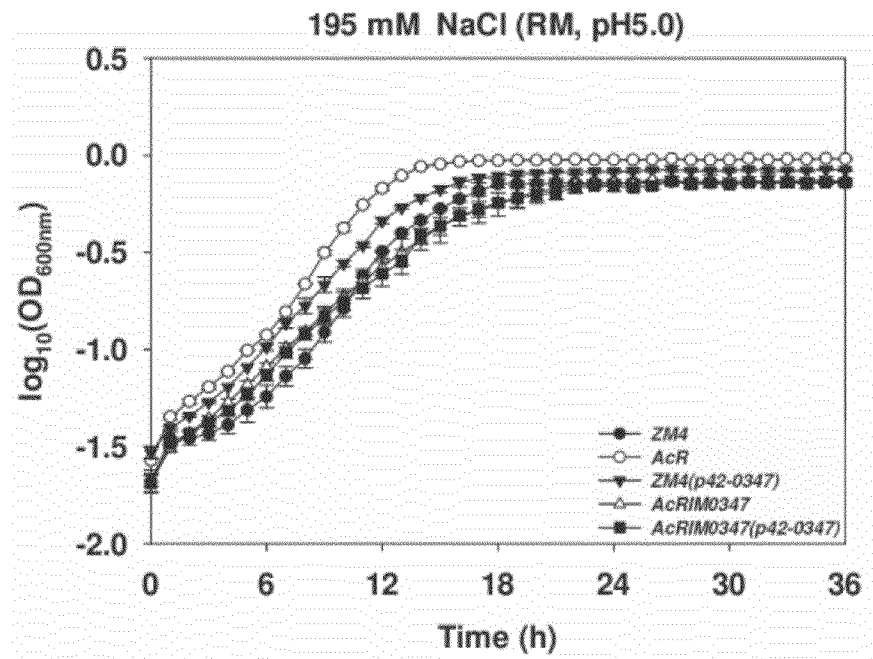
Figure 4C:
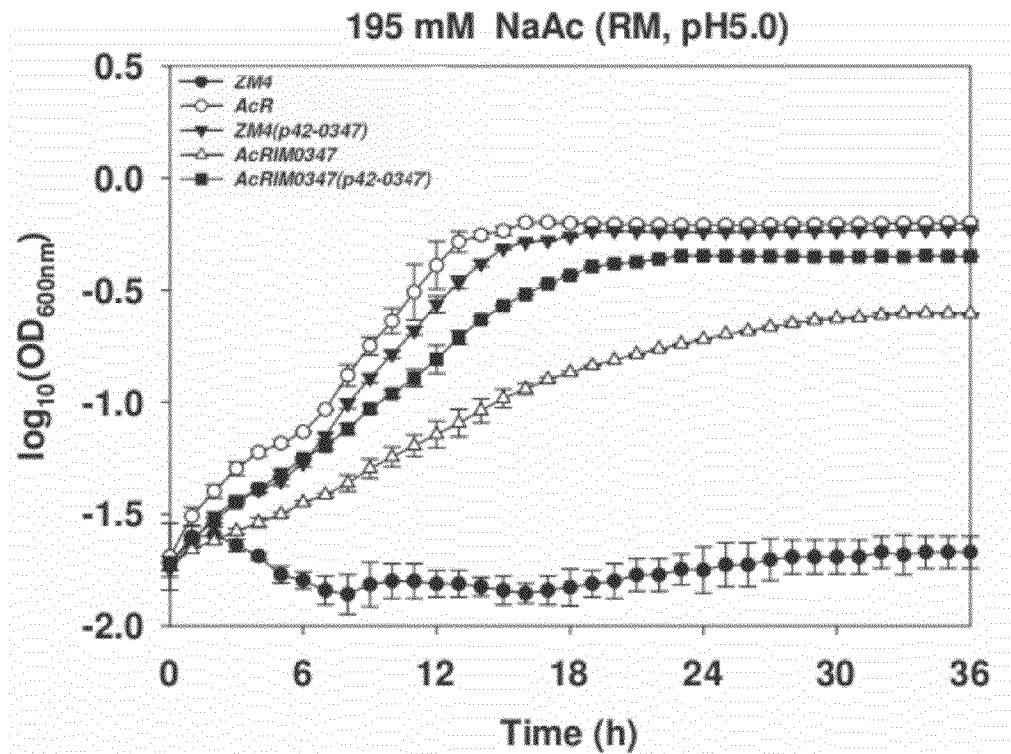

The growth of Z. mobilis strains was reduced in the presence of acetate, vanillin, furfural, or HMF with increased lag phases and/or slower growth rates and/or final bacterial cell densities depending on the respective condition and strain (Tables 3-4; FIGS. 4A-4E and 5A-5E). Among the different forms of acetate counter-ions tested, sodium acetate had the most significant inhibitory effect on wild-type Z. mobilis growth. This was followed by potassium acetate and ammonium acetate, and sodium chloride had the least negative influence on wild-type Z. mobilis growth (Table 3; FIGS. 4A-4E). Wild-type ZM4 growth was completely inhibited when RM medium was supplemented with 195 mM sodium acetate (Table 3; FIG. 4C). Among the pretreatment inhibitors of vanillin, furfural, and HMF, vanillin had the most significant inhibitory effect on Z. mobilis, while HMF had the least effect (Table 4). It took Z. mobilis a longer period of time to complete active growth and reach the stationary phase, which was about 16, 19 or 21 h in the presence of HMF, furfural or vanillin, respectively, as compared to 11 h without any inhibitor present in the medium (FIGS. 5A-5D).

TABLE 3

Growth rate and final cell density of different Z. mobilis strains in the absence or presence of different sodium and acetate ions.

| | | ZM4 | AcR | AcRIM0347 | AcRIM0347 (p42-0347) | ZM4 (p42-0347) |
|---|---|---|---|---|---|---|
| Growth rate (hour$^{-1}$) | RM | 0.42 ± 0.01 | 0.39 ± 0.01 | 0.32 ± 0.003 | 0.33 ± 0.002 | 0.38 ± 0.003 |
| | RM (NaCl) | 0.24 ± 0.008 | 0.29 ± 0.005 | 0.21 ± 0.008 | 0.22 ± 0.009 | 0.25 ± 0.008 |
| | RM (NH$_4$OAc) | 0.20 ± 0.008 | 0.19 ± 0.005 | NA | 0.22 ± 0.002 | 0.19 ± 0.007 |
| | RM (Kac) | 0.15 ± 0.004 | 0.12 ± 0.000 | NA | 0.09 ± 0.003 | 0.12 ± 0.006 |
| | RM (NaAc) | NA | 0.29 ± 0.04 | 0.12 ± 0.004 | 0.16 ± 0.002 | 0.27 ± 0.004 |
| Final Cell Density | RM | 0.95 ± 0.006 | 1.01 ± 0.006 | 0.94 ± 0.004 | 0.92 ± 0.002 | 1.02 ± 0.004 |
| | RM (NaCl) | 0.73 ± 0.01 | 0.96 ± 0.01 | 0.73 ± 0.03 | 0.72 ± 0.02 | 0.84 ± 0.01 |
| | RM (NH$_4$OAc) | 0.43 ± 0.01 | 0.42 ± 0.006 | NA | 0.32 ± 0.007 | 0.37 ± 0.008 |

TABLE 3-continued

Growth rate and final cell density of different Z. mobilis strains
in the absence or presence of different sodium and acetate ions.

|  |  | ZM4 | AcR | AcRIM0347 | AcRIM0347 (p42-0347) | ZM4 (p42-0347) |
|---|---|---|---|---|---|---|
| ($OD_{600 nm}$) | RM (Kac) | 0.42 ± 0.002 | 0.40 ± 0.000 | NA | 0.28 ± 0.007 | 0.34 ± 0.004 |
|  | RM (NaAc) | NA | 0.63 ± 0.02 | 0.25 ± 0.001 | 0.45 ± 0.002 | 0.59 ± 0.002 |

"NA" indicates that the data are not available due to the lack of growth in that condition. The concentration for all the chemicals (NaCl, NH$_4$OAc, KAc, NaAc) supplemented into the RM is 195 mM. NaCl: sodium chloride, NH$_4$OAc: ammonium acetate, KAc: potassium acetate, NaAc: sodium acetate. Strains included in this study are: ZM4: *Zymomonas mobilis* ZM4 wild-type; AcR: ZM4 acetate tolerant mutant; ZM4 (p42-0347): ZM4 containing a gateway plasmid p42-0347 to express ZM4 gene ZMO0347; AcRIM0347: AcR insertional mutant of ZMO0347; AcRIM0347 (p42-0347): AcRIM0347 containing gateway plasmid p42-0347. This experiment has been repeated at least three times with similar result. Duplicate biological replicates were used for each condition.

TABLE 4

Growth rate and final cell density of different Z. mobilis strains
in the absence or presence of different pretreatment inhibitors.

|  |  | ZM4 | AcR | AcRIM0347 | AcRIM0347(p42-0347) |
|---|---|---|---|---|---|
| Growth rate (hour$^{-1}$) | RM | 0.48 ± 0.03 | 0.46 ± 0.003 | 0.35 ± 0.004 | 0.32 ± 0.003 |
|  | HMF | 0.36 ± 0.02 | 0.35 ± 0.01 | 0.19 ± 0.02 | 0.22 ± 0.001 |
|  | Furfural | 0.31 ± 0.01 | 0.30 ± 0.005 | 0.19 ± 0.03 | 0.20 ± 0.01 |
|  | Vanillin | 0.26 ± 0.001 | 0.26 ± 0.01 | 0.20 ± 0.006 | 0.20 ± 0.003 |
| Final Cell Density ($OD_{600 nm}$) | RM | 0.91 ± 0.01 | 0.98 ± 0.006 | 0.95 ± 0.003 | 0.92 ± 0.006 |
|  | HMF | 0.93 ± 0.003 | 0.96 ± 0.006 | 0.67 ± 0.03 | 0.78 ± 0.02 |
|  | Furfural | 0.88 ± 0.006 | 0.89 ± 0.009 | 0.67 ± 0.001 | 0.80 ± 0.02 |
|  | Vanillin | 0.69 ± 0.006 | 0.71 ± 0.01 | 0.66 ± 0.01 | 0.70 ± 0.01 |

The concentration for the inhibitor supplemented into the RM is: HMF: 0.75 g/L, furfural, or vanillin: 1 g/L. Strains included in this study are: ZM4: *Zymomonas mobilis* ZM4 wild-type; AcR: ZM4 acetate tolerant mutant; AcRIM0347: AcR insertional mutant of ZMO0347; AcRIM0347 (p42-0347): AcRIM0347 containing gateway plasmid p42-0347. This experiment has been repeated at least three times with similar result. Duplicate biological replicates were used for each condition.

Hfq Contributes to Sodium and Acetate Ion Tolerances

Figure 5A:
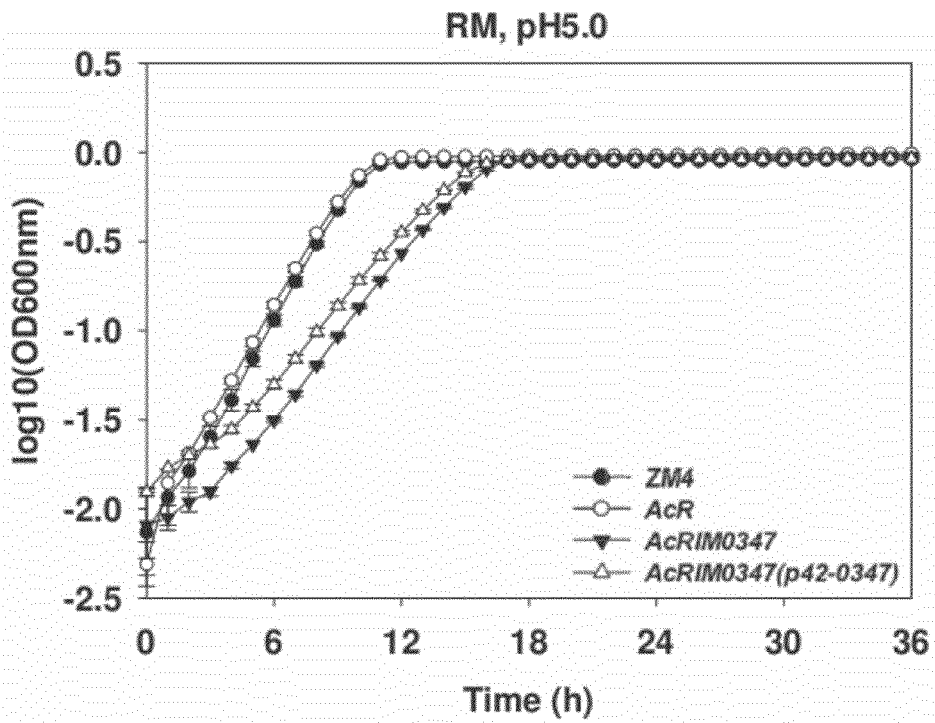
FIGS. 5A-5E. Z. mobilis Hfq conferred tolerance to different classes of pretreatment inhibitors. Z. mobilis strains were grown in RM (pH 5.0) overnight, 5-µL culture were then transferred into 250-µL RM media in the Bioscreen plate. The growth differences of different strains were monitored by Bioscreen (Growth Curves USA, NJ) under anaerobic conditions in RM, pH 5.0 (A), RM with 1 g/L vanillin, pH 5.0 (B), 1 g/L furfural, pH 5.0 (C), 1 g/L HMF, pH 5.0 (D) and 0.001% H$_2$O$_2$ (E). Strains included in this study are: ZM4: Zymomonas mobilis ZM4 wild-type; AcR: ZM4 acetate tolerant mutant; AcRIM0347: AcR insertional mutant of ZMO0347; AcRIM0347 (p42-0347): AcRIM0347 containing gateway plasmid p42-0347 over-expressing ZM4 gene ZMO0347. This experiment has been repeated at least three times with similar result for hydrogen peroxide growth and in duplicate for the vanillin growth.
Figure 5B:
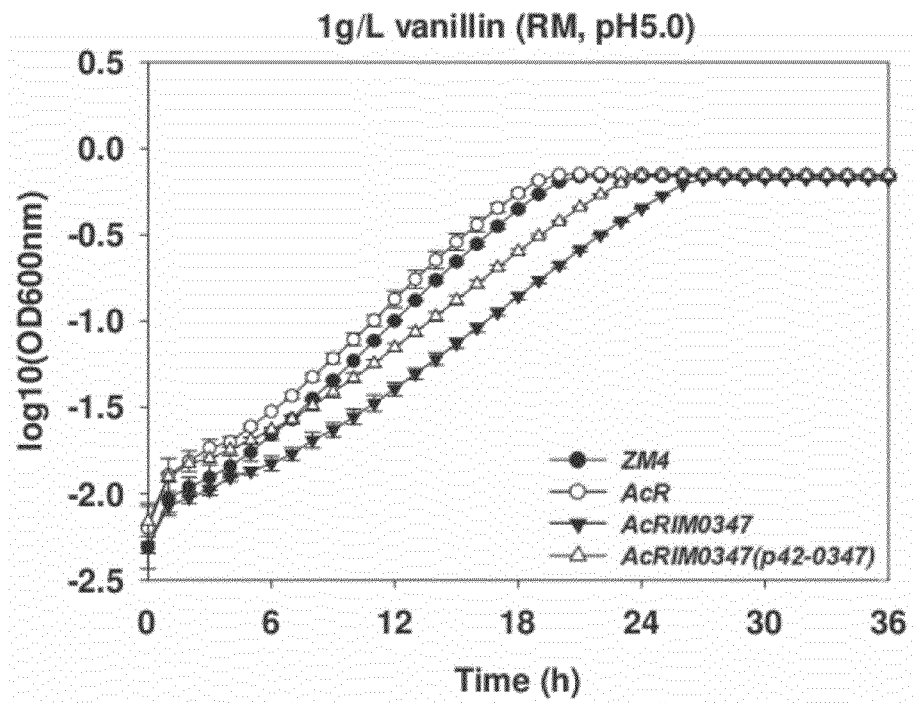
Figure 5C:
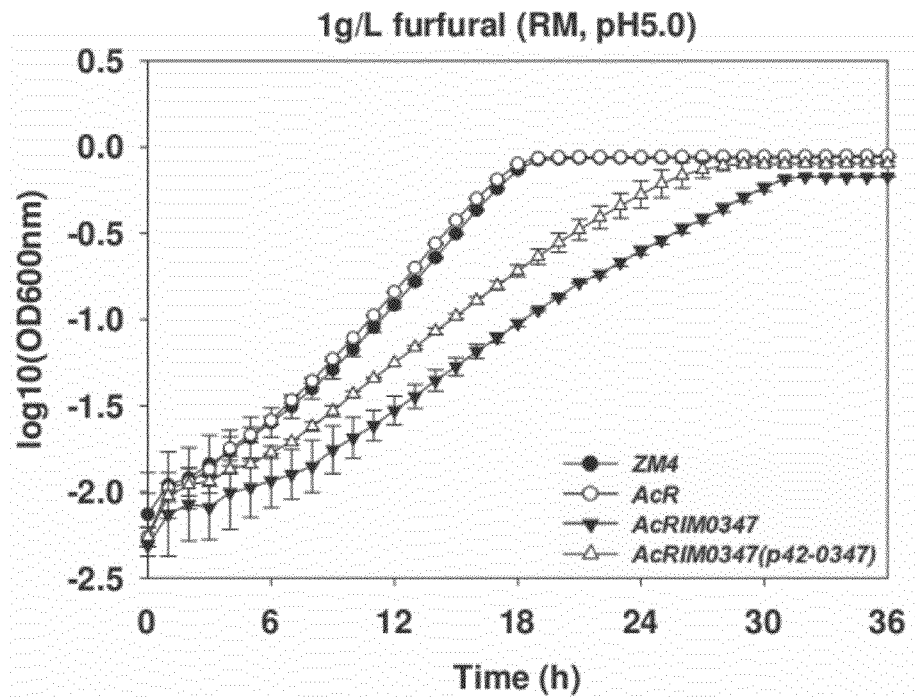
Figure 5D:
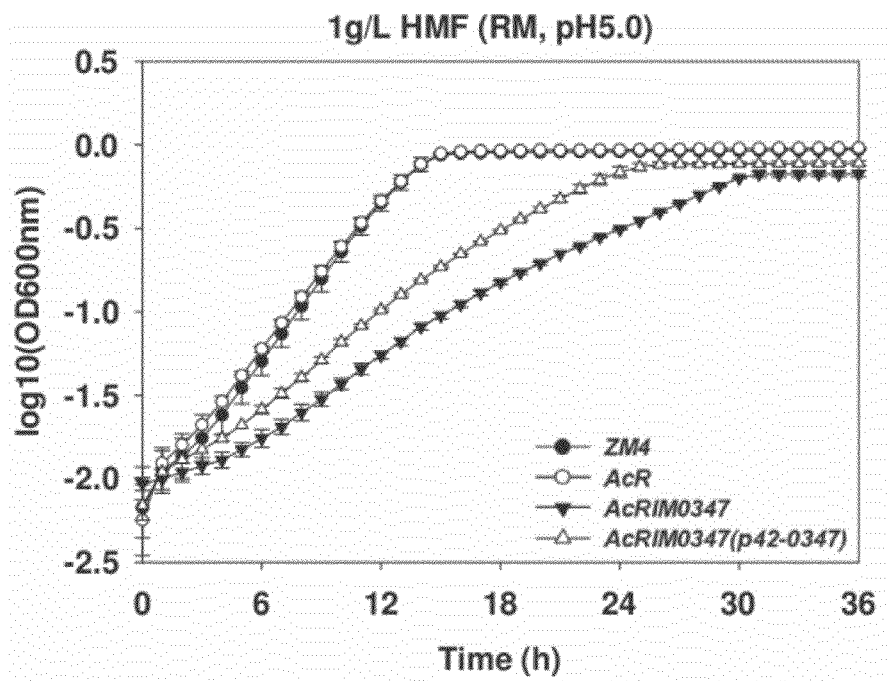

Although the final cell density of hfq mutant AcRIM0347 was similar to that of AcR parental strain (Table 3; FIG. 5A), the growth rate of AcRIM0347 was reduced by about one-fifth even without any inhibitor in the RM, indicating that hfq plays a central role in normal *Z. mobilis* physiology. Wild-type ZM4 that contained p42-0347 was able to grow in the presence of 195 mM sodium acetate and had a similar growth rate and final cell density to that of acetate tolerant strain AcR (Table 3; FIG. 4C). The wild-type ZM4 was unable to grow under this condition.

Figure 4D:
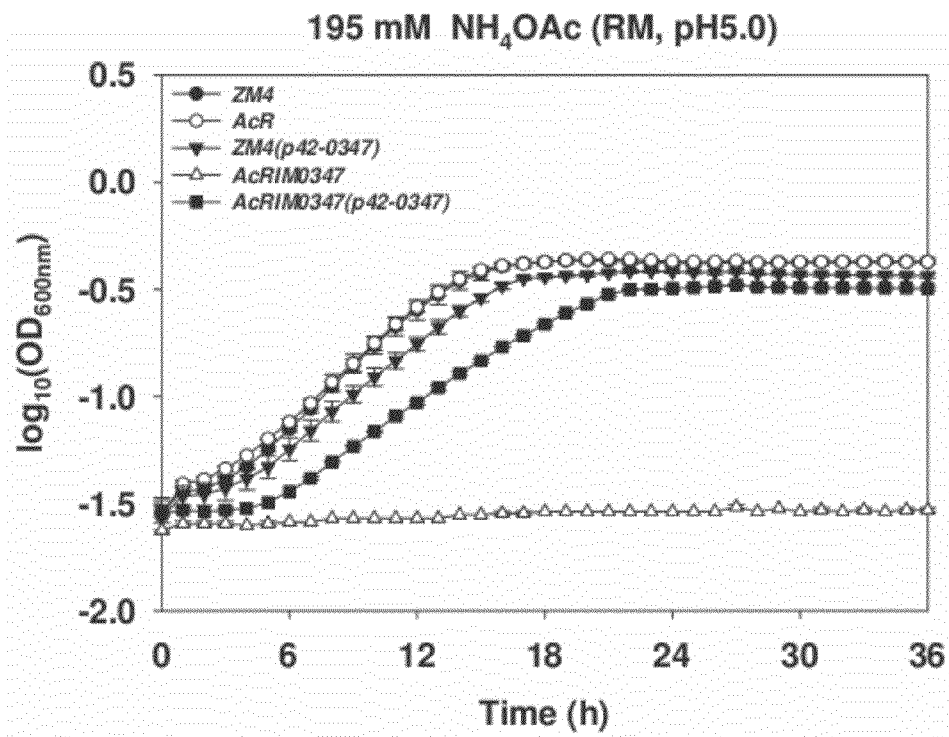
Figure 4E:
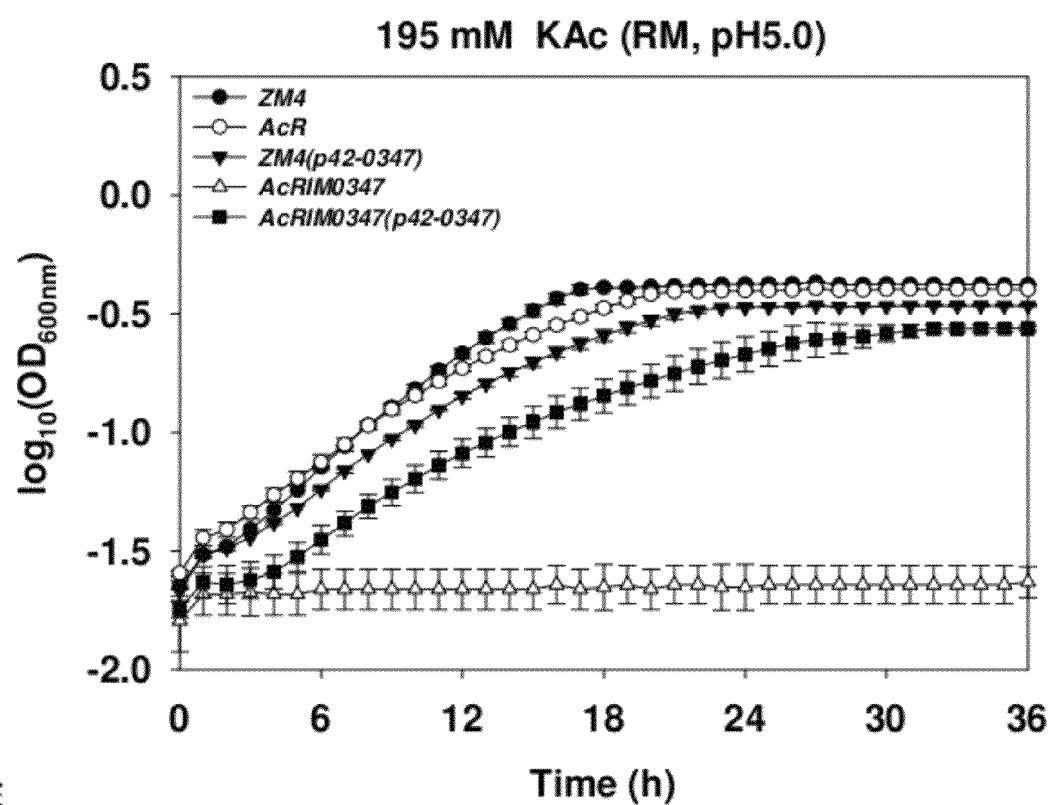

The inactivation of the hfq gene in AcR decreased this acetate tolerant strain's resistance to both sodium ion (sodium chloride) and acetate ion (ammonium acetate and potassium acetate) (Table 3; FIGS. 4A-4E). hfq mutant AcRIM0347 was unable to grow in the presence of 195 mM ammonium acetate or potassium acetate (Table 3; FIGS. 4D-4E). Both the growth rate and final cell density of hfq mutant AcRIM0347 were reduced by at least a quarter in the presence of 195 mM sodium chloride, and about 60% in the presence of 195 mM sodium acetate compared to that of the parental strain AcR (Table 3; FIGS. 4B-4C). The AcRIM0347 hfq mutation was complemented by the introduction of an hfq-expressing plasmid (p42-0347) into the strain. The complemented mutant strain recovered at least half of the parental strains growth rate and 70% of its final cell density in the presence of 195 mM acetate ion (whether as sodium, ammonium or potassium acetate) (Table 3; FIGS. 4A-4E).

Hfq Contributes to Vanillin, Furfural, HMF and $H_2O_2$ Tolerances

AcRIM0347 growth rates were lower than that of ZM4 and AcR under all conditions tests, except for growth in RM broth (Table 4; FIGS. 5A-5D). AcRIM0347 also achieved lower final cell densities compared to ZM4 and AcR (Table 4; FIGS. 5A-5D). When AcRIM0347 was provided functional *Z. mobilis* Hfq via p42-0347, growth rates under all conditions were largely unchanged (Table 4). However, shorter lag phases were observed for AcRIM0347 (p42-0347) grown with vanillin, furfural or HMF and increases in final cell densities were also observed under these conditions (Table 4; FIGS. 5A-5D). These data indicate that hfq is important for optimal *Z. mobilis* growth and its ability to resist furfural, HMF and vanillin toxicity.

Figure 5E:
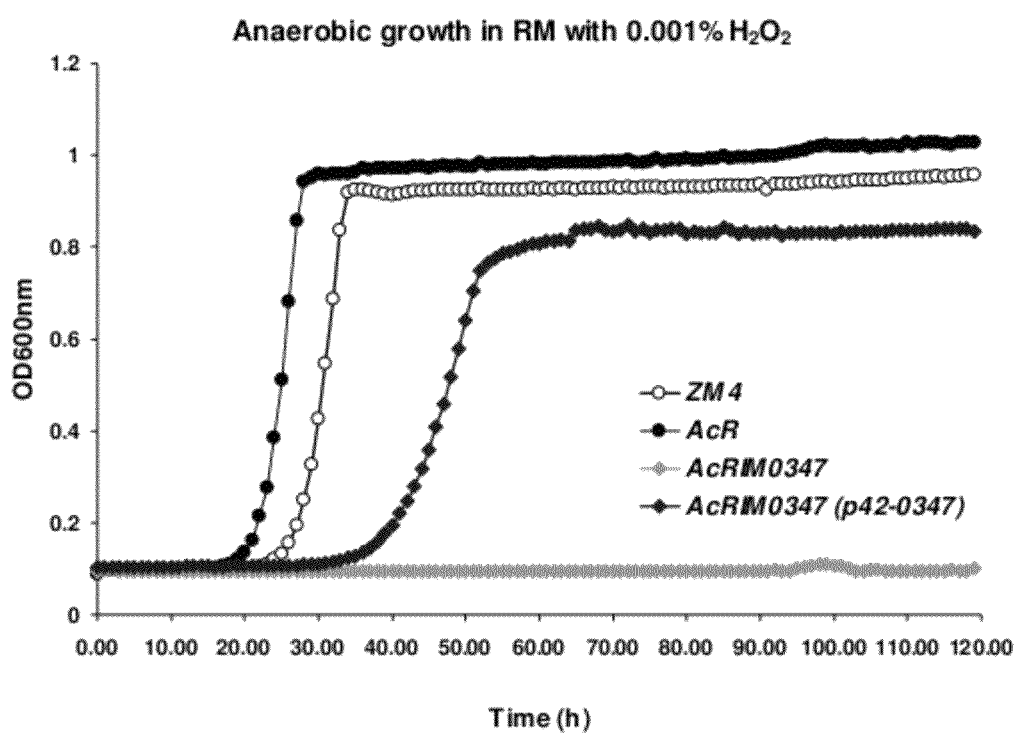

Hfq also contributed to tolerance of other stress such as the reactive oxidative species generating hydrogen peroxide ($H_2O_2$). hfq mutant AcRIM0347 was sensitive to hydrogen peroxide $H_2O_2$ and no observable growth was detected in RM medium with 0.001% $H_2O_2$ (FIG. 5E). The wild-type strain ZM4 and acetate tolerant strain AcR grew well at this concentration. Complementation of the hfq mutant strain allowed strain AcRIM0347(p42-0347) to grow in RM medium with 0.001% $H_2O_2$.

Example 4

This Example describes experiments to show that Yeast Lsm proteins contribute to pretreatment inhibitor tolerance.

Lsm Protein and Yeast Tolerance to Sodium and Acetate Ions

*S. cerevisiae* Sm and Sm-like (Lsm) proteins are similar to *Z. mobilis* Hfq at the level of protein sequence. Growth of yeast Lsm deletion mutants and Lsm over-expressing strains in 305 mM ammonium acetate, potassium acetate, or sodium acetate was assessed to test whether *S. cerevisiae* Lsm proteins and ZM4 Hfq had functionally similar roles.

Figure 6A:
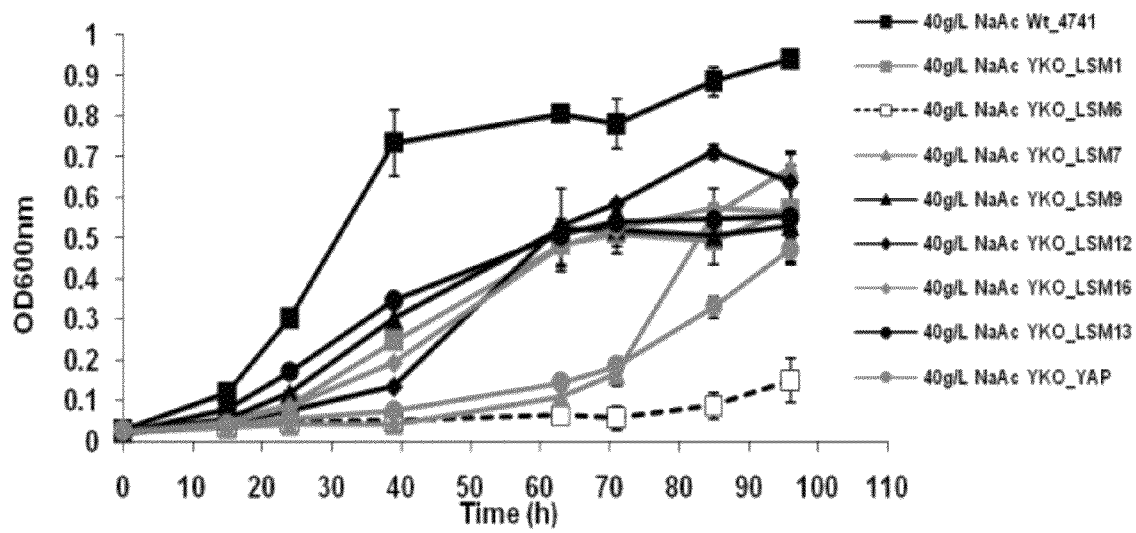
FIGS. 6A-6B. Lsm-like proteins in S. cerevisiae are responsible for sodium acetate tolerance. S. cerevisiae strains were grown in CM with 2% glucose for wild-type BY4741 and the deletion mutants, CM with 2% glucose minus uracil for GST over-expression strains. Five-µL culture was then transferred into 300-µL CM broth in the Bioscreen plate. The growth differences of different strains were monitored by Bioscreen (Growth Curve USA, NJ) containing 40 g/L sodium acetate for yeast deletion mutants (A) and GST over-expression strains (B). This experiment has been repeated at least three times with similar result.
Figure 6B:
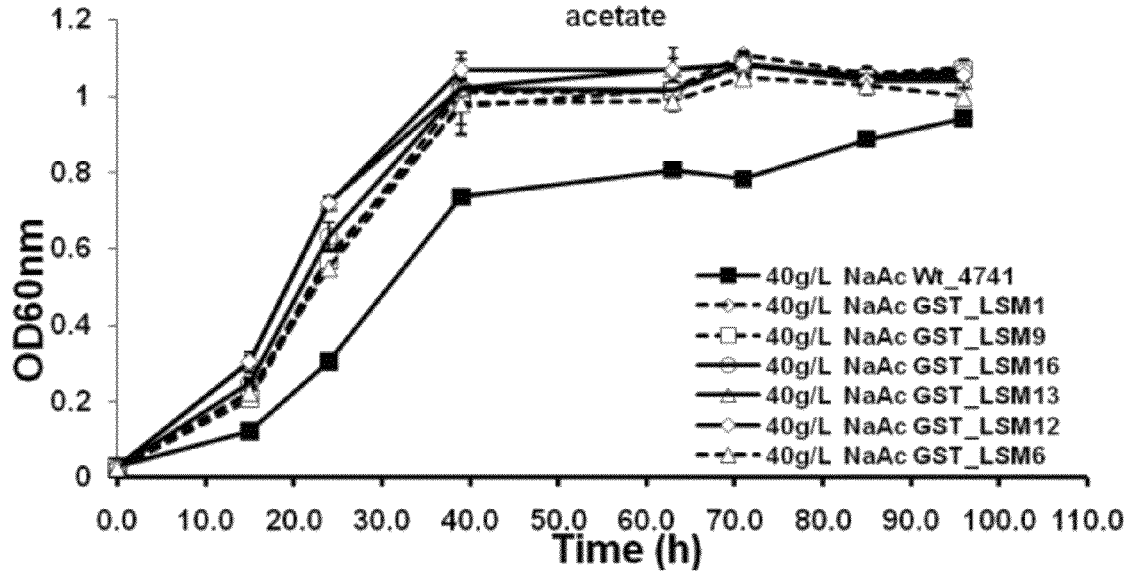

Deletion of seven Lsm genes affecting three Lsm heteroheptameric ring components (Lsm1, Lsm6, Lsm7) and four other Lsm proteins containing an Sm domain (Lsm9, Lsm12, Lsm13, Lsm16), was shown to have negative effects on the growth of *S. cerevisiae* in the presence of sodium acetate 40 g/L (FIG. 6A). On the other hand, six Lsm protein overexpressing *S. cerevisiae* strains (Lsm1, Lsm6, Lsm9, Lsm12, Lsm13, Lsm16) displayed enhanced growth in the presence of sodium acetate 40 g/L (FIG. 6B).

Figure 7A:
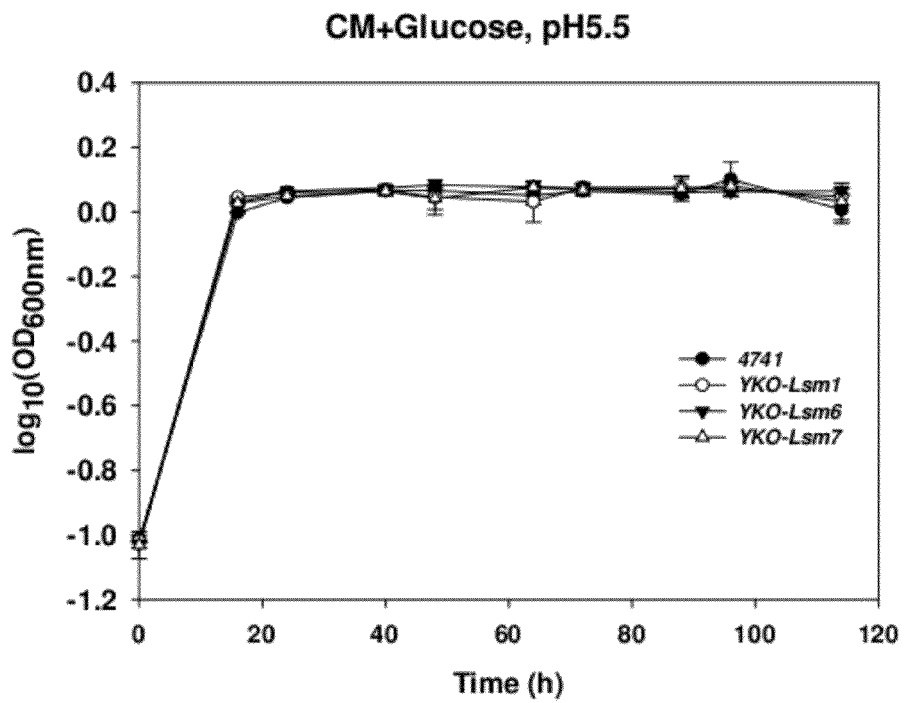
FIGS. 7A-7P. Lsm proteins in S. cerevisiae are involved in multiple inhibitor tolerance. S. cerevisiae strains were grown in CM with 2% glucose (CM+glucose) for wild-type BY4741 and the deletion mutants, CM with 2% glucose and 2% galactose minus uracil (CM+glucose+2% galactose) for GST over-expression strains. A 5-µL culture was then transferred into 250-µL CM broth in the Bioscreen plate. The growth differences of different deletion mutant strains were monitored by Bioscreen (Growth Curves USA, NJ) in CM+glucose at pH 5.5 (A), CM+glucose with 305 mM NaCl, pH 5.5 (B), 305 mM NaAc, pH 5.5 (C), 305 mM NH$_4$OAc, pH 5.5 (D), and 305 mM KAc, pH 5.5 (E), 0.75 g/L vanillin, pH 5.5 (F), 1.5 g/L furfural, pH 5.5 (G), and 1.5 g/L HMF, pH 5.5 (H). The growth differences of different GST-over-expressing strains were monitored by Bioscreen (Growth Curves USA, NJ) in CM+glucose+2% galactose at pH 5.5 (I), CM+glucose+2% galactose with 305 mM NaCl, pH 5.5 (J), 305 mM NaAc, pH 5.5 (K), 305 mM NH$_4$OAc, pH 5.5 (L), 305 mM KAc, pH 5.5 (M), 0.75 g/L vanillin, pH 5.5 (N), 1.5 g/L furfural, pH 5.5 (O), and 1.5 g/L HMF, pH 5.5 (P). Strains included in this study are listed in table 1. This experiment has been repeated at least three times with similar result.
Figure 7B:
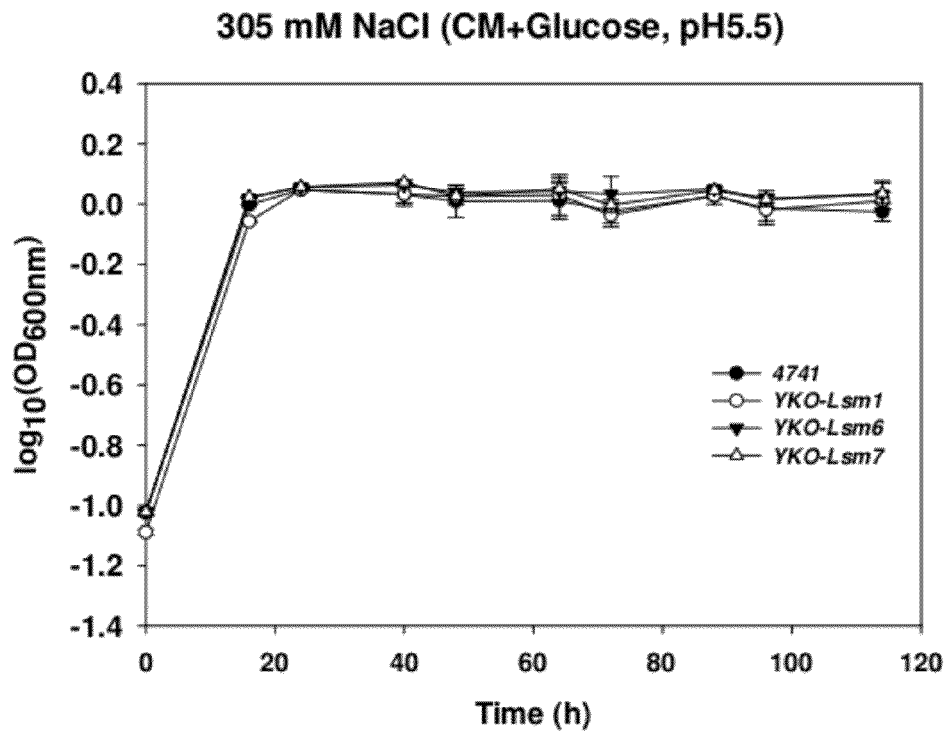
Figure 7C:
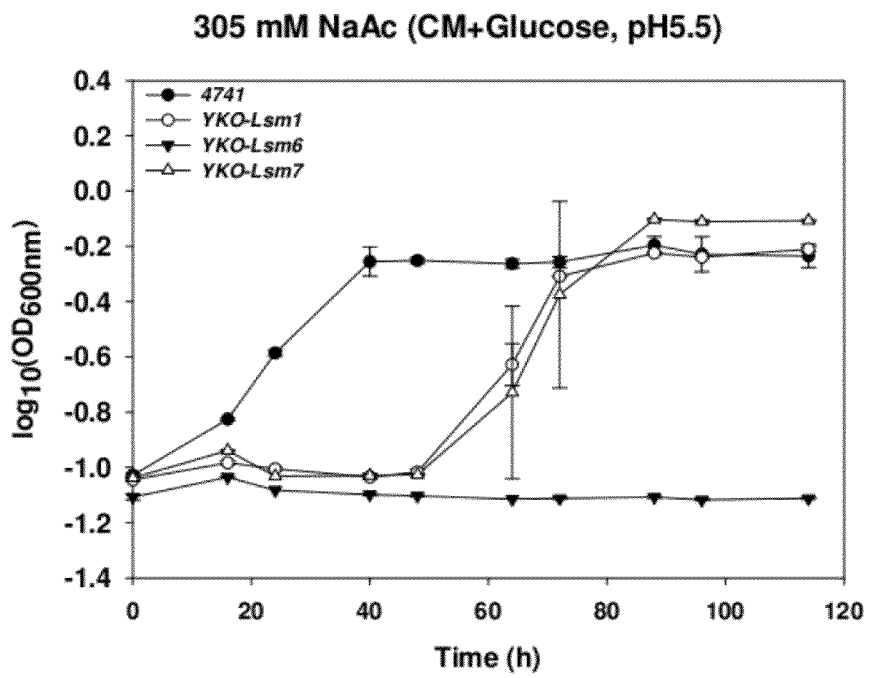
Figure 7D:
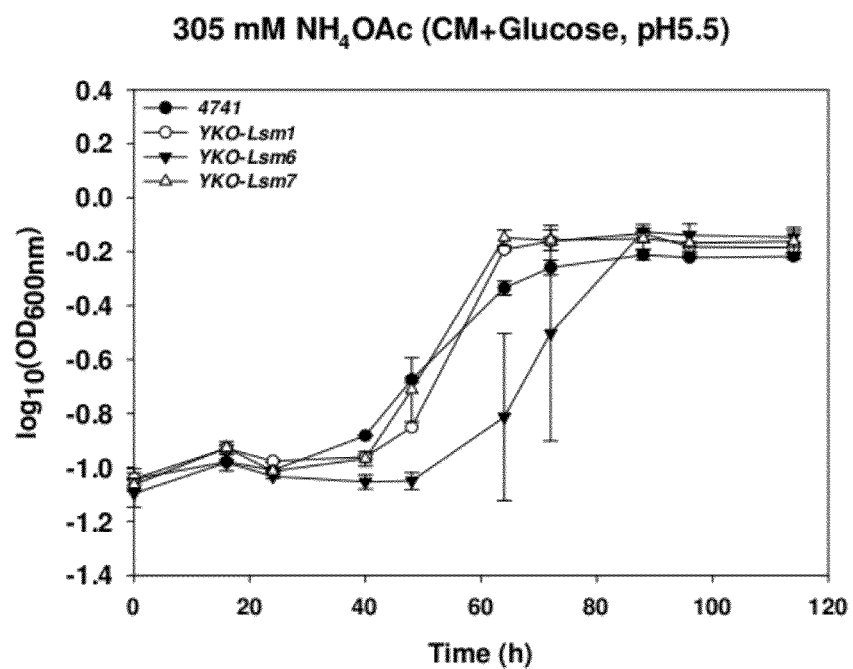
Figure 7E:
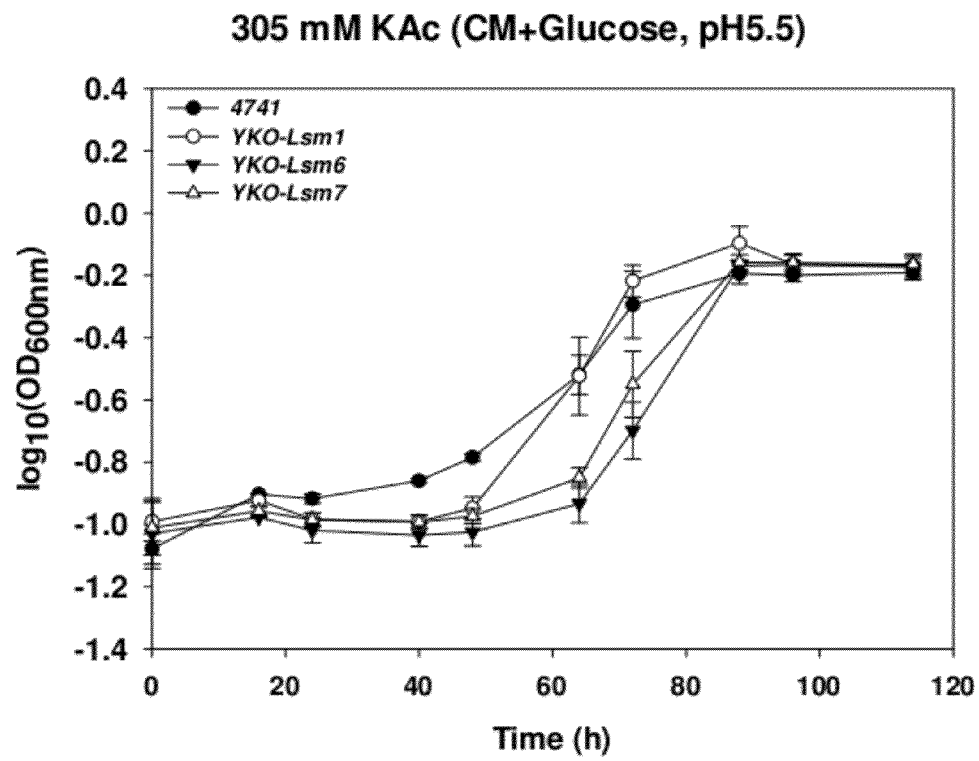
Figure 7F:
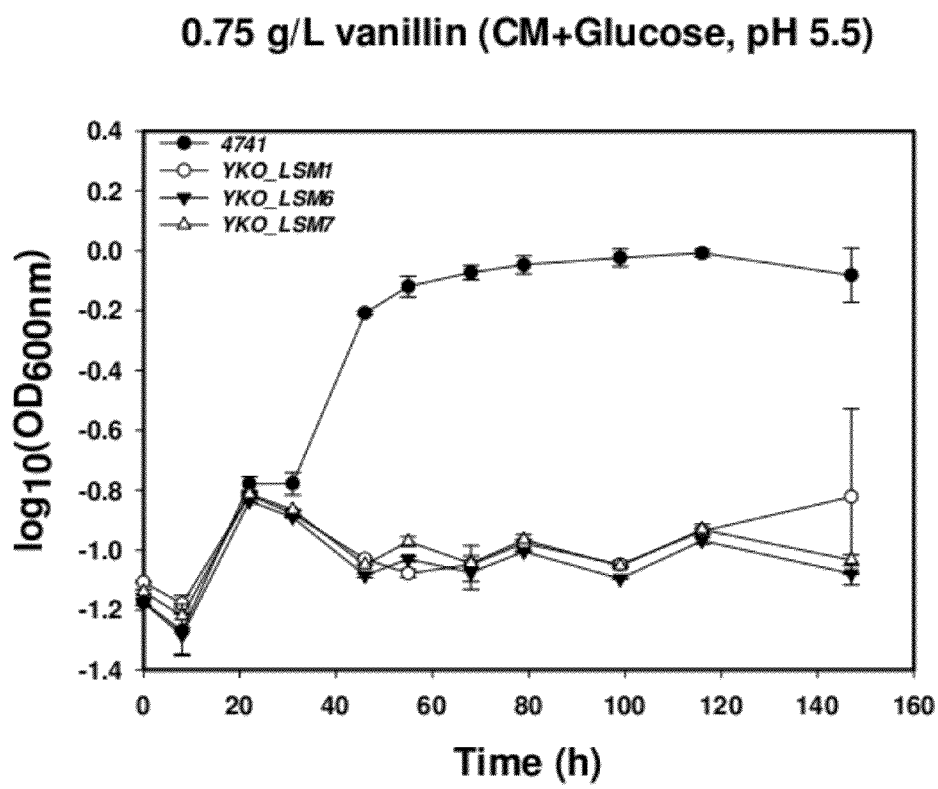
Figure 7G:
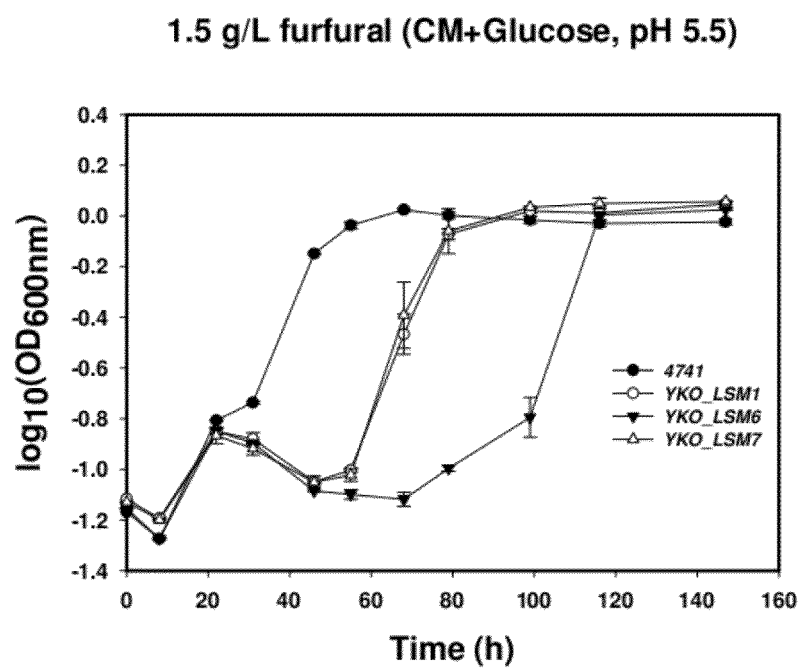
Figure 7H:
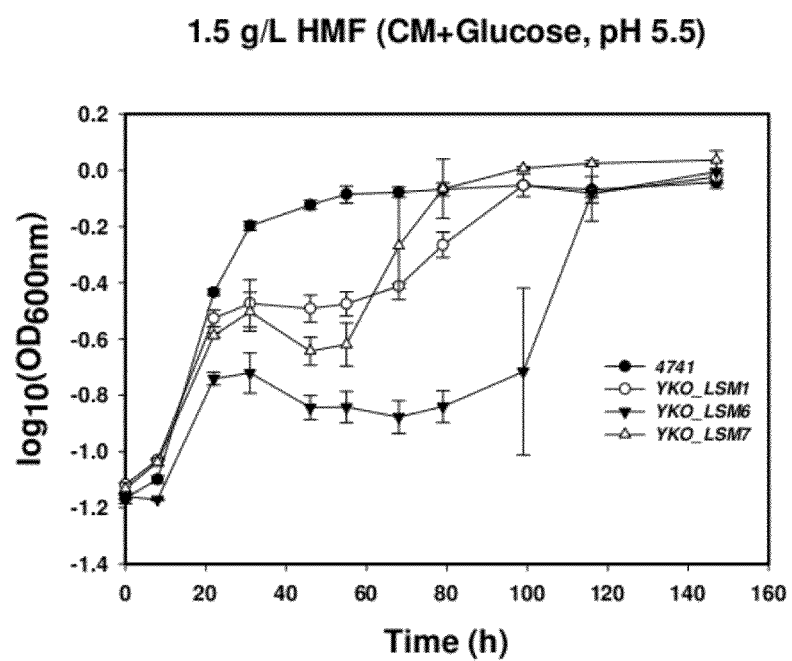
Figure 7I:
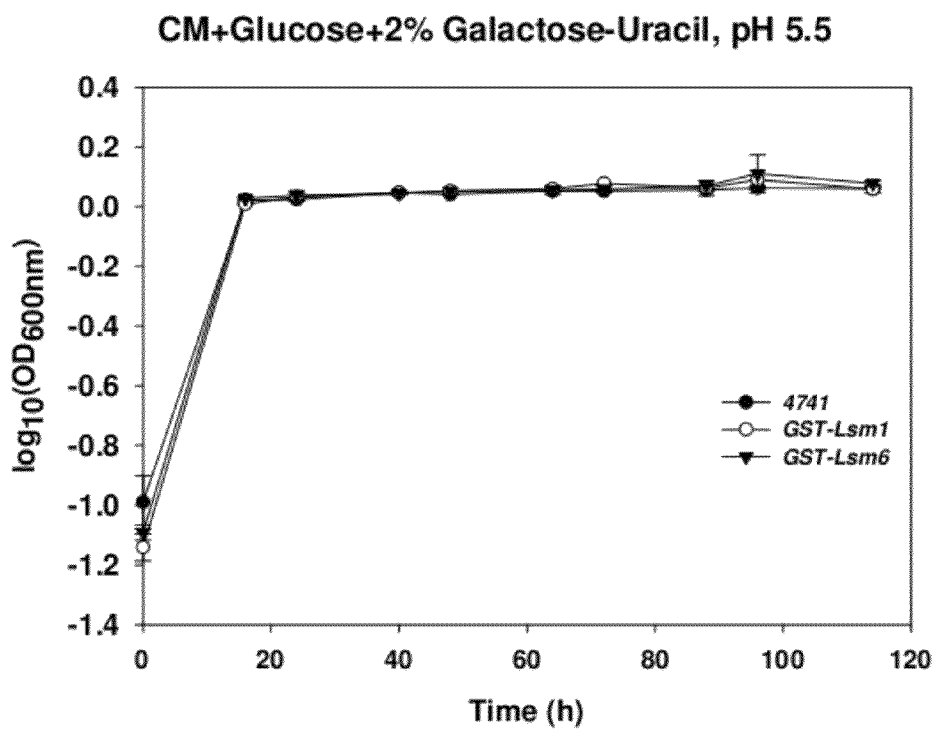
Figure 7J:
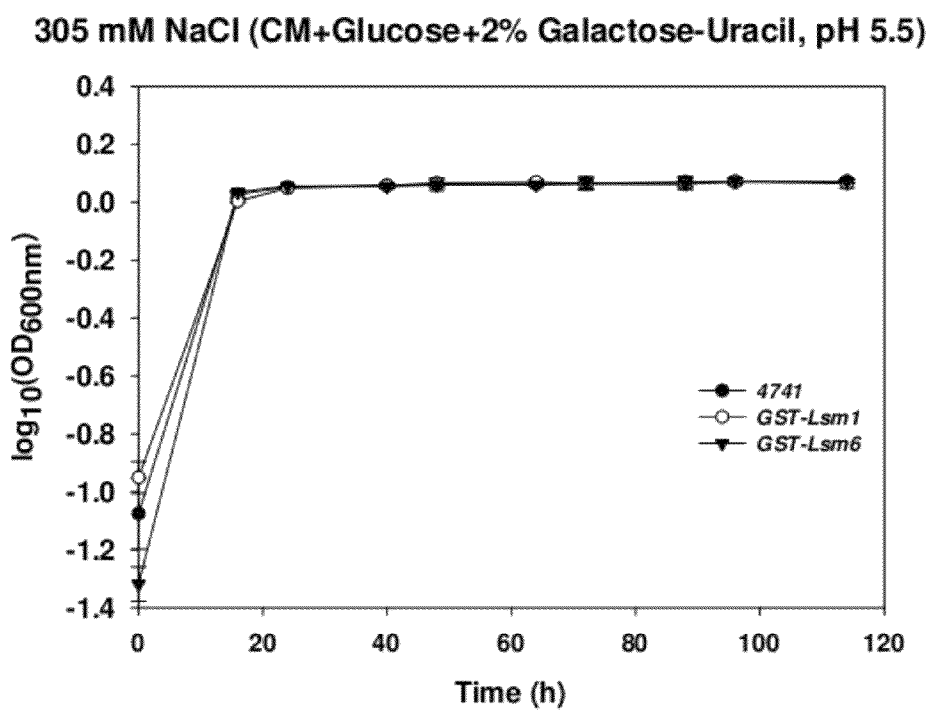
Figure 7K:
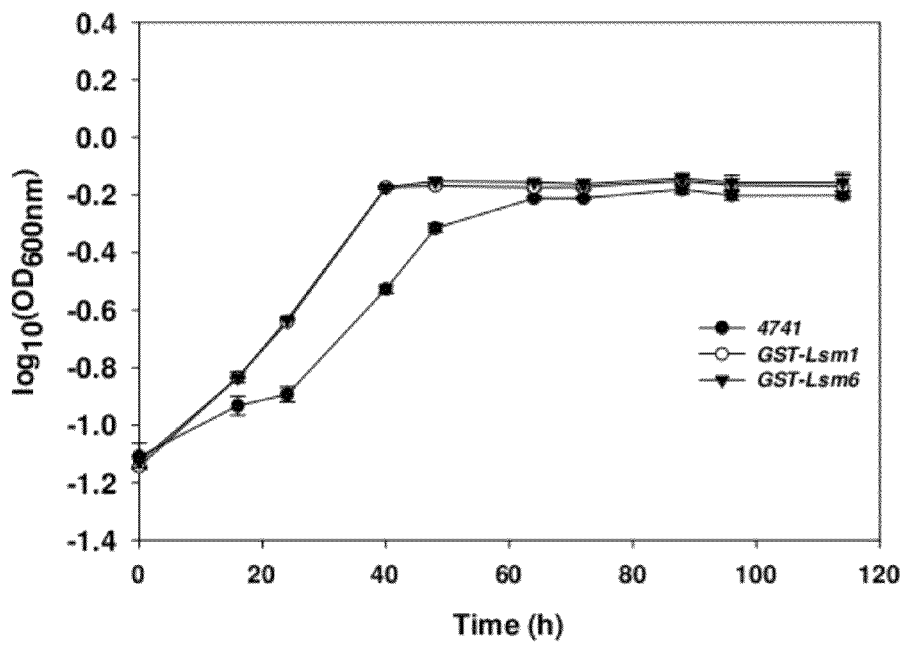
Figure 7L:
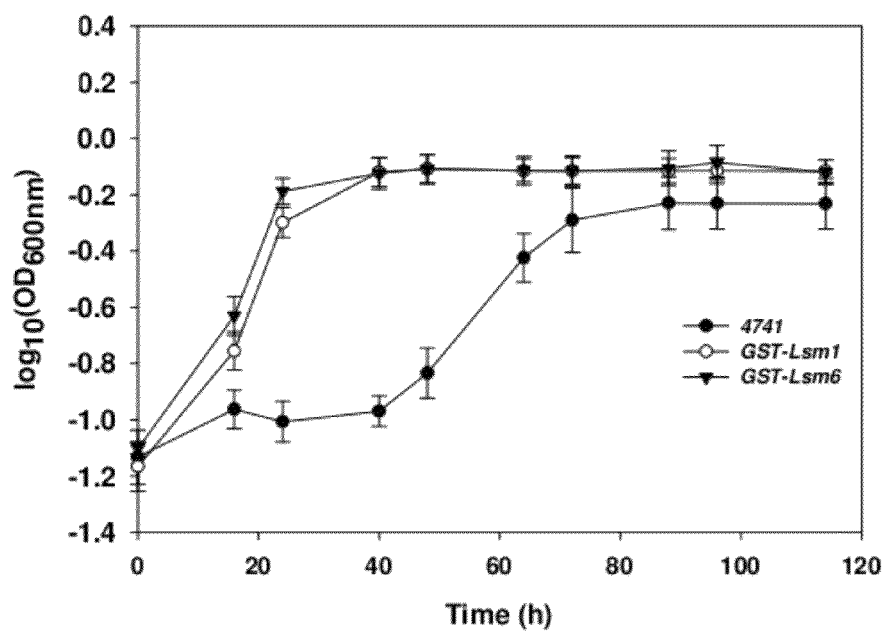
Figure 7M:
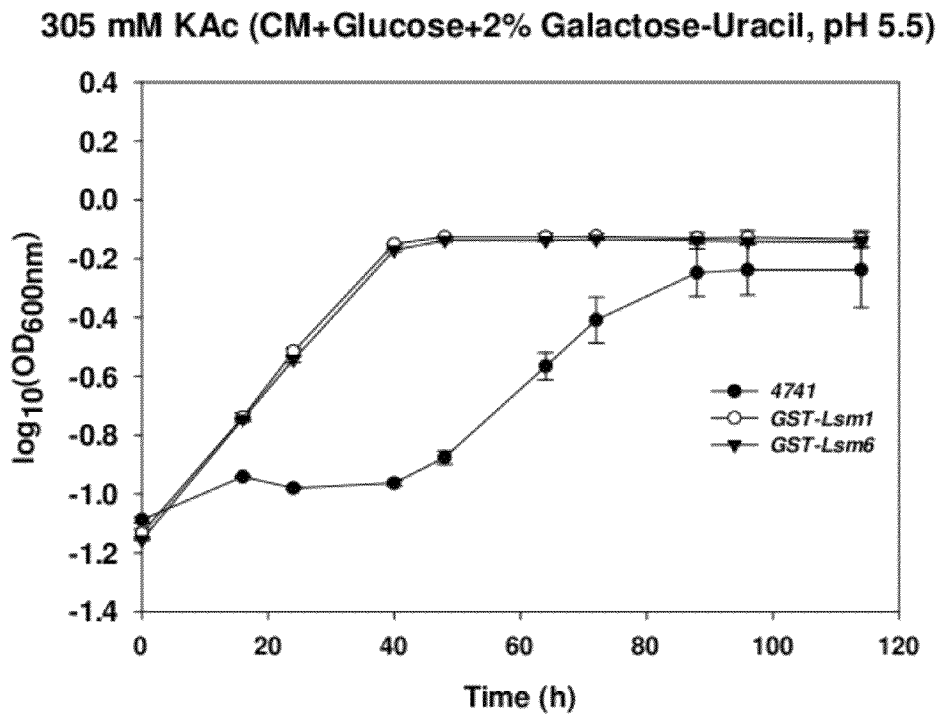

Growth differences between the Lsm mutants and yeast wild-type BY4741 in the CM broth without the addition of acetate or with 305 mM NaCl were not observed (FIGS. 7A-7B, respectively). *S. cerevisiae* Lsm proteins involved in RNA processing ring complex formation (Lsm1, 6, 7), especially Lsm6, played a role in acetate tolerance (FIGS. 7C-7E, 7K-7M). Lsm protein deletion mutants Lsm1, 6, and 7 showed decreased acetate tolerance compared to the wild-type control strain, especially in early growth stages for acetate with sodium, ammonium and potassium counter-ions (FIGS. 7C-7E). The Lsm overexpression strains grew similarly to wild-type BY4741 without the addition of acetate or with 305 mM NaCl (FIGS. 7I, 7J), but each of the Lsm protein overexpression strains showed enhanced acetate tolerance compared to the wild-type strain with sodium, ammonium or potassium counter-ions (FIGS. 7K-7M).

Lsm Proteins and Yeast Tolerance to Vanillin, Furfural and HMF

Figure 7N:
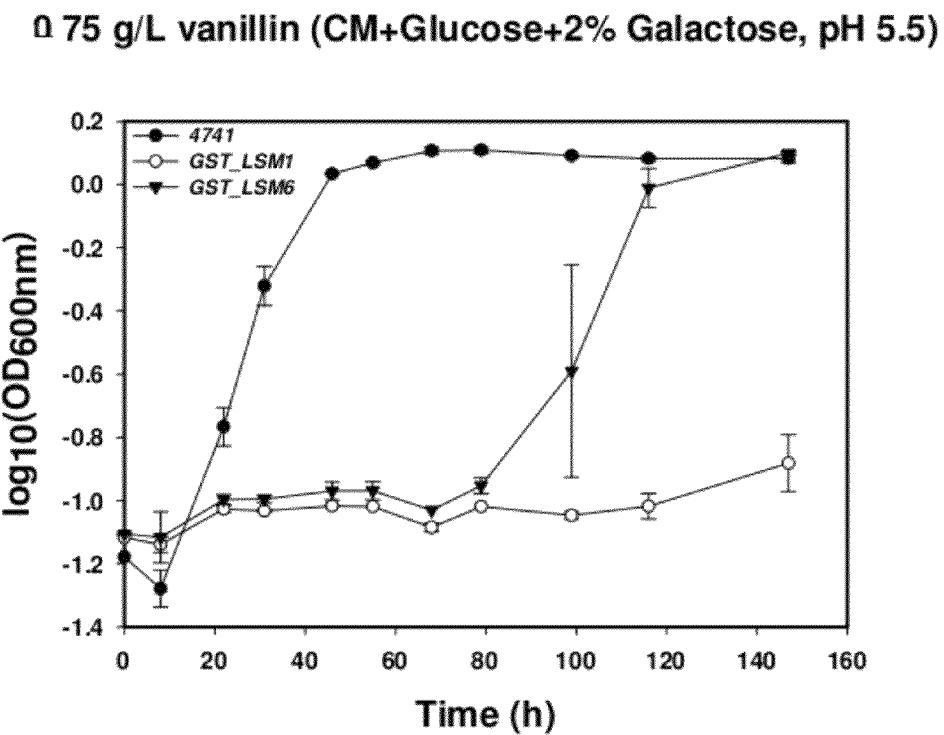
Figure 7O:
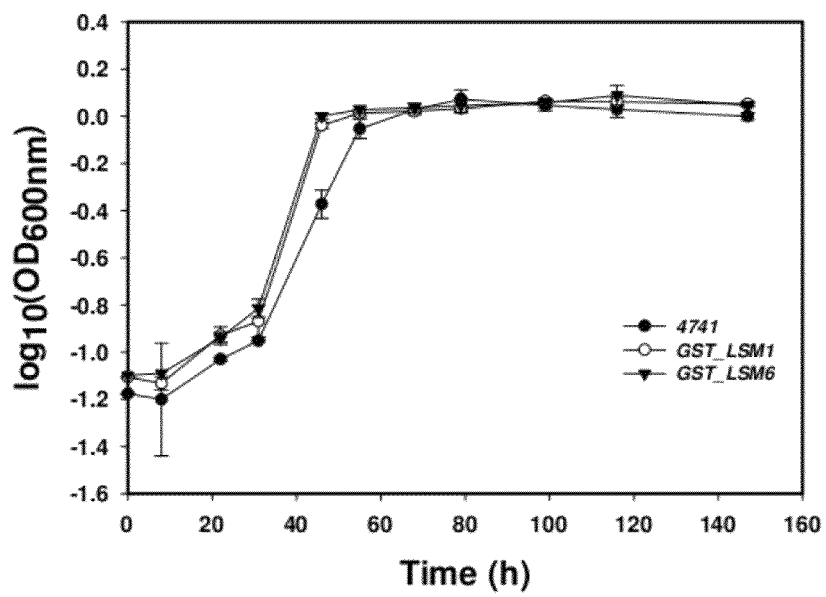
Figure 7P:
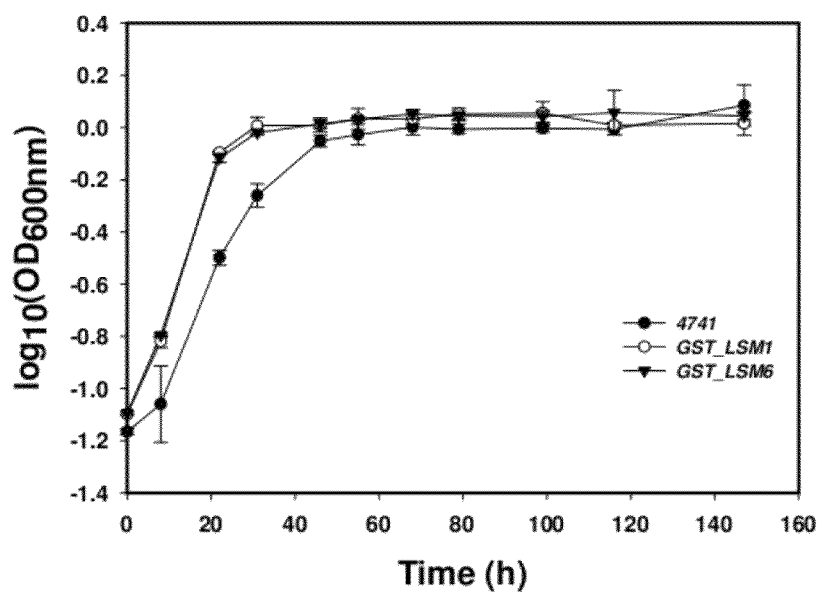

The effect of Lsm proteins on *S. cerevisiae* tolerance to pretreatment inhibitors vanillin, furfural, and HMF was also investigated using the seven Lsm deletion mutants and six Lsm overexpression strains described above. Each yeast deletion mutant and each overexpression strain showed similar growth profiles compared to wild-type strain BY4741 in the absence of inhibitors (FIGS. 7A; 7I). Deletion mutants for Lsm1, 6 and 7 proteins were unable to grow or showed extended lag phases before recovery from the inhibitory effects of pretreatment inhibitors (FIGS. 7F-7H). Overexpression of Lsm proteins provided a slight growth advantage in the presence of 1.5 g/L HMF and furfural (FIGS. 7O-7P). However, a detrimental effect on growth was observed for overexpression strains when cultured in the presence of 0.75 g/L vanillin (FIG. 7N). The data indicated that Lsm proteins Lsm1, 6, and 7 especially Lsm6, which are the components of yeast RNA processing ring complex, play a role in tolerance to the model inhibitors used in this study.

REFERENCES

Alexeyev M F: The pKNOCK series of broad-host-range mobilizable suicide vectors for gene knockout and targeted DNA insertion into the chromosome of gram-negative bacteria. *BioTechniques* 1999, 26(5):824-826, 828.

Almeida J R M, Modig T, Petersson A, Hahn-Hagerdal B, Liden G, Gorwa-Grauslund M F: Increased tolerance and conversion of inhibitors in lignocellulosic hydrolysates by *Saccharomyces cerevisiae*. *J Chem Technol Biotechnol* 2007, 82(4):340-349.

Amberg D C, Burke D J, Strathern J N: Methods in Yeast Genetics: A Cold Spring Harbor Laboratory Course Manual. New York: Cold Spring Harbor Press; 2005.

Baumler D J, Hung K F, Bose J L, Vykhodets B M, Cheng C M, Jeong K C, Kaspar C W: Enhancement of acid tolerance in *Zymomonas mobilis* by a proton-buffering peptide. *Appl Biochem Biotechnol* 2006, 134(1):15-26.

Brown S D: Analysis of a 16 kb region of the *Mesorhizobium loti* R7A symbiosis island encoding bio and nad loci and a novel member of the lad family Dunedin: University of Otago; 2002.

Brown S D, Martin M, Deshpande S, Seal S, Huang K, Alm E, Yang Y, Wu L, Yan T, Liu X et al: Cellular response of Shewanella oneidensis to strontium stress. *Appl Environ Microbiol* 2006, 72(1):890-900.

Chinnawirotpisan P, Theeragool G, Limtong S, Toyama H, Adachi O O, Matsushita K: Quinoprotein alcohol dehydrogenase is involved in catabolic acetate production, while NAD-dependent alcohol dehydrogenase in ethanol assimilation in *Acetobacter pasteurianus* SKU1108. *J Biosci Bioeng.* 2003; 96(6):564-71.

Deanda K, Zhang M, Eddy C, Picataggio S: Development of an arabinose-fermenting *Zymomonas mobilis* strain by metabolic pathway engineering. *Appl Environ Microbiol* 1996, 62(12):4465-4470.

Dien B S, Cotta M A, Jeffries T W: Bacteria engineered for fuel ethanol production: current status. *Appl Microbiol Biotechnol* 2003, 63(3):258-266.

Fukaya M, Takemura H, Okumura H, Kawamura Y, Horinouchi S, Beppu T: Cloning of genes responsible for acetic acid resistance in *Acetobacter aceti*. *J Bacteriol* 1990, 172(4):2096-2104.

Fukaya M, Takemura H, Tayama K, Okumura H, Kawamura Y, Horinouchi S, Beppu T: The aarC gene responsible for acetic acid assimilation confers acetic acid resistance on *Acetobacter aceti*. *J Ferment Bioeng* 1993, 76(4):270-275.

Gunasekaran P, Raj K C: Ethanol fermentation technology—*Zymomonas mobilis*. *Current Science* 1999, 77(1):56-68.

Guisbert E. et al., "Hfq the $\sigma^E$-Mediated Envelope Stress Response and the $\sigma^{32}$-Mediated Cytoplasmic Stress Response in *Escherichia coli*$^\nabla$", *J Bacteriol* 2007 189(5): 1963-1973.

Hermann et al., *EMBO J.* 14: 2976-2088 (1995).

Jeon Y J, Svenson C J, Joachimsthal E L, Rogers P L: Kinetic analysis of ethanol production by an acetate-resistant strain of recombinant *Zymomonas mobilis*. *Biotechnol Lett* 2002, 24(10):819-824.

Joachimstahl E, Haggett K D, Jang J H, Rogers P L: A mutant of *Zymomonas mobilis* ZM4 capable of ethanol production from glucose in the presence of high acetate concentrations. *Biotechnol Lett* 1998, 20(2):137-142.

Joachimsthal E L, Rogers P L: Characterization of a high-productivity recombinant strain of *Zymomonas mobilis* for ethanol production from glucose/xylose mixtures. *Appl Biochem Biotechnol* 2000, 84-6:343-356.

Kadar Z, Maltha S F, Szengyel Z, Reczey K, De Laat W: Ethanol fermentation of various pretreated and hydrolyzed substrates at low initial pH. *Appl Biochem Biotechnol* 2007, 137:847-858.

Kalogeraki V S, Winans S C: Suicide plasmids containing promoterless reporter genes can simultaneously disrupt and create fusions to target genes of diverse bacteria. *Gene* 1997, 188(1):69-75.

Koch B, Jensen L E, Nybroe O: A panel of Tn7-based vectors for insertion of the gfp marker gene or for delivery of cloned DNA into Gram-negative bacteria at a neutral chromosomal site. *J Microbiol Meth* 2001, 45(3):187-195.

Lawford H G, Rousseau J D: Effects of pH and acetic acid on glucose and xylose metabolism by a genetically engineered ethanologenic *Escherichia coli*. *Appl Biochem Biotechnol* 1993, 39:301-322.

Lawford H G, Rousseau J D: Improving fermentation performance of recombinant *Zymomonas* in acetic acid-containing media. Appl Biochem Biotechnol 1998, 70-2:161-172.

Lawford H G, Rousseau J D, Mohagheghi A, McMillan J D: Fermentation performance characteristics of a prehydrolyzate-adapted xylose-fermenting recombinant *Zymomonas* in batch and continuous fermentations. *Appl Biochem Biotechnol* 1999, 77-9:191-204.

Lawford H G, Rousseau J D, Tolan J S: Comparative ethanol productivities of different *Zymomonas* recombinants fermenting oat hull hydrolysate. *Appl Biochem Biotechnol* 2001, 91-3:133-146.

Lawford H G, Rousseau J D: Fermentation performance assessment of a genomically integrated xylose-utilizing recombinant of *Zymomonas mobilis* 39676. *Appl Biochem Biotechnol* 2001, 91-3:117-131.

Lawford H G, Rousseau J D: Cellulosic fuel ethanol—Alternative fermentation process designs with wild-type and recombinant *Zymomonas mobilis*. *Appl Biochem Biotechnol* 2003, 105:457-469.

Matsushita K, Inoue T, Adachi O, Toyama H: *Acetobacter aceti* possesses a proton motive force-dependent efflux system for acetic acid. *J Bacteriol* 2005, 187(13):4346-4352.

McMillan J D: Conversion of hemicellulose hydrolyzates to ethanol. In: *Enzymatic Conversion of Biomass for Fuels Production*. Edited by Himmel MEBJOORP, vol. 566; 1994: 411-437.

Mohagheghi A, Evans K, Chou Y C, Zhang M: Cofermentation of glucose, xylose, and arabinose by genomic DNA-integrated xylose/arabinose fermenting strain of *Zymomonas mobilis* AX101. *Appl Biochem Biotechnol* 2002, 98-100:885-898.

Mohagheghi A, Dowe N, Schell D, Chou Y C, Eddy C, Zhang M: Performance of a newly developed integrant of *Zymomonas mobilis* for ethanol production on corn stover hydrolysate. *Biotechnol Lett* 2004, 26(4):321-325.

Mullins E A, Francois J A, Kappock T J: A specialized citric acid cycle requiring succinyl-coenzyme A (CoA): Acetate CoA-transferase (AarC) confers acetic acid resistance on the acidophile *Acetobacter aceti*. *J Bacteriol* 2008, 190 (14):4933-4940.

Okumura H, Uozumi T, Beppu T: Biochemical characteristics of spontaneous mutants of *Acetobacter aceti* deficient in ethanol oxidation. *Agri Biological Chem* 1985, 49(8): 2485-2487.

Panesar P S, Marwaha S S, Kennedy J F: *Zymomonas mobilis*: an alternative ethanol producer. *J Chem Technol Biotechnol* 2006, 81(4):623-635.

Pecota D C, Kim C S, Wu K W, Gerdes K, Wood T K: Combining the hok/sok, parDE, and pnd postsegregational killer loci to enhance plasmid stability. *Appl Environ Microbiol* 1997, 63(5):1917-1924.

Pelletier et al. "A general system for studying protein-protein interactions in gram-negative bacteria", *J. Proteome Research* 2008, 7(8):3319-3328.

Ranatunga T D, Jervis J, Helm R F, McMillan J D, Hatzis C: Identification of inhibitory components toxic toward *Zymomonas mobilis* CP4(pZB5) xylose fermentation. *Appl Biochem Biotechnol* 1997, 67(3):185-198.

Rogers P L, Goodman A E, Heyes R H: *Zymomonas* ethanol fermentations. *Microbiol. Sci* 1984, 1(6):133-136.

Rogers P L, Jeon Y J, Lee K J, Lawford H G: *Zymomonas mobilis* for fuel ethanol and higher value products. In: *Biofuels*. vol. 108; 2007: 263-288.

Steiner P, Sauer U: Overexpression of the ATP-dependent helicase RecG improves resistance to weak organic acids in *Escherichia coli*. *Appl Microbiol Biotechnol* 2003, 63(3):293-299.

Swings J, De Ley J: The biology of *Zymomonas mobilis*. *Bacteriol Rev* 1977, 41:1-46.

Takahashi C M, Takahashi D F, Carvalhal M L C, Alterthum F: Effects of acetate on the growth and fermentation performance of *Escherichia coli* K011. *Appl Biochem Biotechnol* 1999, 81(3):193-203.

Takemura H, Horinouchi S, Beppu T: Novel insertion sequence IS1380 from *Acetobacter pasteurianus* is involved in loss of ethanol oxidizing ability. *J Bacteriol* 1991, 173(22):7070-7076.

Tiffany Ho-Ching et al., "Characterization of broadly pleiotropic phenotypes caused by an hfq insertion mutation in *Escherichia coli* K-12", *Mol Microbiol* 1994 13(1): 35-49.

Tsui H C, Leung H C, Winkler M E.: Characterization of broadly pleiotropic phenotypes caused by an hfq insertion mutation in *Escherichia coli* K-12. *Mol. Microbiol.* 1994 July; 13(1):35-49.

Valentin-Hansen et al. "The bacterial Sm-like protein Hfq: a key player in RNA transactions", *Mol Microbiol* 2004, 51(6): 1525-1533.

Yang S, Tschaplinski T J, Engle N L, Carroll S L, Martin S L, Davison B H, Palumbo A V, Rodriguez M Jr, Brown S D: Transcriptomic and metabolomic profiling of *Zymomonas mobilis* during aerobic and anaerobic fermentations. *BMC Genomics*. 2009 Jan. 20; 10:34.

Zhang A. et al., "The Sm-like Hfq Protein Increases OxyS RNA Interaction with Target mRNAs", *Mol Cell* 2002 9: 11-22.

Zhang A. et al., "Global analysis of small RNA and mRNA targets of Hfq", *Mol Microbiol* 2003, 50(4): 1111-1124.

Zhang M, Eddy C, Deanda K, Finkestein M, Picataggio S: Metabolic engineering of a pentose metabolism pathway in ethanologenic *Zymomonas mobilis*. *Science* 1995, 267(5195):240-243.

What is claimed is:

1. A method of producing alcohol from a cellulosic biomass material, comprising:
   a. adding a genetically modified fungus to a fermentation mixture comprising a cellulosic biomass material or fermentation substrates derived from said cellulosic biomass material, wherein said genetic modification to said fungus comprises introduction of an expression vector comprising the coding sequence of a yeast protein of the Sm-like superfamily, and wherein said genetic modification results in elevated tolerance to at least one inhibitory chemical compound formed during biomass pretreatment as compared to without the genetic modification;
   b. allowing said microorganism to ferment and produce alcohol; and
   c. recovering alcohol produced by fermentation with said fungus.

2. The method of claim 1, wherein said fungus is a fungal species selected from *Saccharomyces* sp., *Kluyveromyces* sp., *Pichia* sp., *Candida* sp., and *Schizosaccharomycetes* sp.

3. The method of claim 2, wherein said fungal species is yeast selected from *S. cerevisiae* or *P. pastoris*.

4. The method of claim 3, wherein said yeast protein is a yeast Sm or Lsm protein.

5. The method of claim 4, wherein said protein comprises an amino acid sequence selected from any one of SEQ ID NOS: 14, 16, 18, 20, 22, 24, 26, 28, 30, 32, 34, 36, 38, 40, 42, 44, 46, 48 or 50, or a protein sequence that shares at least 95% sequence identity therewith.

6. The method of claim 1, wherein said expression vector is a replicative vector or an integrative vector.

7. The method of claim 1, wherein said at least one inhibitory chemical compound formed during biomass pretreatment is selected from the group consisting of an acetate salt, vanillin, furfural, hydroxymethylfurfural (HMF) and $H_2O_2$.

8. The method of claim 7, wherein said acetate salt is selected from the group consisting of sodium acetate, ammonium acetate and potassium acetate.

9. The method of claim 1, wherein said enhanced tolerance is characterized by ability to grow in a media containing sodium acetate at a concentration of 195 mM.

* * * * *

UNITED STATES PATENT AND TRADEMARK OFFICE
CERTIFICATE OF CORRECTION

PATENT NO.        : 8,790,902 B2                                           Page 1 of 1
APPLICATION NO.   : 13/589709
DATED             : July 29, 2014
INVENTOR(S)       : Steven D. Brown et al.

It is certified that error appears in the above-identified patent and that said Letters Patent is hereby corrected as shown below:

Title page, item (73) Assignee: should read: UT-Battelle, LLC, Oak Ridge, TN (US)

Signed and Sealed this
Twenty-fourth Day of February, 2015

Michelle K. Lee
*Deputy Director of the United States Patent and Trademark Office*